United States Patent
Pardal Filipe et al.

(10) Patent No.: US 12,383,548 B2
(45) Date of Patent: Aug. 12, 2025

(54) ANTIBACTERIAL QUINOLINES

(71) Applicant: Tecnimede—Sociedade Técnico-Medicinal, SA, Sintra (PT)

(72) Inventors: Augusto Eugénio Pardal Filipe, Sintra (PT); Carla Patrícia Da Costa Pereira Rosa, Sintra (PT); Ana Vanessa Cordeiro Simões, Sintra (PT); João Carlos Ramos Damil, Sintra (PT); João Pedro Silva Serra, Sintra (PT); Ana Lúcia Almeida Ferreira, Sintra (PT); Rita Isabel Gomes Neves, Sintra (PT); Sara Alexandra Marques Homem E Sousa Dos Santos, Sintra (PT)

(73) Assignee: Tecnimede—Sociedade Técnico-Medicinal, SA, Sintra (PT)

( * ) Notice: Subject to any disclaimer, the term of this patent is extended or adjusted under 35 U.S.C. 154(b) by 564 days.

(21) Appl. No.: 17/789,472

(22) PCT Filed: Dec. 28, 2020

(86) PCT No.: PCT/IB2020/062483
§ 371 (c)(1),
(2) Date: Jun. 27, 2022

(87) PCT Pub. No.: WO2021/130732
PCT Pub. Date: Jul. 1, 2021

(65) Prior Publication Data
US 2023/0106913 A1    Apr. 6, 2023

(30) Foreign Application Priority Data

Dec. 27, 2019 (PT) .......................................... 116028
Mar. 13, 2020 (EP) ...................................... 20163200
Mar. 13, 2020 (PT) .......................................... 116168

(51) Int. Cl.
*A61K 31/4709* (2006.01)
*A61P 31/06* (2006.01)

(52) U.S. Cl.
CPC .......... *A61K 31/4709* (2013.01); *A61P 31/06* (2018.01)

(58) Field of Classification Search
CPC ............................ A61K 31/4709; A61K 31/06
See application file for complete search history.

(56) References Cited

U.S. PATENT DOCUMENTS 7,868,022 B2    1/2011  Baxter et al.
7,989,628 B2    8/2011  Kolczewski et al.
8,163,756 B2 *  4/2012  Flynn ................... C07D 413/10
                                                    546/275.4
9,856,208 B2 *  1/2018  Lumb ................... C07F 7/0812
2016/0113919 A1  4/2016  Banaei et al.

FOREIGN PATENT DOCUMENTS

| EP | 0694543 A1 | 1/1996 |
| EP | 1527050 B1 | 4/2010 |
| WO | 2009001060 A2 | 12/2008 |
| WO | 2012025237 A9 | 3/2012 |
| WO | 2017001661 A1 | 1/2017 |
| WO | 2017027768 A1 | 2/2017 |
| WO | 2019243971 A1 | 12/2019 |

OTHER PUBLICATIONS

International Search Report and Written Opinion for corresponding PCT Application No. PCT/IB2020/062483 dated Mar. 11, 2021 (8 pages).
Comas et al., "Out-of-Africa migration and Neolithic co-expansion of *Mycobacterium tuberculosis* with modern humans", Nature genetics, Oct. 2013.
Hoagland et al., "New agents for the treatment of drug-resistant *Mycobacterium tuberculosis*", Advanced drug delivery reviews, Jul. 2016.
SJ Tantry et al., "Scaffold Morphing Led to Evolution of 2,4-Diaminoquinolines and Aminopyrazolopyrimidines As Inhibitors of ATP Synthesis Pathway", MedChemComm, Mar. 2016.
Ann H. Cory et al., "Use of an Aqueous Soluble Tetrazolium/Formazan Assay for Cell Growth Assays in Culture", Cancer communications. Jul. 1991, pp. 207-212.
Juan-Carlos Palomino et al., "Resazurin Microtiter Assay Plate: Simple and Inexpensive Method for Detection of Drug Resistance in *Mycobacterium tuberculosis*", Antimicrobial Agents and Chemotherapy, Aug. 2002, pp. 2720-2722.
Vivekkumar K. Redasani et al., "Prodrug Design: Perspectives, Approaches and Applications in Medicinal Chemistry", Academic Press, Jul. 2015.
World Health Organization, "Global Tuberculosis Report", 2017.

* cited by examiner

*Primary Examiner* — D Margaret M Seaman
(74) *Attorney, Agent, or Firm* — Leason Ellis LLP

(57) ABSTRACT

The present disclosure relates to 6-substituted quinoline-2-piperidine derivatives for use in the treatment and/or prevention of tuberculosis.

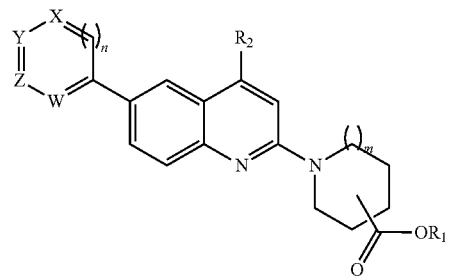

Formula I

20 Claims, No Drawings

1

ANTIBACTERIAL QUINOLINES

CROSS-REFERENCE TO RELATED APPLICATIONS

This application is a U.S. National Stage Application under 35 U.S.C. § 371 of International Patent Application No. PCT/IB2020/062483, filed Dec. 28, 2020, which claims priority to Portugal Patent Application No. 116028, filed Dec. 27, 2019, Portugal Patent Application No. 116168, filed Mar. 13, 2020 and European Patent Application No. 20163200.7 filed Mar. 13, 2020, which are hereby incorporated by reference in their respective entireties.

TECHNICAL FIELD

The present disclosure relates to novel 6-substituted quinoline-2-piperidine derivatives according to general Formula I, II, III and IV, or a pharmaceutically acceptable acid or base addition salts, hydrate, solvate, N-oxide, stereochemically isomer forms, in particular diastereoisomer, enantiomer or atropisomers, or mixtures thereof, a polymorph or ester thereof. The present disclosure also relates to a pharmaceutical composition comprising a compound or prodrug thereof of Formula I, II, III and IV, to the combination of that compound with at least one tuberculosis drug and, to its use in the treatment and/or prevention of tuberculosis.

BACKGROUND

*Mycobacterium tuberculosis* (MTB) has been a major human pathogen since the beginning of human existence. As the human race began to thrive, MTB spread more easily, and it became one of the leading causes of death by the beginning of the twentieth century (Comas et al. *Nat. Genet.* 2013, 45, 1176-1182). The prognosis for patients with tuberculosis (TB) improved dramatically with the discovery and use of antitubercular drugs.

Tuberculosis (TB) is an airborne disease caused by *Mycobacterium tuberculosis* and seven closely related mycobacterial species, namely *Mycobacterium bovis, Mycobacterium africanum, Mycobacterium microti, Mycobacterium caprae, Mycobacterium pinnipedii, Mycobacterium canetti* and *Mycobacterium mungi*, which together comprise what is known as the *Mycobacterium tuberculosis* complex. The majority of TB cases are caused by tubercle bacilli (MTB).

*Mycobacterium tuberculosis* is carried in airborne particles (droplet nuclei) of 1-5 μm in diameter. Infectious droplet nuclei are generated by persons who have pulmonary or laryngeal TB disease. Transmission occurs when an individual inhales droplet nuclei containing MTB, and the droplet nuclei traverse the oro-nasal passage, upper respiratory tract, and bronchi to reach the alveoli. These tubercle bacilli are phagocytosed by alveolar macrophages; the majority of these bacilli are destroyed or inhibited. A small number may multiply intracellularly and are released after macrophage destruction. These tubercle bacill may spread through the lymphatic system or the bloodstream to distant organs, frequently the regional lymph nodes, the lung (apex), the kidneys, the brain and the bones. This process of dissemination stimulates the immune system for a systemic response.

Individuals with latent tuberculosis infection (LTBI) are carriers of the bacteria, but do not manifest symptoms of TB disease and do not spread the infection to others. The LTBI begins when extracellular bacilli are ingested by macrophages and presented to other white blood cells. This triggers the immune response in which white blood cells kill or encapsulate most of the bacilli, leading to the formation of a granuloma. At this point, LTBI has been established. Latent tuberculosis infection (LTBI) can be detected by using the tuberculin skin test or an interferon-gamma release assay. Within weeks after infection, the immune system is usually able to halt the multiplication of the tubercle bacilli, preventing further progression. In some people, the tubercle bacilli overcome the immune system and multiply, resulting in progression from LTBI to TB disease. The progression from LTBI to TB disease may occur at any time from Initial infection up to many years later. Without treatment, approximately 5% of individuals who have been infected with MTB will develop disease in the $1^{st}$ or $2^{nd}$ year after infection, and another 5% will develop the disease sometime later in life. Thus, without treatment, approximately 10% of individuals with normal immune systems, infected with MTB, will develop TB disease at some point in their lives.

Tuberculosis disease can occur in pulmonary (more than 60%) and extrapulmonary sites. Patients with pulmonary TB usually have a cough and an abnormal chest radiograph and can be infectious. Although the majority of TB cases are pulmonary, TB can occur in almost any anatomical site or as disseminated disease. Extrapulmonary TB disease occurs in places other than the lungs, including the larynx, the lymph nodes, the pleura, the brain, the kidneys, or the bones and joints.

Individuals with extrapulmonary TB disease are usually not infectious unless they also have pulmonary disease. Individuals with extrapulmonary TB disease are usually also not infectious unless the extrapulmonary disease is located in the oral cavity or the larynx, or the extrapulmonary disease includes an open abscess or lesion in which the concentration of organisms is high, especially if drainage from the abscess or lesion is extensive, or if drainage fluid is aerosolized. Individuals with TB pleural effusions may have underlying pulmonary TB that is masked on chest radiograph because the effusior fluid compresses the lung.

Miliary TB occurs when tubercle bacilli enter the bloodstream and disseminate to all parts of the body, where they grow and cause disease in multiple sites. This condition is rare but serious. It is most common in infants and children younger than 5 years of age, and in severely immunocompromised persons. Miliary TB can be detected in an individual organ, including the brain, in several organs, or throughout the whole body. The condition is characterized by a large amount of TB bacilli, which may easily be missed, and is fatal if untreated. Up to 25% of patients with miliary TB may have meningeal infection.

When TB occurs in the tissue surrounding the brain or spinal cord, it is called tuberculous meningitis. Tuberculous meningitis is often seen at the base of the brain on imaging studies. Symptoms include headache, decreased level of consciousness, and neck stiffness. The duration of illness before diagnosis is variable and relates in part to the presence or absence of other sites of involvement. In many cases, patients with meningitis have abnormalities on a chest radiograph consistent with old or current TB, and often have miliary TB.

Demographics of individuals with increased risk of progression of LTBI to TB are: human immunodeficiency virus (HIV)-infected individuals; children; individuals recently infected with MTB (<2 years); history of untreated or inadequately treated TB disease, including fibrotic changes on chest X-ray consistent with prior TB disease; individuals on immunosuppressive therapy (e.g., tumour necrosis factor-alpha antagonists, systemic corticosteroids [≥15 mg of prednisone per day]; individuals on immunosuppressive therapy following organ transplantation; silicosis; diabetes mellitus; chronic renal failure; leukemia; cancer of the head, neck, or lung; gastrectomy or jejunoileal bypass; low body mass index (BMI); cigarette smokers; drug and/or alcohol abusers; medically underserved, low-income populations.

Drug-resistant TB is caused by MTB microorganisms that are resistant to the drugs normally used to treat the disease. Drug-resistant TB is transmitted in the same way as drug-susceptible TB and is no more infectious than drug-susceptible TB. However, delay in the recognition of drug resistance or prolonged periods of infectiousness may facilitate increased transmission and further development of drug resistance.

Multidrug-resistant TB (MDR TB) is caused by microorganisms, resistant to the most effective anti-TB drugs, namely isoniazid and rifampin. These drugs are considered first-line drugs.

Extensively drug-resistant TB (XDR TB) is a relatively rare type of drug-resistant TB, Extensively drug-resistant TB is resistant to isoniazid and rifampin, plus any fluoroquinolone and at least one of three injectable second-line drugs, i.e., amikacin, kanamycin, or capreomycin. Because XDR TB is resistant to first-line and second-line drugs, patients are left with treatment options that are more toxic, more expensive, and much less effective.

The major goals of the treatment for TB disease are: to cure the individual patent; to minimize risk of death and disability and to reduce the transmission of MTB to others. To ensure the achievement of these goals. TB disease must be treated for at least 6 months and in some cases even longer. Most of the bacteria are killed during the first 8 weeks of treatment. However, there are persistent organisms that require longer treatment. If treatment is not continued for a duration that is long enough, the surviving bacteria may cause the patient to become ill and infectious again, potentially with drug-resistant strains of MTB. There are several options for daily and intermittent therapy, but the goal of treatment for TB disease should be to provide the safest and most effective therapy in the shortest period of time. Given adequate treatment, almost all patients will recover and be cured. Regimens for the treatment of TB disease must contain multiple drugs to which the bacteria are susceptible. The standard of care for initiating treatment of TB disease is four-drug therapy. Treatment with a single drug can lead to the development of a bacterial population resistant to that drug. Likewise, the addition of a single drug to a failing anti-TB regimen can lead to additional resistance. When two or more drugs to which in vitro susceptibility has been demonstrated are given together, each helps prevent the emergence of tubercle bacilli resistant to others.

There are several TB drug products approved for treatment of TB disease in the United States and in Europe. These drug products are classified as first-line drugs, for example isoniazid, rifampin, pyrazinamide, ethambutol, rifabutin, rifapentine; or second-line drugs, for example streptomycin, cycloserine, capreomycin, 4-aminosalicylic acid, levofloxacin, moxifloxacin, gatifloxacin, amikacin, kanamycin, ethionamide. Isoniazid, rifampin, pyrazinamide and ethambutol form the core of the initial treatment regimen for TB. Recently two new drug products were approved for treating MDR TB: bedaquiline and delamanid.

Rifabutin, approved for preventing *Mycobacterium avium* complex disease in patients with HIV infection but not approved for TB disease, is useful for treating TB disease in patients concurrently taking drugs that interact with rifampin (e.g., certain antiretroviral drugs). Amikacin and kanamycin, nearly identical aminoglycoside drugs used in treating patients with TB disease caused by drug-resistant organisms. Rifabutin and rifapentine may also be considered first-line drug products under certain circumstances. Streptomycin was formerly considered to be a first-line drug and, in some instances, is still used in the initial treatment regimen. However, an increasing prevalence of resistance to streptomycin in many parts of the world has decreased its overall usefulness. The remaining drugs are reserved for special situations such as drug intolerance or resistance.

There are four basic treatment regimens recommended for treating individuals with TB disease caused by tubercle bacilli that are known or presumed to be susceptible to isoniazid, rifampin, pyrazinamide and ethambutol. Each treatment regimen consists of an initial 2-month treatment phase followed by a continuation phase of either 4 or 7 months. The 4-month continuation phase is used for majority of the patients. Although these regimens are broadly applicable, there are modifications that should be made under specified circumstances.

The initial phase of treatment is crucial for preventing the emergence of drug resistance and determine the outcome of the regimen. Four drugs—isoniazid, rifampin, pyrazinamide and ethambutol—should be included in the initial treatment regimen until the results of drug-susceptibility tests are available. Each of the drugs in the initial regimen plays an important role. Isoniazid and rifampin allow for short-course regimens with high cure rates. Pyrazinamide has potent sterilizing activity which allows further shortening of the regimen from 9 to 6 months. Ethambutol helps to prevent the emergence of rifampin resistance when primary isoniazid resistance is present. It drug-susceptibility test results are known and the organisms are fully susceptible, ethambutol need not be included. For children, ethambutol is usually not recommended except when the risk of drug resistance is high or for children who have "adult-type" (upper lobe infiltration, cavity formation) TB disease.

The continuation phase of treatment is given for either 4 or 7 months. The 4-month continuation phase should be used in patients with uncomplicated, noncavitary, drug-susceptible TB, if there is documented sputum conversion within the first 2 months. The 7-month continuation phase is recommended for patients with cavitary or extensive pulmonary TB disease caused by drug-susceptible organisms and whose sputum culture obtained at the time of completion of 2 months of treatment is positive; and patients whose initial phase of treatment did not include pyrazinamide or patients being treated with once-weekly isoniazid and rifabutin and whose sputum culture at the time of completion of the initial phase (i.e., after 2 months) is positive.

In human immunodeficiency virus (HIV)-infected individuals, extrapulmonary TB disease is often accompanied by pulmonary TB. The treatment approach for patients co-infected with HIV and MTB is complex, and the clinical and public health consequences associated with the failure of treatment and other negative outcomes are serious. HIV-infected patients usually take several medicines and some of which interact with anti-TB drugs.

The treatment regimens mentioned above are effective for people living with HIV, with two exceptions due to increased risk of developing acquired drug resistance: once-weekly administration of isoniazid and rifabutin in the continuation phase should not be used in any HIV-infected patient; and patients with CD4+ lymphocytes counts <100 should be treated with daily or three times weekly therapy in both the initial and continuation phase. Every effort should be made to use a rifamycin-based regimen for the entire course of therapy in coinfected patients. The key role of the rifamycins in the success of TB disease treatment mandates that the drug-drug interactions between the rifamycins and antiretroviral drugs be managed appropriately, rather than using TB treatment regimens that do not include a rifamycin or by withholding antiretroviral therapy until completion of anti-TB therapy.

Of particular concern is the interaction of rifamycins with antiretroviral agents and other anti-Infective drugs. Rifampin can be used for the treatment of TB with certain combinations of antiretroviral agents. Rifabutin, which has fewer drug-drug interactions due to its decreased induction of the cytochrome P450 system, may also be used in place of rifampin and appears to be equally effective. Therefore, patients with HIV-related TB disease should be treated with a regimen including a rifamycin for the full course of TB disease treatment, unless the isolate is resistant to rifamycins or the patient has a severe side effect that is clearly due to rifamycins.

Six months should be considered the minimum duration of treatment for HIV-infected adults, even for patients with culture-negative TB disease. If there is evidence of a slow or suboptimal response (e.g., cultures are still positive after 2 months of therapy), the continuation phase should be prolonged to 7 months (a total of 9 months of treatment).

Drug-resistant TB disease can develop by two different mechanisms, primary and secondary drug resistance. Primary resistance occurs in persons who are initially exposed to and infected with resistant organisms. Secondary resistance, or acquired resistance, develops during TB therapy, either because the patient was treated with an inadequate regimen or because the patient did not take the prescribed regimen appropriately or because of other conditions such as drug malabsorption or drug-drug interactions leading to low serum levels.

Drug resistance in a patient with newly diagnosed TB disease is suspected on the basis of previous treatment, contact with a known drug-resistant case, or time spent in a region in which drug resistance is common. Drug resistance can be proven only by drug-susceptibility testing. Patients with strains of *M. tuberculosis* resistant to both isoniazid and rifampin (multidrug-resistant) are at high risk for treatment failure, relapse, further acquired resistance, or death.

Today's first-line antituberculosis therapy for drug-susceptible MTB infection is very effective in bacillary clearance, provided there is full compliance by the patient. It is important to note that despite having an effective treatment regimen, MTB still caused an estimated 10.4 million infections and 1.7 million deaths in 2017. Tuberculosis is one of the top 10 causes of death worldwide. About one-quarter of the world's population has latent TB. Those infected with TB bacteria have a 5-15% lifetime risk of falling ill with IB. However, patients with compromised immune systems, such as individuals living with HIV, malnutrition or diabetes, or tobacco users, have a much higher risk of falling ill (WHO, *WHO Global Tuberculosis Report* 2017, 2017).

Current front-line treatment consists of a 2 month 'intensive' period of a four drug regimen containing rifampicin (RIF), isoniazid (INH), pyrazinamide (PZA), and ethambutol (EMB) and is followed by a longer "continuation" phase of RIF and INH to eradicate the remaining bacilli that have entered a dormant, slowly replicating latent phase (Hoagland D T et al., *Adv Drug Deliv Rev.* 2016 Jul. 1, 102, 55-72).

The major concern of this epidemic is the emergence of resistant-bacteria, multidrug-resistant TB (MDR-TB) remains a public health crisis and a health security threat. WHO estimates that there were 600 000 new cases with resistance to rifampicin—the most effective first-line drug, of which 490 000 had MDR-TB (Hoagland D T et al., *Adv Drug Deliv Rev.* 2016 Jul. 1, 102, 55-72).

Quinolines are known in the art and have been used for tuberculosis. For example, document EP1527050B1 teaches the use of diarylquinoline in the treatment of mycobacterial diseases, in particular it discloses the first-in-class ATP synthase inhibitor Bedaquiline.

Document US2016113919A1 describes the use of Chloroquine stereoisomer for treating tuberculosis related diseases. Chloroquine belongs to the class of 4-aminoquinoline. 2-Aminoquinoline compounds are known in the art and have been used before in the pharmaceutical industry although for different purposes.

Document U.S. Pat. No. 7,868,022B2 describes 2-aminoquinoline compounds useful as inhibitor of beta-secretase (BACE) for the treatment of Alzheimer's disease (AD) and related diseases.

Document WO2012025237A9 describes 2-aminoquinoline compounds as modulators of KCNQ2/3 for the prophylaxis of pain.

Document U.S. Pat. No. 7,989,628B2 discloses 2-aminoquinolines derivatives as 5-HT5A receptor antagonists useful in the treatment of a range of CNS and PNS disorders.

Document WO2009001060A3 and journal article by Tantry, S. L. et al. (*Med. Chem. Commun.* 2016, 7, 1022-1032) disclose 2,4-diaminoquinolines as anti-tuberculosis agents. In particular they both describe examples of 4-amino-2-piperidinequinoline herein the piperidine and the quinoline aryl rings are not further substituted.

Document WO2017001661A1 relates to compounds for treatment of tuberculosis, herein the compounds have a 2-(4-(4-(trifluoromethoxy)phenyl)piperidin-1-yl)quinoline.

There is an urgent need for new and innovative treatment strategies to fight tuberculosis. Considerable progress has been made in TB drug discovery in the recent past years. A number of drug candidates are at different stages of clinical development, drugs such as diaryl quinolone (TMC207 or Bedaquiline) received expedited approval from the FDA for the treatment of MDR-TB; and Delamanid was approved by the European Union's European Medicines Agency (EMA). Both drugs have been conditionally approved because of adverse effects. The U.S. Food and Drug Agency (FDA) has approved Bedaquiline for MDR-TB and Delamanid as a compassionate care option for XDR-TB and TDR-TB infections, and the EMA approved both agents for MDR-TB. These are the two new drug therapies approved after 40 years. A lack of viable alternatives in late stage clinical development is indicative of the state of drug discovery in this field, and innovation to drive new projects is desperately needed.

These facts are disclosed in order to illustrate the technical problem addressed by the present disclosure.

GENERAL DESCRIPTION

The present disclosure relates to the use of 1-(quinolin-2-yl)piperidine-4-carboxylic acid compounds substituted with a 6-aryl or heteroaryl that can surprisingly be used for treating and/or preventing tuberculosis. None of the prior art documents disclose the use of said compounds for treatment of tuberculosis. In fact, the prior art documents that disclose compounds with a substituted 6-aryl or heteroaryl 1-(quinolin-2-yl)piperidine-4-carboxylic acid core all relate to different uses, and do not teach or suggest that these compounds might be used in the treatment of tuberculosis.

In an embodiment, the compounds disclosed in the present disclosure are used in the treatment of diseases caused by *Mycobacterium tuberculosis* (MTB) such as the case of pulmonary, extrapulmonary or disseminated tuberculosis (TB).

An aspect of the present disclosure relates to compound of general formula I or a pharmaceutically acceptable salt, hydrate, solvate. N-oxide, stereoisomer, diastereoisomer, enantiomer or atropisomer, polymorph or ester thereof:

Formula I wherein $R_1$, $R_2$, X, Y, Z, W, are independently selected from each other;

$R_1$ is selected from H or $C_1$-$C_6$ alkyl;

$R_2$ is selected from H or $C_1$-$C_6$ alkyl;

X is selected from N, O, S or $CR_3$, and $R_3$ is selected from H, halogen, $C_1$-$C_6$ alkoxy or $C_1$-$C_6$ haloalkyl;

Y is selected from N or $CR_4$, and $R_4$ is selected from H, $C_1$-$C_6$ haloalkoxy, OH, $C_1$-$C_6$ alkoxy, $C_1$-$C_6$ haloalkyl, halogen or $C_1$-$C_6$ alkyl;

Z is selected from N or $CR_5$, and $R_5$ is selected from H, halogen, $C_1$-$C_6$ alkoxy, $C_1$-$C_6$ haloalkyl, $C_1$-$C_6$ haloalkoxy, OH, $NO_2$ or $C_1$-$C_6$ alkyl;

W is selected from N, or $CR_6$, and $R_6$ is selected from H, $C_1$-$C_6$ alkoxy, $C_1$-$C_6$ haloalkyl, halogen, or $C_1$-$C_6$ haloalkoxy;

m and n are independently selected from 0 or 1;

halogen is F or Cl;

with the proviso that the group connected to the quinoline moiety on $C_6$ is a substituted aryl, a substituted or unsubstituted heteroaryl or fused heteroaroaryl ring selected from pyridin-2-yl, pyridin-3-yl, pyridin-4-yl, pyrimidin-5-yl, furan-2-yl, benzothiophenyl, indolyl or phenyl, and the piperidine ring that is connected to the quinoline moiety on $C_2$, has its $C_3$ or $C_4$ substituted with carboxylate group.

In the context of the present disclosure the numbering of the quinoline is made according to the IUPAC rules (formula V)

Formula V

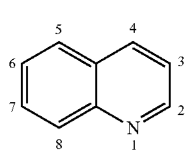

In an embodiment, the compound is represented by compound of Formula I wherein:

Formula I

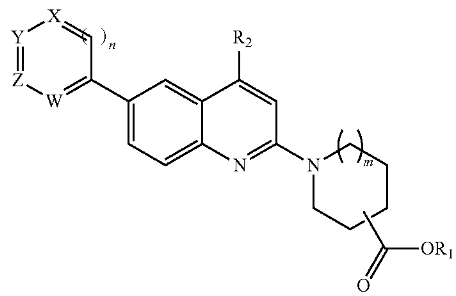

R1 is selected from H, $CH_2CH_3$ or $CH_3$;

R2 is selected from H or $CH_3$;

X is selected from N, O, S or $CR_3$, and $R_3$ is selected from H, Cl, F, $CF_3$ or $OCH_3$;

Y is selected from N or $CR_4$, and $R_4$ is selected from H, F, Cl, $CH_3$, OH, $CF_3$, $OCF_3$, $OCH(CH_3)_2$ or $OCH_3$;

Z is selected from N or $CR_5$, and $R_5$ is H, OH, F, $OCF_3$, $OCH_3$, $NO_2$, $CF_3$ or $CH_3$;

W is selected from N or $CR_6$ and $R_6$ is H, F, Cl, $CF_3$, $OCH_3$ or $OCF_3$;

m and n are independently selected from 0 or 1;

with the proviso that the group connected to the quinoline moiety on $C_6$ is a substituted aryl, a substituted or unsubstituted heteroaryl or fused heteroaroaryl ring selected from pyridin-2-yl, pyridin-3-yl, pyridin-4-yl, pyrimidin-5-yl, furan-2-yl, benzothiophenyl, indolyl or phenyl.

In an embodiment, the compound is represented by compound of Formula II wherein:

Formula II 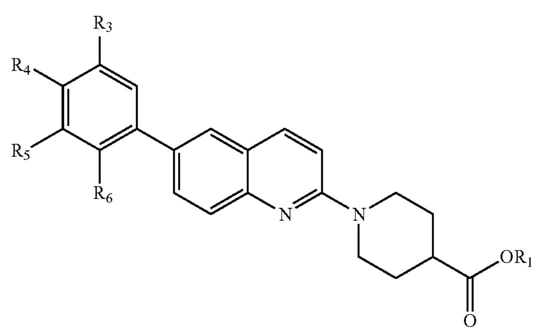 $R_1$ is selected from H or $CH_2CH_3$;

$R_3$ is selected from H, Cl, F, $CF_3$ or $OCH_3$;

$R_4$ is selected from H, OH, Cl, F, $OCF_3$, $CH_3$, $CF_3$, $OCH(CH_3)_2$ or $OCH_3$;

$R_5$ is selected from H, OH, F, $OCF_3$, $CF_3$, $CH_3$, $OCH_3$ or $NO_2$;

$R_6$ is selected from H, Cl, F, $CF_3$ or $OCF_3$ or $OCH_3$;

with the proviso that the group connected to the quinoline moiety on $C_6$ is a substituted aryl, substituted or unsubstituted heteroaryl or fused heteroaroaryl ring selected from indolyl or phenyl.

In an embodiment, for the compound of Formula II, $R_3$ is H, Cl, F or $CF_3$.

In an embodiment, for the compound of Formula II, $R_4$ is H, Cl, F, $OCF_3$, $OCH(CH_3)_2$ or $OCH_3$.

In an embodiment, for the compound of Formula II, $R_5$ is H, Cl, F, OH, $OCF_3$ or $CF_3$.

In an embodiment, for the compound of Formula II, $R_6$ is H, Cl, $CF_3$ or $OCH_3$.

In an embodiment, the compound is represented by compound of Formula III wherein:

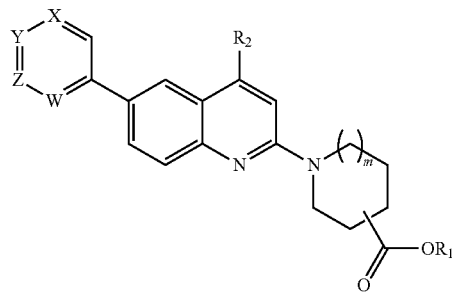

Formula III

R1 is selected from H, $CH_2CH_3$ or $CH_3$;

R2 is selected from H and $CH_3$;

X is selected from N, or $CR_3$, and $R_3$ is H;

Y is selected from N or $CR_4$, and $R_4$ is selected from H, $CH_3$, F, $CF_3$ or $OCH_3$;

Z is selected from N or $CR_5$, and $R_5$ is selected from H or $CH_3$;

W is selected from N or $CR_6$, and $R_6$ is selected from H or F;

m is selected from 0 or 1;

with the proviso that the group connected to the quinoline moiety on $C_6$ is a substituted aryl, substituted or unsubstituted heteroaryl or fused heteroaroaryl ring selected from pyridin-2-yl, pyridin-3-yl, pyridin-4-yl or pyrimidin-5-yl.

In an embodiment, for the compound of Formula III, where X and Z are both N, $R_5$ is $OCH_3$.

In an embodiment, for the compound of Formula III, Y, Z or W is N.

In an embodiment, for the compound of Formula III, Y is N.

In an embodiment, for the compound of Formula III: when Z is N, $R_4$ is $OCH_3$.

In an embodiment, for the compound of Formula III: when Z is N, $R_4$ is $CH_3$.

In an embodiment, for the compound of Formula III, W is N.

In an embodiment, the compound is represented by compound of Formula IV wherein:

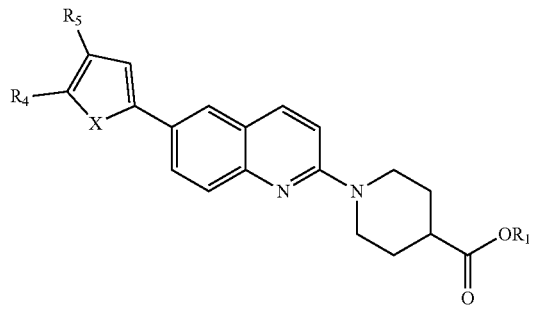

Formula IV

X is O or S;

R1 is selected from H or $CH_2CH_3$;

with the proviso that the group connected to the quinoline moiety on $C_6$ is a substituted or unsubstituted aryl, heteroaryl or fused heteroaroaryl ring selected from furan-2-yl or benzothiophenyl.

In an embodiment, for compounds of Formula II, III and IV, $R_1$ is H or $CH_2CH_3$.

In an embodiment, for compounds of Formula I, II, III and IV, the salt is a hydrochloride.

In an embodiment, the compound is selected from:

Ethyl 1-(6-(4-(trifluoromethoxy)phenyl)quinolin-2-yl)piperidine-4-carboxylate;

1-(6-(4-(Trifluoromethoxy)phenyl)quinolin-2-yl)piperidine-4-carboxylic acid;

Ethyl 1-(6-(4-hydroxyphenyl)quinolin-2-yl)piperidine-4-carboxylate;

Ethyl 1-(6-(2-methoxypyrimidin-5-yl)quinolin-2-yl)piperidine-4-carboxylate;

Ethyl 1-(6-(4-isopropoxyphenyl)quinolin-2-yl)piperidine-4-carboxylate;

1-(6-(2-Methoxypyrimidin-5-yl)quinolin-2-yl)piperidine-4-carboxylic acid;

1-(6-(4-Isopropoxyphenyl)quinolin-2-yl)piperidine-4-carboxylic acid;

Ethyl 1-(6-(3-fluorophenyl)quinolin-2-yl)piperidine-4-carboxylate;

1-(6-(4-Hydroxyphenyl)quinolin-2-yl)piperidine-4-carboxylic acid;

1-(6-(3-Fluoro-4-isopropoxyphenyl)quinolin-2-yl)piperidine-4-carboxylic acid;

1-(6-(3-Fluorophenyl)quinolin-2-yl)piperidine-4-carboxylic acid;

Ethyl 1-(6-(3-fluoro-4-isopropoxyphenyl)quinolin-2-yl)piperidine-4-carboxylate;

1-(6-(6-Methoxypyridin-3-yl)quinolin-2-yl)piperidine-4-carboxylic acid;

Ethyl 1-(6-(6-methoxypyridin-3-yl)quinolin-2-yl)piperidine-4-carboxylate;

Ethyl 1-(6-(pyridin-4-yl)quinolin-2-yl)piperidine-4-carboxylate hydrochloride;

Ethyl 1-(6-(furan-2-yl)quinolin-2-yl)piperidine-4-carboxylate;

1-(6-(Furan-2-yl)quinolin-2-yl)piperidine-4-carboxylic acid;

1-(6-(Pyridin-4-yl)quinolin-2-yl)piperidine-4-carboxylic acid hydrochloride;

Ethyl 1-(6-(2-chloro-4-methoxyphenyl)quinolin-2-yl)piperidine-4-carboxylate;

Ethyl 1-(6-(4-methoxyphenyl)quinolin-2-yl)piperidine-4-carboxylate;

1-(6-(4-Methoxyphenyl)quinolin-2-yl)piperidine-4-carboxylic acid;
1-(6-(3-Methoxyphenyl)quinolin-2-yl)piperdine-4-carboxylic acid;
1-(6-(2-Chloro-4-methoxyphenyl)quinolin-2-yl)piperidine-4-carboxylic acid;
Ethyl 1-(6-(4-methoxy-2-(trifluoromethyl)phenyl)quinolin-2-yl)piperidine-4-carboxylate hydrochloride;
Ethyl 1-(6-(3-(trifluoromethoxy)phenyl)quinolin-2-yl)piperidine-4-carboxylate;
Ethyl 1-(6-(3-hydroxyphenyl)quinolin-2-yl)piperidine-4-carboxylate;
1-(6-(3-Hydroxyphenyl)quinolin-2-yl)piperidine-4-carboxylic acid;
1-(6-(4-Methoxy 2 (trifluoromethyl)phenyl)quinolin 2 yl)piperidine 4 carboxylic acid;
1-(6-(3-(Trifluoromethoxy)phenyl)quinolin-2-yl)piperidine-4-carboxylic acid;
Ethyl 1-(6-(3-methoxyphenyl)quinolin-2-yl)piperidine-4-carboxylate;
Ethyl 1-(6-(4-(trifluoromethyl)phenyl)quinolin-2-yl)piperidine-4-carboxylate;
Ethyl 1-(6-(3-nitrophenyl)quinolin-2-yl)piperidine-4-carboxylate;
Ethyl 1-(6-(4-fluorophenyl)quinolin-2-yl)piperidine-4-carboxylate;
Ethyl 1-(6-(pyridin-3-yl)quinolin-2-yl)piperidine-4-carboxylate;
Ethyl 1-(6-(6-fluoropyridin-3-yl)quinolin-2-yl)piperidine-4-carboxylate;
1-(6-(4-(Trifluoromethyl)phenyl)quinolin-2-yl)piperidine-4-carboxylic acid;
Ethyl 1-(6-(2-fluoropyridin-4-yl)quinolin-2-yl)piperidine-4-carboxylate;
1-(6-(6-Fluoropyridin-3-yl)quinolin-2-yl)piperidine-4-carboxylic acid hydrochloride;
1-(6-(3-Nitrophenyl)quinolin-2-yl)piperidine-4-carboxylic acid;
Ethyl 1-(6-(2-methylpyridin-4-yl)quinolin-2-yl)piperidine-4-carboxylate;
Ethyl 1-(6-(3,5-dimethoxyphenyl)quinolin-2-yl)piperidine-4-carboxylate;
Ethyl 1-(6-(1H-indol-5-yl)quinolin-2-yl)piperidine-4-carboxylate;
Ethyl 1-(6-(6-(trifluoromethyl)pyridin-3-yl)quinolin-2-yl)piperidine-4-carboxylate;
Ethyl 1-(6-(pyrimidin-5-yl)quinolin-2-yl)piperidine-4-carboxylate;
1-(6-(1H-Indol-5-yl)quinolin-2-yl)piperidine-4-carboxylic acid hydrochloride;
1-(6-(3,5-Dimethoxyphenyl)quinolin-2-yl)piperidine-4-carboxylic acid;
1-(6-(4-Fluorophenyl)quinolin-2-yl)piperidine-4-carboxylic acid;
1-(6-(Pyrimidin-5-yl)quinolin-2-yl)piperidine-4-carboxylic acid;
1-(6-(Pyridin-3-yl)quinolin-2-yl)piperidine-4-carboxylic acid;
Ethyl 1-(6-(6-methylpyridin-3-yl)quinolin-2-yl)piperidine-4-carboxylate;
1-(6-(2-Fluoropyridin-4-yl)quinolin-2-yl)piperidine-4-carboxylic acid hydrochloride;
1-(6-(6-(Trifluoromethyl)pyridin-3-yl)quinolin-2-yl)piperidine-4-carboxylic acid hydrochloride;
1-(6-(2-Methylpyridin-4-yl)quinolin-2-yl)piperidine-4-carboxylic acid;
Ethyl 1-(6-(pyridin-4-yl)quinolin-2-yl)piperidine-3-carboxylate;
Ethyl 1-(6-(pyridin-2-yl)quinolin-2-yl)piperidine-4-carboxylate;
1-(4-Methyl-6-(pyridin-4-yl)quinolin-2-yl)piperidine-4-carboxylic acid;
Ethyl 1-(4-methyl-6-(pyridin-4-yl)quinolin-2-yl)piperidine-4-carboxylate;
Ethyl 1-(6-(3-fluoro-4-methoxyphenyl)quinolin-2-yl)piperidine-4-carboxylate;
Ethyl 1-(6-(3-chloro-4-methoxyphenyl)quinolin-2-yl)piperidine-4-carboxylate;
ethyl 1-(6-(3,4-dimethoxyphenyl)quinolin-2-yl)piperidine-4-carboxylate;
1-(6-(Pyridin-2-yl)quinolin-2-yl)piperidine-4-carboxylic acid;
1-(6-(Pyridin-4-yl)quinolin-2-yl)piperidine-3-carboxylic acid hydrochloride;
Ethyl 1 (6 (4 chloro 3 fluorophenyl)quinolin 2 yl)piperidine 4 carboxylate;
Ethyl 1-(6-(3-chlorophenyl)quinolin-2-yl)piperidine-4-carboxylate;
Ethyl 1-(6-(4-chlorophenyl)quinolin-2-yl)piperidine-4-carboxylate;
Ethyl 1-(6-(3-(trifluoromethyl)phenyl)quinolin-2-yl)piperidine-4-carboxylate;
Ethyl 1-(6-(pyridin-4-yl)quinolin-2-yl)pyrrolidine-3-carboxylate;
Ethyl 1-(6-(benzo[b]thiophen-2-yl)quinolin-2-yl)piperidine-4-carboxylate;
Ethyl 1-(6-(2-(trifluoromethyl)phenyl)quinolin-2-yl)piperidine-4-carboxylate;
Ethyl 1-(6-(2-(trifluoromethoxy)phenyl)quinolin-2-yl)piperidine-4-carboxylate;
Ethyl 1-(6-(4-fluoro-2-methoxyphenyl)quinolin-2-yl)piperidine-4-carboxylate;
Ethyl 1-(6-(4-methoxy-3-(trifluoromethyl)phenyl)quinolin-2-yl)piperidine-4-carboxylate;
Ethyl 1-(6-(4-chloro-3-methoxyphenyl)quinolin-2-yl)piperidine-4-carboxylate;
Ethyl 1-(6-(3-chloro-4-fluorophenyl)quinolin-2-yl)piperidine-4-carboxylate;
Ethyl 1-(6-(2-methoxypyridin-3-yl)quinolin-2-yl)piperidine-4-carboxylate;
Ethyl 1-(6-(S-fluoropyridin-3-yl)quinolin-2-yl)piperidine-4-carboxylate;
Ethyl 1-(6-(3-fluoropyridin-4-yl)quinolin-2-yl)piperidine-4-carboxylate;
Methyl 1-(6-(pyridin-4-yl)quinolin-2-yl)piperidine-4-carboxylate; or
1-(6-(6-methylpyridin-3-yl)quinolin-2-yl)piperidine-4-carboxylic acid hydrochloride.

In an embodiment, the compound is selected from:
1-(6-(4-(trifluoromethoxy)phenyl)quinolin-2-yl)piperidine-4-carboxylic acid;
ethyl 1-(6-(2-methoxypyrimidin-5-yl)quinolin-2-yl)piperidine-4-carboxylate;
ethyl 1-(6-(3-fluorophenyl)quinolin-2-yl)piperidine-4-carboxylate;
1-(6-(3-fluoro-4-isopropoxyphenyl)quinolin-2-yl)piperidine-4-carboxylic acid;
1-(6-(3-fluorophenyl)quinolin-2-yl)piperidine-4-carboxylic acid;
ethyl 1-(6-(6-methoxypyridin-3-yl)quinolin-2-yl)piperidine-4-carboxylate;
ethyl 1-(6-(2-chloro-4-methoxyphenyl)quinolin-2-yl)piperidine-4-carboxylate;

1-(6-(4-methoxyphenyl)quinolin-2-yl)piperidine-4-carboxylic acid;
ethyl 1-(6-(4-methoxy-2-(trifluoromethyl)phenyl)quinolin-2-yl)piperidine-4-carboxylate hydrochloride;
ethyl 1-(6-(3-(trifluoromethoxy)phenyl)quinolin-2-yl)piperidine-4-carboxylate;
ethyl 1-(6-(3-hydroxyphenyl)quinolin-2-yl)piperidine-4-carboxylate;
1-(6-(3-(trifluoromethoxy)phenyl)quinolin-2-yl)piperidine-4-carboxylic acid;
ethyl 1-(6-(6-methylpyridin-3-yl)quinolin-2-yl)piperidine-4-carboxylate;
ethyl 1-(6-(pyridin-2-yl)quinolin-2-yl)piperidine-4-carboxylate;
ethyl 1-(b-(3-fluoro-4-methoxyphenyl)quinolin-2-yl)piperidine-4-carboxylate;
ethyl 1-(6-(4-chloro-3-fluorophenyl)quinolin-2-yl)piperidine-4-carboxylate;
ethyl 1-(6-(2-(trifluoromethyl)phenyl)quinolin-2-yl)piperidine-4-carboxylate; or
ethyl 1-(6-(4-fluoro-2-methoxyphenyl)quinolin-2-yl)piperidine-4-carboxylate.

Another aspect of the present disclosure relates to a pharmaceutical composition comprising the compounds of the present disclosure and a pharmaceutical acceptable excipient. Preferably, a therapeutically effective amount of the compounds described in the present disclosures or a pharmaceutically acceptable salt or solvate thereof; and a pharmaceutically acceptable excipient.

Another aspect of the present disclosure relates to compound of general formula XII or a pharmaceutically acceptable salt, hydrate, solvate, N-oxide, stereoisomer, diastereoisomer, enantiomer or atropisomer, polymorph or ester thereof:

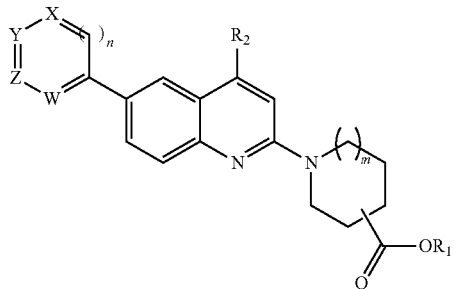

Formula XII wherein
$R_1$ is selected from H or $C_1$-$C_6$ alkyl;
$R_2$ is selected from H or $C_1$-$C_6$ alkyl;
X is selected from N, O, S or $CR_3$, and $R_3$ is selected from H, $C_1$-$C_6$ alkoxy or $C_1$-$C_6$ haloalkyl;
Y is selected from N or $CR_4$, and $R_4$ is selected from H, $C_1$-$C_6$ haloalkoxy, OH, $C_1$-$C_6$ alkoxy, $C_1$-$C_6$ haloalkyl, halogen or $C_1$-$C_6$ alkyl;
Z is selected from N or $CR_5$, and $R_5$ is selected from H, halogen, $C_1$-$C_6$ alkoxy, $C_1$-$C_6$ haloalkoxy, OH, $NO_2$ or $C_1$-$C_6$ alkyl;
W is selected from N, or $CR_6$, and $R_6$ is selected from H, $C_1$-$C_6$ haloalkyl, halogen or $C_1$-$C_6$ haloalkoxy;
m and n are independently selected from 0 or 1;
wherein the halogen is F or Cl;
with the proviso that when n is 0, X is O or S to form a furyl or thiophene respectively;
Y and Z together with the thiophene they are attached can form a benzothiophene; or
Y and Z together with the benzene ring they are attached can form an indole ring.

In an embodiment for better results, the compound is represented by compound of Formula XII wherein:
$R_1$ is selected from H, $CH_2CH_3$ or $CH_3$;
$R_2$ is selected from H or $CH_3$;
X is selected from N, O, S or $CR_3$, and $R_3$ is selected from H or $OCH_3$;
Y is selected from N or $CR_4$, and $R_4$ is selected from H, OH, $OCF_3$, $OCH(CH_3)b$ or $OCH_3$;
Z is selected from N or $CR_5$, and $R_5$ is H, F, $OCF_3$, $OCH_3$, $NO_2$ or $CH_3$;
W is selected from N or $CR_6$ and $R_6$ is H, Cl or $CF_3$;
m and n are independently selected from 0 or 1;
with the proviso that when n is 0, X is O or S to form a furyl or thiophene respectively; and
Y and Z together with the thiophene they are attached can form a benzothiophene; or
Y and Z together with the benzene ring they are attached can form an indole ring.

In an embodiment for better results, the compound is represented by compound of Formula XIII

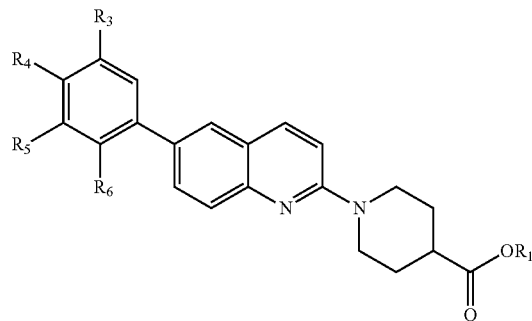

Formula XIII $R_1$ is selected from H or $CH_2CH_3$;
$R_3$ is selected from H or $OCH_3$;
$R_4$ is selected from H, OH, Cl, F, $OCF_3$, $CF_3$, $OCH(CH_3)_2$ or $OCH_3$;
$R_5$ is selected from H, OH, Cl, F, $OCF_3$, $CF_3$, $OCH_3$ or $NO_2$;
$R_6$ is selected from H, Cl, $CF_3$ or $OCF_3$;
$R_4$ and $R_5$ together with the carbon they are attached can form an indole ring.

In an embodiment for better results, the compound is represented by compound of Formula XIV

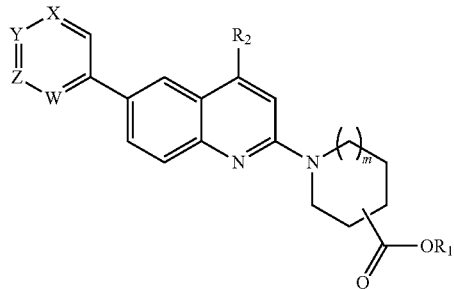

Formula XIV $R_1$ is selected from H, $CH_2CH_3$ or $CH_3$;
$R_2$ is selected from H or $CH_3$;
X is selected from N, or $CR_3$, and $R_3$ is selected from H or $OCH_3$;
Y is selected from N or $CR_4$, and $R_4$ is selected from H, $CH_3$, F, $OCF_3$, $CF_3$, $OCH(CH_3)_2$ or $OCH_3$;
Z is selected from N or $CR_5$, and $R_5$ is selected from H or $CH_3$;
W is selected from N or $CR_6$, and $R_6$ is selected from H or F;
m is selected from 0 or 1.

In an embodiment for better results, the compound is represented by compound of Formula XV

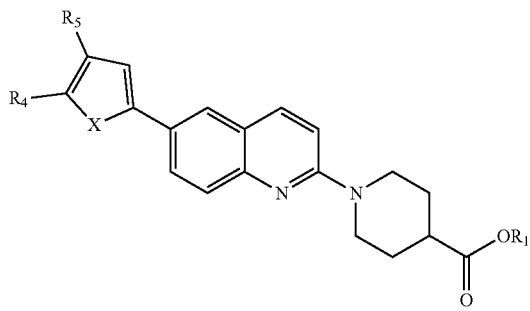

Formula XV

X is O or S;
$R_1$ is selected from H or $CH_2CH_3$;
$R_4$ and $R_5$ together with the carbon they are attached can form a benzene ring.

In an embodiment for better results, compound of general formula XVI or a pharmaceutically acceptable salt, hydrate, solvate, N-oxide, stereoisomer, diastereoisomer, enantiomer or atropisomer, polymorph or ester thereof:

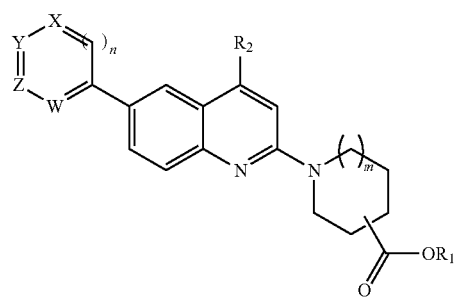

Formula XVI wherein
R1, R2, X, Y, Z, W, are independently selected from each other;
R1 is selected from H or C1-C6 alkyl;
R2 is selected from H or C1-C6 alkyl;
X is selected from N, O, S or CR3, and R3 is selected from H, C1 C6 alkoxy or C1 C6 haloalkyl;
Y is selected from N or CR4, and R4 is selected from H, C1-C6 haloalkoxy, OH, C1-C6 alkoxy, C1-C6 haloalkyl, halogen or C1-C6 alkyl;
Z is selected from N or CR5, and R5 is selected from H, halogen, C1-C6 alkoxy, C1-C6 haloalkoxy, OH, NO2 or C1-C6 alkyl;
W is selected from N, or CR6, and R6 is selected from H, C1-C6 haloalkyl, halogen or C1-C6 haloalkoxy;
m and n are independently selected from 0 or 1;
wherein the halogen is F or Cl;
with the proviso that the group connected to the quinoline moiety on C6 is a substituted or unsubstituted aromatic, heteroaromatic or fused heteroaromatic ring selected from pyridin-3-yl, pyridin-4-yl, pyrimidin-5-yl, furan-2-yl, benzothiophenyl, indolyl or phenyl.

In an embodiment for better results, the compound is represented by compound of Formula XVI $R_1$ is selected from H, $CH_2CH_3$ or $CH_3$;
$R_2$ is selected from H or $CH_3$;
X is selected from N, O, S or $CR_3$, and $R_3$ is selected from H or $OCH_3$;
Y is selected from N or $CR_4$, and $R_4$ is selected from H, OH, $OCF_3$, $OCH(CH_3)_2$ or $OCH_3$;
Z is selected from N or $CR_5$, and $R_5$ is H, F, $OCF_3$, $OCH_3$, $NO_2$ or $CH_3$;
W is selected from N or $CR_6$ and $R_6$ is H, Cl or $CF_3$;
m and n are independently selected from 0 or 1;
with the proviso that the group connected to the quinoline moiety on $C_6$ is a substituted or unsubstituted aromatic, heteroaromatic or fused heteroaromatic ring selected from pyridin-3-yl, pyridin-4-yl, pyrimidin-5-yl, furan-2-yl, benzothiophenyl, indolyl or phenyl.

In an embodiment for better results, compound is represented by compound of Formula XVII

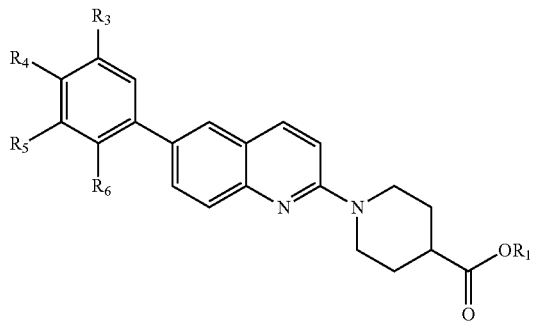

Formula XVII $R_1$ is selected from H or $CH_2CH_3$;
$R_3$ is selected from H or $OCH_3$;
$R_4$ is selected from H, OH, Cl, F, $OCF_3$, $CF_3$, $OCH(CH_3)_2$ or $OCH_3$;
$R_5$ is selected from H, OH, Cl, F, $OCF_3$, $CF_3$, $OCH_3$ or $NO_2$;
$R_6$ is selected from H, Cl, $CF_3$ or $OCF_3$;
with the proviso that the group connected to the quinoline moiety on $C_6$ is a substituted or unsubstituted aromatic, heteroaromatic or fused heteroaromatic ring selected from indolyl or phenyl.

In an embodiment for better results, compound is represented by compound of Formula XVIII Formula XVIII

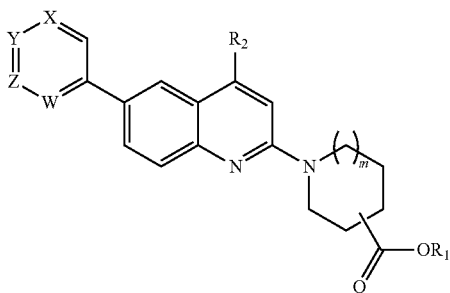

R₁ is selected from H, CH₂CH₃ or CH₃,
R₂ is selected from H or CH₃;
X is selected from N, or CR₃, and R₃ is selected from H or OCH₃;
Y is selected from N or CR₄, and R₄ is selected from H, CH₃, F, OCF₃, CF₃, OCH(CH₃)₂ or OCH₃;
Z is selected from N or CR₅, and R₅ is selected from H or CH₃;
W is selected from N or CR₆, and R₆ is selected from H or F;
m is selected from 0 or 1;
with the proviso that the group connected to the quinoline moiety on $C_b$ is a substituted or unsubstituted aromatic, heteroaromatic or fused heteroaromatic ring selected from pyridin-3-yl, pyridin-4-yl or pyrimidin-5-yl.

In an embodiment for better results, compound is represented by compound of Formula XIX Formula XIX

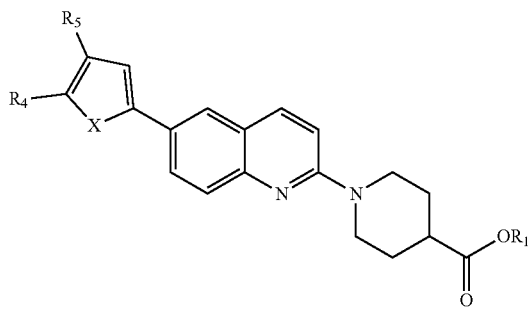

X is O or S;
R1 is selected from H or CH₂CH₃,
with the proviso that the group connected to the quinoline moiety on $C_6$ is a substituted or unsubstituted aromatic, heteroaromatic or fused heteroaromatic ring selected from furan-2-yl or benzothiophenyl.

In an embodiment, for the compound of Formula XVII: Y is N.

In an embodiment, for the compound of Formula XVII: R₂, R₃, R₆ are H; and R₁ is H or CH₂CH₃.

In an embodiment, for the compound of Formula XVII: X is N and Z is CH.

In an embodiment, for the compound of Formula XVII: R₄ is CH₃ or OCH₃.

In an embodiment, for the compound of Formula XVIII: R₄ is OCH₃ or OCF₃.

In an embodiment, for the compound of Formula XVIII: R₅ is OH, F or OCF₃, preferably R₅ is OCF₃.

In an embodiment, for the compound of Formula XVIII: R₆ is Cl or CF₃, preferably R₆ is CF₃.

In an embodiment, for the compounds of Formula XVI or Formula XVII or Formula XVIII or Formula XIX: the salt is hydrochloride.

In an embodiment, the compound is:
Ethyl 1-(6-(4-(trifluoromethoxy)phenyl)quinolin-2-yl)piperidine-4-carboxylate;
1-(6-(4-(Trifluoromethoxy)phenyl)quinolin-2-yl)piperidine-4-carboxylic acid;
Ethyl 1-(6-(4-hydroxyphenyl)quinolin-2-yl)piperidine-4-carboxylate;
Ethyl 1-(6-(2-methoxypyrimidin-5-yl)quinolin-2-yl)piperidine-4-carboxylate;
Ethyl 1-(6-(4-isopropoxyphenyl)quinolin-2-yl)piperidine-4-carboxylate;
1-(6-(2-Methoxypyrimidin-5-yl)quinolin-2-yl)piperidine-4-carboxylic acid;
1-(6-(4-Isopropoxyphenyl)quinolin-2-yl)piperidine-4-carboxylic acid;
Ethyl 1-(6-(3-fluorophenyl)quinolin-2-yl)piperidine-4-carboxylate;
1-(6-(4-Hydroxyphenyl)quinolin-2-yl)piperidine-4-carboxylic acid;
1-(6-(3-Fluoro-4-isopropoxyphenyl)quinolin-2-yl)piperidine-4-carboxylic acid;
1-(6-(3-Fluorophenyl)quinolin-2-yl)piperidine-4-carboxylic acid;
Ethyl 1-(6-(3-fluoro-4-isopropoxyphenyl)quinolin-2-yl)piperidine-4-carboxylate;
1-(6-(6-Methoxypyridin-3-yl)quinolin-2-yl)piperidine-4-carboxylic acid;
Ethyl 1-(6-(6-methoxypyridin-3-yl)quinolin-2-yl)piperidine-4-carboxylate;
Ethyl 1-(6-(pyridin-4-yl)quinolin-2-yl)piperidine-4-carboxylate hydrochloride;
Ethyl 1-(6-(furan-2-yl)quinolin-2-yl)piperidine-4-carboxylate;
1-(6-(Furan-2-yl)quinolin-2-yl)piperidine-4-carboxylic acid;
1-(6-(Pyridin-4-yl)quinolin-2-yl)piperidine-4-carboxylic acid hydrochloride;
Ethyl 1-(6-(2-chloro-4-methoxyphenyl)quinolin-2-yl)piperidine-4-carboxylate;
Ethyl 1-(6-(4-methoxyphenyl)quinolin-2-yl)piperidine-4-carboxylate;
1-(6-(4-Methoxyphenyl)quinolin-2-yl)piperidine-4-carboxylic acid;
1-(6-(3-Methoxyphenyl)quinolin-2-yl)piperidine-4-carboxylic acid;
1-(6-(2-Chloro-4-methoxyphenyl)quinolin-2-yl)piperidine-4-carboxylic acid;
Ethyl 1-(6-(4-methoxy-2-(trifluoromethyl)phenyl)quinolin-2-yl)piperidine-4-carboxylate hydrochloride;
Ethyl 1-(6-(3-(trifluoromethoxy)phenyl)quinolin-2-yl)piperidine-4-carboxylate;
Ethyl 1-(6-(3-hydroxyphenyl)quinolin-2-yl)piperidine-4-carboxylate;
1-(6-(3-Hydroxyphenyl)quinolin-2-yl)piperidine-4-carboxylic acid;
1-(6-(4-Methoxy-2-(trifluoromethyl)phenyl)quinolin-2-yl)piperidine-4-carboxylic acid;
1-(6-(3-(Trifluoromethoxy)phenyl)quinolin-2-yl)piperidine-4-carboxylic acid;
Ethyl 1-(6-(3-methoxyphenyl)quinolin-2-yl)piperidine-4-carboxylate;

Ethyl 1-(6-(4-(trifluoromethyl)phenyl)quinolin-2-yl)piperidine-4-carboxylate;
Ethyl 1-(6-(3-nitrophenyl)quinolin-2-yl)piperidine-4-carboxylate;
Ethyl 1-(6-(4-fluorophenyl)quinolin-2-yl)piperidine-4-carboxylate;
Ethyl 1-(6-(pyridin-3-yl)quinolin-2-yl)piperidine-4-carboxylate;
Ethyl 1-(6-(6-fluoropyridin-3-yl)quinolin-2-yl)piperidine-4-carboxylate;
1-(6-(4-(Trifluoromethyl)phenyl)quinolin-2-yl)piperidine-4-carboxylic acid;
Ethyl 1-(6-(2-fluoropyridin-4-yl)quinolin-2-yl)piperidine-4-carboxylate;
1-(6-(6-Fluoropyridin-3-yl)quinolin-2-yl)piperidine-4-carboxylic acid hydrochloride;
1-(6-(3-Nitrophenyl)quinolin-2-yl)piperidine-4-carboxylic acid;
Ethyl 1-(6-(2-methylpyridin-4-yl)quinolin-2-yl)piperidine-4-carboxylate;
Ethyl 1-(6-(3,5-dimethoxyphenyl)quinolin-2-yl)piperidine-4-carboxylate;
Ethyl 1-(6-(1H-indol-5-yl)quinolin-2-yl)piperidine-4-carboxylate;
Ethyl 1-(6-(6-(trifluoromethyl)pyridin-3-yl)quinolin-2-yl)piperidine-4-carboxylate;
Ethyl 1-(6-(pyrimidin-5-yl)quinolin-2-yl)piperidine-4-carboxylate;
1-(6-(1H-Indol-5-yl)quinolin-2-yl)piperidine-4-carboxylic acid hydrochloride;
1-(6-(3,5-Dimethoxyphenyl)quinolin-2-yl)piperidine-4-carboxylic acid;
1-(6-(4-Fluorophenyl)quinolin-2-yl)piperidine-4-carboxylic acid;
1-(6-(Pyrimidin-5-yl)quinolin-2-yl)piperidine-4-carboxylic acid;
1-(b-(Pyridin-3-yl)quinolin-2-yl)piperidine-4-carboxylic acid;
Ethyl 1-(6-(6-methylpyridin-3-yl)quinolin-2-yl) piperidine-4-carboxylate;
1-(6-(2-Fluoropyridin-4-yl)quinolin-2-yl)piperidine-4-carboxylic acid hydrochloride;
1 (6 (6 (Trifluoromethyl)pyridin 3 yl)quinolin 2 yl)piperidine 4 carboxylic acid hydrochloride;
1-(6-(2-Methylpyridin-4-yl)quinolin-2-yl)piperidine-4-carboxylic acid;
Ethyl 1-(6-(pyridin-4-yl)quinolin-2-yl) piperidine-3-carboxylate;
Ethyl 1-(6-(pyridin-2-yl)quinolin-2-yl)piperidine-4-carboxylate;
1-(4-Methyl-6-(pyridin-4-yl)quinolin-2-yl)piperidine-4-carboxylic acid;
Ethyl 1-(4-methyl-6-(pyridin-4-yl)quinolin-2-yl)piperidine-4-carboxylate;
Ethyl 1-(6-(3-fluoro-4-methoxyphenyl)quinolin-2-yl)piperidine-4-carboxylate;
Ethyl 1-(6-(3-chloro-4-methoxyphenyl)quinolin-2-yl)piperidine-4-carboxylate;
Ethyl 1-(6-(3,4-dimethoxyphenyl)quinolin-2-yl)piperidine-4-carboxylate;
1-(6-(Pyridin-2-yl)quinolin-2-yl)piperidine-4-carboxylic acid;
1-(6-(Pyridin-4-yl)quinolin-2-yl)piperidine-3-carboxylic acid hydrochloride;
Ethyl 1-(6-(4-chloro-3-fluorophenyl)quinolin-2-yl)piperidine-4-carboxylate;
Ethyl 1-(6-(3-chlorophenyl)quinolin-2-yl)piperidine-4-carboxylate;
Ethyl 1-(6-(4-chlorophenyl)quinolin-2-yl)piperidine-4-carboxylate;
Ethyl 1-(6-(3-(trifluoromethyl)phenyl)quinolin-2-yl)piperidine-4-carboxylate;
Ethyl 1-(6-(pyridin-4-yl)quinolin-2-yl)pyrrolidine-3-carboxylate;
Ethyl 1-(6-(benzo[b]thiophen-2-yl)quinolin-2-yl)piperidine-4-carboxylate;
Ethyl 1-(6-(2-(trifluoromethyl)phenyl)quinolin-2-yl)piperidine-4-carboxylate;
Ethyl 1-(6-(2-(trifluoromethoxy)phenyl)quinolin-2-yl)piperidine-4-carboxylate;
Ethyl 1-(6-(4-fluoro-2-methoxyphenyl)quinolin-2-yl)piperidine-4-carboxylate;
Ethyl 1-(6-(4-methoxy-3-(trifluoromethyl)phenyl)quinolin-2-yl)piperidine-4-carboxylate;
Ethyl 1-(6-(4-chloro-3-methoxyphenyl)quinolin-2-yl)piperidine-4-carboxylate;
Ethyl 1-(6-(3-fluorophenyl)quinolin-2-yl)piperidine-4-carboxylate;
Ethyl 1-(6-(3-chloro-4-fluorophenyl)quinolin-2-yl)piperidine-4-carboxylate;
Ethyl 1-(6-(2-methoxypyridin-3-yl)quinolin-2-yl)piperidine-4-carboxylate;
Ethyl 1-(6-(5-fluoropyridin-3-yl)quinolin-2-yl)piperidine-4-carboxylate;
Ethyl 1-(6-(3-fluoropyridin-4-yl)quinolin-2-yl)piperidine-4-carboxylate;
Methyl 1-(6-(pyridin-4-yl)quinolin-2-yl)piperidine-4-carboxylate;
1-(6-(6-methylpyridin-3-yl)quinolin-2-yl)piperidine-4-carboxylic acid hydrochloride.

Another aspect of the present disclosure relates to the use of the compounds of the present disclosure in medicine or veterinary. Preferably, the compound is used in the treatment or prevention of tuberculosis.

In an embodiment, the compound now disclosed is used in combination with at least one anti-HIV agent. Preferably, the anti-HIV agent is selected from the following: HIV protease inhibitor (PI), HIV nucleoside reverse transcriptase inhibitor (NRTI), HIV non-nucleoside reverse transcriptase inhibitor (NNRTI), HIV integrase inhibitor In an embodiment, the compound is combined with at least another TB drug. Preferably, the TB drug is selected from the following: isoniazid, rifamycin and derivatives, pyrazinamide, ethambutol, cycloserine, ethionamide, streptomycin, amikacin, kanamycin, rifampin (rifampicin), aminoglycosides, capreomycin, p-aminosalicyclic acid, fluoroquinolones such as levofloxacin, moxafloxacin or gatifloxacin, or mixtures thereof and all other first and second-line drug products.

In an embodiment, the combined anti-HIV agent or TB drug is administered simultaneously, separately or sequentially.

The present disclosure also relates to a pharmaceutical composition comprising a compound now disclosed and a pharmaceutically acceptable excipient.

In an embodiment, said pharmaceutical composition may comprise (i) a therapeutically effective amount of compound described or a pharmaceutically acceptable salt or solvate thereof; and (ii) a pharmaceutically acceptable excipient.

In an embodiment, surprisingly the compounds of the disclosure have been found to inhibit the growth of *Mycobacterium tuberculosis*. In particular, the compounds possess growth inhibition in vitro at concentration not more than 15.6 µM, in particular not more than 7.8 µM. The compounds have also been found to be non-cytotoxic for HepG2 cell line, metabolically stable in human microsomes, stable in plasma and relatively permeable under gastrointestinal tract parallel artificial membrane.

In the present disclosure '$C_1$-$C_6$ alkyl' refers to a linear or branched saturated hydrocarbon group containing from one to six carbon atoms. Examples of '$C_1$-$C_6$ alkyl' include methyl, ethyl, isopropyl, n-propyl, tert-butyl, sec-butyl, n-butyl, isobutyl, n-pentyl, isopentyl, n-hexyl. Preferably the hydrocarbon is linear.

In the present disclosure 'Halogen' as used herein refers to a fluoro (F), chloro (Cl), bromo (Br) or iodo (I), unless otherwise specified.

In the present disclosure '$C_1$-$C_6$ Haloalkyl' as used herein refers to a $C_1$-$C_6$ alkyl group as defined above substituted by one or more halogen atoms.

In the present disclosure 'Aryl' as used herein refers to a $C_6$-$C_2$ monocyclic or bicyclic hydrocarbon ring wherein at least one ring is aromatic. Examples of 'Aryl' group include phenyl, naphthalenyl, tetrahydronephthalenyl and indane.

In the present disclosure '$C_1$-$C_6$ alkoxy' as used herein refers to a —O($C_1$-$C_6$ alkyl) group wherein $C_1$-$C_6$ alkyl is as defined above. Examples of such groups include methoxy, ethoxy, isopropoxy, butoxy, pentoxy and hexyloxy.

In the present disclosure '$C_1$-$C_6$ haloalkoxy' as used herein refers to a —O($C_1$-$C_6$ alkyl) group as defined above substituted by one or more halogen atoms.

In the present disclosure 'Heteroaryl' as used herein refers to a 5-6 membered monocyclic aromatic or a fused 8-10 membered bicyclic aromatic ring, which might be partially saturated, which monocyclic or bicyclic ring contains 1 to 4 heteroatoms selected from oxygen, nitrogen, and sulphur. Examples of monocyclic aromatic ring include furyl, furazanyl, imidazolyl, isothiazolyl, isoxazolyl, oxazolyl, oxadiazolyl, thiadiazolyl, pyrrolyl, pyranyl, pyrazolyl, pyrimidyl, pyridazinyl, pyrazinyl, pyridyl, thienyl, thiazolyl, triazolyl, tetrazolyl, triazinyl, tetrazinyl and the like. Examples of such bicyclic aromatic rings include azaindolyl, benzothienyl, benzoimidazolyl, benzoxazolyl, benzoisoxazolyl, benzothiazolyl, benzoisothiazolyl, benzoxadiazolyl, benzothiadiazolyl, benzofuranyl, cinnolinyl, furopyridyl, imidazopyridyl, indolyl, isoindolyl, isobenzofuranyl, indolizinyl, indazolyl, isoquinolinyl, naphthyridinyl, quinolinyl, quinazolinyl, quinoxalinyl, phthalazinyl, pteridinyl, purinyl, pyrrolopyridyl.

In the present disclosure 'Bicyclic ring' and 'Fused' in the context of a bicyclic ring refers to two rings which are joined together across a bond between two atoms (e.g. naphthalene), across a sequence of atoms to form a bridge (e.g. quinuclidine, adamantyl) or together at a single atom to form a spiro compound (e.g. 1,4-dioxa-8-aza-spiro[4.5]decane).

In the present disclosure 'Substituted aryl' or 'Substituted heteroaryl' used herein with reference to R group means that a particular R group (e.g. Ra, Rb, Rc) can be substituted with one or more groups selected from Rx, halogen, OH, ORx, SH, SRx, OCORx, SCORx, COOH, $NH_2$, $NO_2$, CN, NHRx, NRxRy, CORx, CSRx, COORx, OPhRxRy, $CONH_2$, CONHRx, CONxNy, CONHOH, $CONHNH_2$, CONHORx, $CH_2CH_2NRxRx$, $CH_2CH_2NRxRy$, $NHCONH_2$, NRxCORy, NHCORx, CONHPhRx, CONRxRx, $CONHNH_2$, COHRx, NHCORx, $NHSO_2Rx$, wherein Rx and Ry are independently selected from $C_1$-$C_6$ alkyl, $C_1$-$C_6$-alkoxy, $C_1$-$C_6$ haloalkyl, $C_1$-$C_6$ haloalkoxy, aryl, heteroaryl, $C_3$-$C_{10}$ cycloalkyl, alkyl $C_1$-$C_6$ aryl and heterocyclyl, or Rx and Ry, together with the heteroatom to which they are joined, can form an heterocyclyl.

In the present disclosure 'Unsubstituted heteroaryl' as used herein refers to pyridin-2-yl, pyridin-3-yl, pyridin-4-yl, pyrimidin-5-yl, furan-2-yl or indolyl.

In the present disclosure 'Pharmaceutical acceptable' such as pharmaceutically acceptable carrier, excipient, etc. means pharmacologically acceptable and substantially non-toxic to the subject to which the particular compound is administrated.

In the present disclosure 'Pharmaceutically acceptable salts' of compounds of the present disclosure include salts with organic bases, salt with inorganic bases, salts with organic acids and salt with basic or acidic amino acids as well as quaternary ammonium salts. Salts with acids may, in particular, be employed in some instances. Examples of such salts include hydrochloric salt and trifluoroacetate salt.

In an embodiment, the compounds of the present disclosure is crystallised or recrystallized from solvents such as organic solvents. In such cases, solvate (e.g. hydrate) may form. When in a solvated form, additional solvent is alcohols such as isopropanol (isop) or ethanol (EtOH).

In the present disclosure, the prodrug form of the pharmacologically-active compounds disclosed herein are degraded in vivo to yield the compounds according to the present disclosure. Prodrugs are usually (but not always) of lower potency at the target receptor than the compounds to which they degrade into. Prodrugs are particularly useful when the desired compound has chemical or physical properties that make its administration difficult or inefficient. For example, the desired compound can only be poorly soluble, it is poorly transported across the mucosal epithelium, or it may have an undesirably short plasma half-life. Further discussion on prodrug can be found in Redasani, V. K. et al. 'Prodrug Design', Elsevier, U K, 2015.

In the present disclosure, prodrug forms of a pharmacologically-active compounds are compounds according to Formula I, II, III and IV, the pharmaceutically acceptable acid or base addition salts, the stereochemically isomeric form, the tautomeric forms thereof and the N-oxide forms thereof, having an acid group which is esterified or aminated; or an amino group which forms a carbamate or an amide. Included in esterified acid groups are the 'Pharmaceutically acceptable esters'.

In the present disclosure, amidated groups include groups of the formula —$CONR_dR_e$, wherein $R_d$ is H, $C_1$-$C_6$ alkyl, and $R_e$ is OH, H, $C_1$-$C_6$ alkyl.

In the present disclosure, carbamate include groups of the formula —$NR_fCOOR_g$, wherein $R_f$ is H or $C_1$-$C_6$ alkyl and $R_g$ is $C_1$-$C_6$ alkyl or $C_1$-$C_6$ alkyl substituted with —OCO ($C_1$-$C_6$ alkyl).

In the present disclosure, amine include groups of the formula —$NR_fR_h$, wherein $R_f$ is as previously described and $R_h$ is H or $C_1$-$C_6$ alkyl.

In the present disclosure, 'Pharmaceutically acceptable esters' of compounds are compounds which one or more carboxyl group (e.g. —COOH) are modified by reaction with an alcoholic substituent A-OH so as to yield —COOA groups, wherein A is $C_1$-$C_6$ alkyl.

In the present disclosure, N-oxide forms of the compounds according to Formula I, II, III and IV are meant to comprise those compounds wherein one or several Nitrogen atoms are oxidized to the so-called N-oxide, particularly those N-oxide wherein the Nitrogen of the Amine radical is oxidized.

The skilled person will appreciate that compounds of the present disclosure include those that are chemically stable. That is, compounds of the invention include those that are sufficiently robust to survive isolation from the reaction mixture to a useful degree of purity.

General methods for the preparation of salts and esters are well known to the person skilled in the art. Pharmaceutically acceptability of salts and esters will depend on a variety of factors, including formulation processing details, and specific in vivo criteria, and the person skilled in the art would be able to assess such details having the present disclosure in consideration.

If a chiral centre or another form of isomeric centre, such as geometric isomers are present in a compound of the present disclosure, all forms of isomers, including enantiomers and diastereomers, are intended to be enclosed herein. Compounds of the present disclosure containing a chiral centre are used as a mixture of isomers in all ratios (e.g. racemic mixture), an enantiomerically enriched mixture, or in a pure form. Individual isomers, or enantiomers are obtained by methods known in the art, such as optical resolution of products or intermediates (for example chiral chromatography (e.g. chiral HPLC) or supercritical fluid chromatography (SFC)). Wherein compounds of the disclosure may exist as alternative tautomeric forms (e.g. keto/enol, imine/enamine), the disclosure relates to the individual tautomers in isolation, and to a mixture of the tautomers in all proportions.

Other aspects of the present disclosure are the provision of compounds according to the present disclosure, or a pharmaceutical composition comprising said compound for use in the treatment and/or prevention of tuberculosis.

In an embodiment, the compounds of general formula I, II, III and IV are used in combination with other TB drug products such as isoniazid, rifampin, pyrazinamide, ethambutol, fluoroquinolones, aminoglycosides and all other first and second-line drug products.

In an embodiment, the present disclosure describes the use of one of the compounds disclosed in combination with at least one TB drug or, a pharmaceutical composition comprising that compound in combination with at least one TB drug for use in the treatment or prevention of tuberculosis.

In an embodiment, the TB drug is selected from the following: isoniazid, rifamycin and derivatives, pyrazinamide, ethambutol, cycloserine, ethionamide, streptomycin, amikacin, kanamycin, rifampin (rifampicin), capreomycin, p-aminosalicyclic acid, aminoglycosides, fluoroquinolones such as levofloxacin, moxifloxacin or gatifloxacin, and all other first and second-line drug products.

In an embodiment, the compounds of general formula I, II, III and IV, whether or not in combination with another pharmacologically active compound, are administered by oral, nasal, rectal, bronchial (inhaled), topical (eye drops, buccal, and sublingual), vaginal, parenteral (subcutaneous, intramuscular, intravenous and intradermal) or via an implanted reservoir, and are prepared by any methods known in the art or pharmacy.

In an embodiment, the composition is prepared by bringing into association the above defined active ingredient with a carrier. In general, the formulations are prepared oy uniformly and intimately bringing into association the active ingredient with liquid carriers or finely divided solid carriers, or both, and then if necessary, shaping the product.

In an embodiment, the present disclosure describes the use of a compound of general formula I, II, III and IV as defined above in the preparation of an anti-mycobacterial agent, particularly as agent for the treatment or prevention of tuberculosis.

In an embodiment, the compounds of formula I, II, III and IV or a pharmaceutically acceptable derivative thereof, are prepared from compound of general formula VI. In particular, the compounds according to formula I, II, III and IV can be prepared by reacting compound of formula VI with compound of formula VII according to scheme 1 by using a Suzuki coupling reaction in the presence of a palladium catalyst, a suitable base and a suitable solvent.

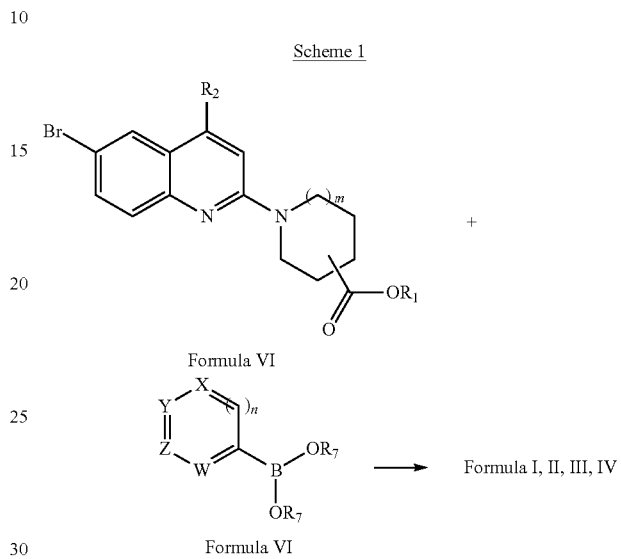

Scheme 1

In an embodiment, the compound of formula VII is a boronic acid wherein $R_7$ is H; or compound of formula VII Is a boronic ester wherein $R_7$ is $C_1$-$C_6$ alkyl or the carbons on the two $R_7$ are taken together to form a saturated ring as —O(C($R_a$)$_2$)$_n$O—, wherein p is 2 or 3, and $R_a$ is H or $C_1$-$C_6$ alkyl, thereby forming e.g. a pinacolato boronate ester.

In an embodiment, the palladium catalyst is a palladium transition metal catalyst selected from the following: palladium diacetate, bis(triphenylphosphine)palladium(II) dichloride, tetrakis(triphenylphosphine)palladium(0), dichlorobis(tri-o-tolylphosphine)palladium(II), [1,2-Bis(diphenylphosphino)ethane]dichloropalladium(II), 1,4-Bis(diphenylphosphino)butane-palladium(II) chloride, (1,3-Bis (diphenylphosphino)propane)palladium(II) chloride or [1,1'-Bis(diphenylphosphino)ferrocene]dichloropalladium (II), more preferably palladium catalyst is tetrakis(triphenylphosphine)palladium(0).

In an embodiment, the palladium catalyst described herein can be prepared in situ from metal salts and ligands. This include reacting under an inert atmosphere, a Pd(II) species and a phosphine ligand, such as palladium acetate and triphenylphosphine. Additional ligands which can be used with the methods described herein include ligands elected from the following: 1,1'-bis(diphenylphosphino)ferrocene (dppf), 1,2-bis(diphenylphosphino)ethane (dppe), 1,4-bis(diphenylphosphino)butane (dppb), or 1,3-bis(diphenylphosphino)propane (dppp). These in situ catalysts can be prepared by initial reaction of metal salt and ligand, followed by addition to the reaction mixture, or by separate addition of a metal salt and ligand directly to the reaction mixture.

In an embodiment, the suitable base is an inorganic base. Suitable inorganic base includes but are not limited to caesium carbonate, sodium carbonate, potassium carbonate, sodium hydroxide, potassium hydroxide, sodium bicarbonate, sodium phosphate or sodium acetate. In a preferred embodiment, the base is selected from the group consisting of potassium carbonate, sodium carbonate and caesium carbonate. More preferably, the base is caesium carbonate.

In an embodiment, the suitable solvents include, but are not limited to, dimethyl formamide (DMF), dimethylacetamide (DMA), 1,2-dimethoxyethane (DME), dimethylsulfoxyde (DMSO), N-methylpyrrolidone (NMP), dioxane, benzene, toluene, methanol (MeOH), EtOH, 1-butanol (1-BuOH), Isop, dichloromethane (DCM) or water, and mixtures thereof. In a preferred embodiment, the solvent is dioxane, alone or in a mixture with water. More preferably, the solvent is a mixture of dioxane and water.

In an embodiment the temperature is preferably from 50° C. to 100° C., for example the temperature is 80° C.

In an embodiment the catalyst load is from 2 to 15 mol %, more preferably it is 5 mol %.

In an embodiment, compound of formula VI is prepared by reacting compound of formula VIII with compound of formula IX, according to scheme 2:

Scheme 2

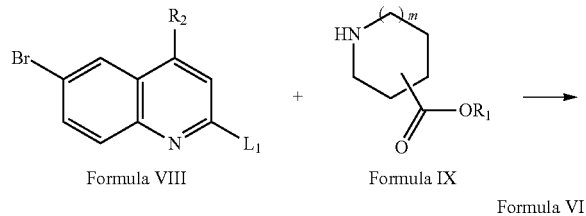

Formula VIII    Formula IX

Formula VI wherein $L_1$ is a leaving group by reaction with a compound of general formula IX, preferably $L_1$ is a leaving group, preferably $L_1$ is a halogen selected from Br, Cl or F, more preferably, $L_1$ is Cl or Br; and $R_1$, $R_2$ and m are as defined for compound of general formula I.

In an embodiment, compound of formula VIII and compound of formula IX are reacted together at elevated temperature in the absence of solvent (neat). The reaction might be carried out in protic solvent such as ethanol or in the presence of aprotic solvent such as toluene.

In an embodiment, compounds of formula I is prepared by preferably reacting compound of formula VIII and compound of formula IX in the presence of solvent such as 1-BuOH and an alkaline agent such as N,N-diisopropylethylamine (DIPEA) to obtain compound of formula VI.

In an embodiment, the temperature is preferably from 80° C. to 160° C., for example the temperature is 130° C.

Compounds of general formula VIII are known and are commercially available or are prepared by methods known to those of skill in the art.

In an embodiment, for example, a compound of general formula VIII in which $L_1$ is Cl, is prepared from a compound of general formula X Formula X

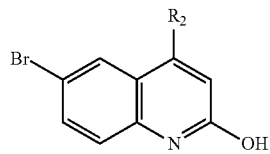

by reacting with trichlorophosphate, phosphorous pentachloride, oxalyl chloride or thionyl chloride under heating in polar aprotic solvent such as dimethylformamide (DMF) or acetonitrile (MeCN).

In an embodiment, compounds of general formula X are known and are commercially available or are prepared by methods known to those of skill in the art. For example, a compound of general formula X is prepared from a compound of general formula XI Formula XI

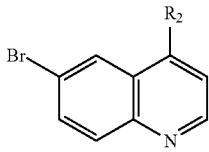

by reacting with dihydrogen peroxide under acidic conditions or 3-chloro-perbenzoic acid in halogenated solvents at ambient temperature to afford the respective N-oxide; followed by reaction with acetic anhydride under heating conditions to provide compound of formula X.

DETAILED DESCRIPTION

The present disclosure relates to the use of 1-(quinolin-2-yl)piperidine-4-carboxylic acid compounds substituted with a 6-aryl or heteroaryl for treating and/or preventing tuberculosis.

In an embodiment, the compounds of general formula I are prepared.

Example 1

The compounds can generally be prepared by a succession of steps. The processes used for the synthesis of the compounds of the present disclosure are illustrated by a general scheme. Raw materials and reagents used to prepare compounds from the present disclosure are available from commercial suppliers or they can be prepared by methods known to those skilled in the art. The general schemes are merely illustrative of methods by which the compounds of this invention are synthesised, modifications to these schemes are suggested by those skilled in the art having referred to this disclosure.

In an embodiment, where the process refers to room temperature, the temperature is preferably from 20° C. to 25° C., more preferably 20° C.

In an embodiment, the compounds are characterised by melting point, High Performance Liquid Chromatography Mass Spectrometry (HPLC-MS) and Nuclear Magnetic Resonance (NMR). HPLC-MS was performed on instrument HPLC Waters Alliance 2690 with detection performed by a Waters 2996 DAD detector (Diode Array Detector) and a QDA Waters mass spectrometer operating in electrospray (ES) ionization mode.

In an embodiment, MS data acquisition was performed with appropriate software. Compounds are described by their reported molecular ion which corresponds to the $[M+H]^+$ or $[M+2H]^+$ (protonated molecules) and/or $[M-H]^-$ (deprotonated molecule). For molecules with multiple isotropic patterns (Br, Cl . . . ), the reported value is the one obtained for the lowest isotope mass. All results were obtained with experimental uncertainties that are commonly associated with the method used.

In an embodiment, the HPLC column used was a Sunfire C18, 5 m (250×4.6 mm). The mobile phase was acetonitrile (A) and water with 0.1% formic acid (B) (75% A/25% B). The run time was 10 min, the flow rate was 1 mL/min and the temperature was 35° C.

In an embodiment, melting point was recorded on a Buchi MP-M560 at 20° C./min readings.

40) In an embodiment, $^1$H NMR spectra were recorded on a Bruker instrument operating at 400 or 500 MHz with solvent used as internal standard. Peak multiplicity abbreviations are s (singlet), d (doublet), t (triplet), m (multiplet), br (broad), dd (doublet of doublets), ddd (doublet of doublet of doublets), dtd (Doublet of triplet of doublets), ddt (Doublet of doublet of triplets), dt (doublet of triplets), td (triplet of doublets), q (quartet), tt (Triplet of triplets) and hept (Heptet). Coupling constant are reported in Hertz (Hz). $^{13}$C NMR spectra were recorded at 101 or 126 MHz.

In an embodiment, column chromatography was performed by flash chromatography on silica gel 60 (Merck), particle size 0.063-0.2 mm as stationary phase.

In an embodiment, purification of compounds via recrystallization was achieved by dissolving the crude compound in the minimum volume of a hot solvent of choice, generally a protic solvent, then covering the container and leaving it to cool down to room temperature and then at 0° C. gradually until crystal formation was observed.

In an embodiment, isolation of pure compound over column chromatography was achieved by collecting column fractions containing pure compound, evaporating the solvent in the rotavap and drying the residue under high vacuum at 40° C.

In an embodiment, the method of synthesizing intermediate 1 (Ethyl 1-(6-bromoquinolin-2-yl)piperidine-4-carboxylate) is as follows:

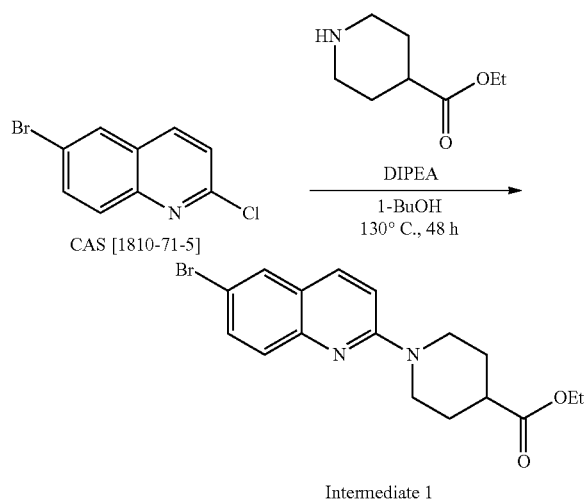

DIPEA (5 ml) was added to a suspension of 2-Chloro-6-bromoquinoline (590 mg, 2.4 mmol) and ethyl ison pecotate (570 mg, 3.6 mmol) in 1-BuOH (12 ml) and the mixture was allowed to stir at 130° C. over 48 hours. The solvent was evaporated, and the resulting residue was purified by column chromatography (silica gel, DCM-DCM/MeOH 2%) to obtain the title Intermediate 1 as a yellow solid (850 mg, 96%).

In an embodiment, the method of synthesizing compound 1 (Ethyl 1-(6-(4-(trifluoromethoxy)phenyl)quinolin-2-yl)piperidine-4-carboxylate) is as follows:

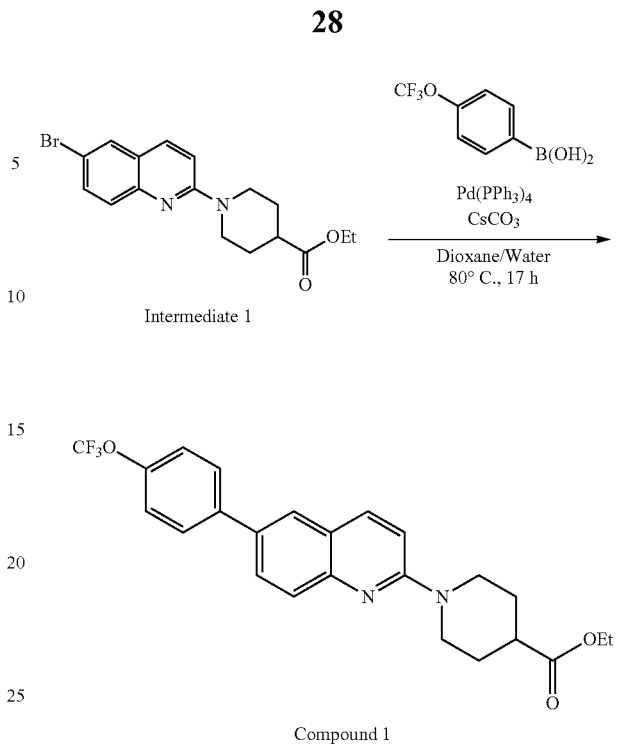

Tetrakis(triphenylphosphine)palladium(0) (114 mg, 0.1 mmol) was added to a stirring suspension of intermediate 1 (ethyl 1-(6-bromoquinolin-2-yl)piperidine-4-carboxylate) (650 mg, 1.79 mmol), (4-(trifluoromethoxy)phenyl)boronic acid (405 mg, 1.97 mmol) and caesium carbonate (3 ml, 3M solution) in a mixture of dioxane (16 ml) and water (2.6 ml). The suspension was allowed to stir at 80° C. over 17 hours. The solvent was evaporated in high vacuum and the residue was purified by column chromatography (silica gel, Petrol ether/Ethyl acetate (EtOAc) 6:1) to obtain the title Compound 1 as a colourless solid (417 mg, 52%).

HPLC-MS [M+H]$^+$ 445.17; MP: 188-194° C.; $^1$H NMR (400 MHz, CDCl$_3$) δ 7.92 (d, J=9.2 Hz, 1H), 7.76 (bs, 3H), 7.70-7.64 (m, 2H), 7.30 (d, J=8.3 Hz, 2H), 7.03 (d, J=9.2 Hz, 1H), 4.49 (dt, J=13.4, 4.0 Hz, 2H), 4.17 (q, J=7.1 Hz, 2H), 3.13 (ddd, J=13.9, 11.5, 2.8 Hz, 2H), 2.60 (tt, J=11.0, 3.9 Hz, 1H), 2.09-2.01 (m, 2H), 1.88-1.76 (m, 2H), 1.31-1.23 (m, 3H); $^{13}$C NMR (101 MHz, CDCl$_3$) δ 174.71, 157.43, 148.35, 147.57, 139.76, 137.58, 133.52, 128.67, 128.26, 127.15, 125.18, 122.98, 121.82, 121.28, 110.29, 60.51, 44.80, 41.49, 27.94, 14.2.

In an embodiment, the method of synthesizing compound 2 (1-(6-(4-(Trifluoromethoxy)phenyl)quinolin-2-yl)piperidine-4-carboxylic acid) is as follows:

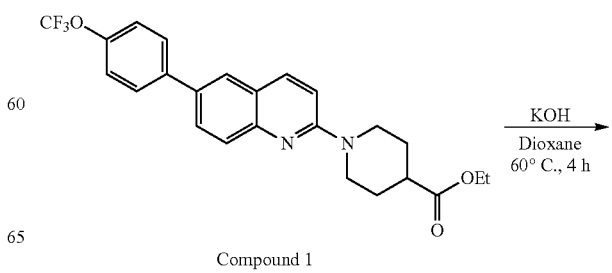

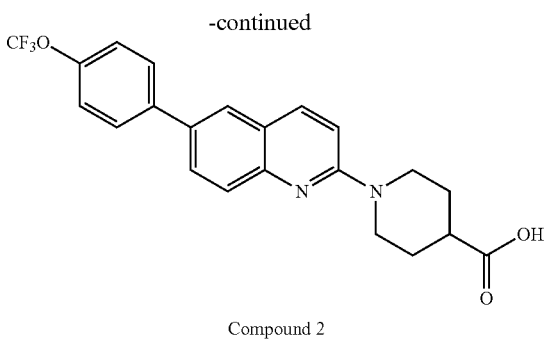

Compound 2

An aqueous solution of potassium hydroxide (5 ml, 5N solution) was added to a solution of compound 1 (ethyl 1-(6-(4-(trifluoromethoxy)phenyl)quinolin-2-yl)piperidine-4-carboxylate) (340 mg, 0.766 mmol) in dioxane (5 ml). The mixture was allowed to stir at 60° C. for a duration of 4 hours. The dioxane was evaporated and the resulting aqueous mixture was acidified with a 37% hydrochloric acid solution. The aqueous solution was extracted with EtOAc, the organic layer was dried with anhydrous $Na_2SO_4$, was filtered and evaporated in high vacuum to obtain Compound 2 as a colourless solid (164 mg, 51%).

HPLC-MS [M+H]$^+$ 417.18; MP: 245-250° C.; $^1$H NMR (400 MHz, DMSO-$d_6$) δ 8.08 (d, J=9.2 Hz, 1H), 8.03 (1, J=2.2 Hz, 1H), 7.89-7.84 (m, 3H), 7.63 (d, J=8.7 Hz, 1H), 7.46 (d, J=8.2 Hz, 2H), 7.30 (d, J=9.3 Hz, 1H), 4.45 (dt, J=13.6, 3.9 Hz, 2H), 3.09 (ddd, J=13.8, 11.5, 2.8 Hz, 3H), 1.93 (dd, J=13.8, 4.0 Hz, 2H), 1.62-1.52 (m, 2H); $^{13}$C NMR (101 MHz, DMSO-$d_6$) δ 176.45, 157.55, 147.95, 147.57, 139.74, 138.14, 132.33, 128.71, 128.59, 127.02, 125.70, 123.13, 121.93, 111.17, 44.61, 30.88, 28.22.

In an embodiment, the method of synthesizing compound 3 (ethyl 1-(6-(4-hydroxyphenyl)quinolin 2-yl)piperidine-4 carboxylate) is as follows:

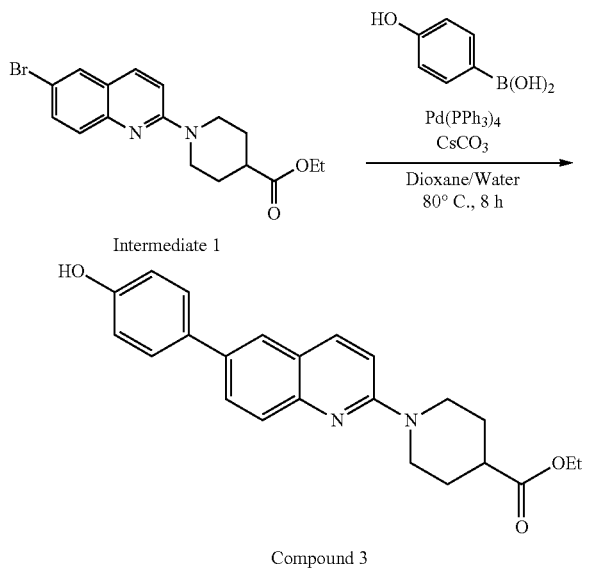

Tetrakis(triphenylphosphine)palladium(0) (95 mg, 0.08 mmol) was added to a stirring suspension of intermediate 1 (ethyl 1-(6-bromoquinolin-2-yl)piperidine-4-carboxylate) (600 mg, 1.65 mmol), (4-hydroxyphenyl)boronic acid (251 mg, 1.82 mmol) and caesium carbonate (3 ml, 3M solution) in a mixture of dioxane (16 ml) and water (2.6 ml). The suspension was allowed to stir at 80° C. for a duration of 8 hours. The solvent was evaporated in high vacuum and the residue was purified by column chromatography (silica gel, Petrol ether/EtOAc 2:11 to obtain Compound 3 as an off-white solid (165 mg, 27%).

HPLC-MS [M+H]$^+$ 377.27; MP: 187-189° C.; $^1$H NMR (400 MHz, CDCl$_3$) δ 7.91 (d, J=9.1 Hz, 1H), 7.78-7.70 (m, 3H), 7.57-7.51 (m, 2H), 7.01 (d, J=9.1 Hz, 1H), 6.94-6.88 (m, 2H), 4.46 (dt, J=13.5, 4.0 Hz, 2H), 4.16 (q, J=7.1 Hz, 2H), 3.12 (ddd, J=13.8, 11.4, 2.9 Hz, 2H), 2.59 (tt, J=11.0, 4.0 Hz, 1H), 2.09-2.00 (m, 2H), 1.88-1.76 (m, 2H), 1.31-1.23 (m, 3H); $^{13}$C NMR (101 MHz, CDCl$_3$) δ 174.87, 166.00, 157.30, 155.12, 137.66, 134.79, 133.51, 128.85, 128.24, 126.76, 124.34, 123.12, 115.74, 110.27, 60.56, 44.99, 41.50, 27.94, 14.23.

In an embodiment, the method of synthesizing compound 9 (1-(6-(4-hydroxyphenyl)quinolin-2-yl)piperidine-4-carboxylic acid) is as follows:

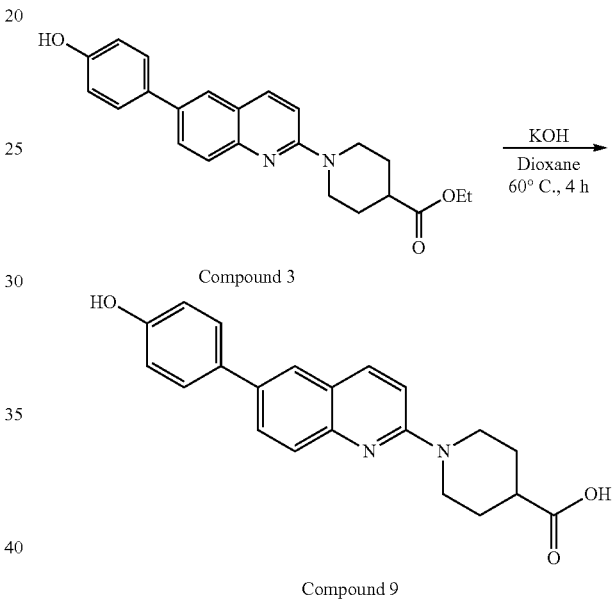

Compound 9

An aqueous solution of potassium hydroxide (3 ml, 5N solution) was added to a solution of compound 3 (ethyl 1-(6-(4-hydroxyphenyl)quinolin-7-yl)piperidine-4-carboxylate) (113.5 mg, 0.3 mmol) in dioxane (3 ml). The mixture was allowed to stir at 60° C. for a duration of 4 hours. The dioxane was evaporated and the resulting aqueous mixture was acidified with a 37% hydrochloric acid solution. The aqueous solution was extracted with EtOAc, the organic layer was dried with anhydrous $Na_2SO_4$, was subsequently filtered and evaporated in high vacuum to obtain Compound 9 as a yellow solid (61 mg, 57%).

HPLC-MS [M+H]$^+$ 349.21; MP: 270-278° C.; $^1$H NMR (500 MHz, DMSO-$d_6$) δ 8.04 (d, J=9.2 Hz, 1H), 7.88 (d, J=2.2 Hz, 1H), 7.77 (dd, J=8.7, 2.2 Hz, 1H), 7.56 (dd, J=8.4, 1.8 Hz, 3H), 7.24 (d, J=9.3 Hz, 1H). 6.91-6.83 (m, 2H), 4.46-4.38 (m, 2H), 3.10-3.01 (m, 21H), 2.55 (td, J=7.2, 3.6 Hz, 1H), 1.95-1.89 (m, 2H), 1.57 (ddd, J=11.3, 4.2, 1.9 Hz, 2H); $^{13}$C NMR (126 MHz, DMSO-$d_6$) δ 176.39, 172.52, 157.25, 146.77, 137.96, 134.15, 131.15, 128.41, 128.00, 126.81, 124.10, 123.27, 116.22, 110.97, 44.64, 41.03, 28.08, 21.55, 14.54.

In an embodiment, the method of synthesizing compound 4 (ethyl 1-(6-(2-methoxypyrimidin-5-yl)quinolin-2-yl)piperidine-4-carboxylate) is as follows:

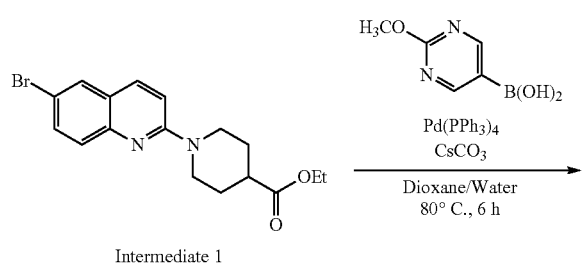

Tetrakis(triphenylphosphine)palladium(0) (95 mg, 0.08 mmol) was added to a stir ring suspension of intermediate 1 (ethyl 1-(6-bromoquinolin-2-yl)piperidine-4-carboxylate) (600 mg, 1.65 mmol), (2-methoxypyrimidin-5-yl)boronic acid (280 mg, 1.82 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 4 as a colourless solid (296 mg, 47%).

HPLC-MS [M+H]$^+$ 393.25; MP: 154-155° C.; $^1$H NMR (400 MHz, CDCl$_3$) δ 8.79 (bs, 2H), 7.92 (d, J=9.2 Hz, 1H), 7.77 (d, J=8.6 Hz, 1-1), 7.72-7.65 (m, 2H), 7.04 (d, J=9.2 Hz, 1H), 4.49 (dt, J=13.9, 4.1 Hz, 2H), 4.16 (q, J=7.1 Hz, 2H), 4.07 (s, 3H), 3.14 (ddd, J=13.8, 11.4, 2.9 Hz, 2H), 2.60 (tt, J=11.0, 4.0 Hz, 1H), 2.05 (dt, J=12.0, 3.8 Hz, 2H), 1.87-1.75 (m, 2H), 1.26 (d, J=7.2 Hz, 3H); $^{13}$C NMR (101 MHz, CDCl$_3$) δ 174.69, 164.83, 157.48, 157.17, 147.76, 137.45, 128.22, 128.00, 127.81, 127.66, 124.70, 123.10, 110.50, 60.54, 55.04, 44.73, 41.46, 27.93, 14.24.

In an embodiment, the method of synthesizing compound 6 (1-(6-(2-methoxypyrimidin-5-yl)quinolin-2-yl)piperidine-4-carboxylic acid) is as follows:

An aqueous solution of potassium hydroxide (5 ml, 5N solution) was added to a solution of compound 4 (ethyl 1-(6-(2-methoxypyrimidin-5-yl)quinolin-2-yl)piperidine-4-carboxylate) (200 mg, 0.51 mmol) in dioxane (4 ml). The mixture was allowed to stir at 60° C. for a duration of 4 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain Compound 6 as a pale yellow solid (76.5 mg, 42%).

HPLC-MS [M+H]$^+$ 365.24; MP: 238-242° C.; $^1$H NMR (400 MHz, DMSO-d$_6$) δ 12.10 (bs, 1H), 9.01 (bs, 2H), 8.13-8.04 (m, 2H), 7.93-7.88 (m, 1H), 7.70-7.62 (m, 1H), 7.33 (d, J=9.3 Hz, 1H), 4.46 (dt, J=13.5, 3.8 Hz, 2H), 3.98 (s, 3H), 3.19-3.04 (m, 2H), 2.59 (ddt, J=11.1, 7.1, 3.9 Hz, 1H), 1.99-1.89 (m, 2H), 1.66-1.52 (m, 2H); $^{13}$C NMR (126 MHz, DMSO-d$_6$) δ 176.12, 172.22, 164.89, 157.44, 138.11, 128.14, 127.81, 125.21, 123.22, 111.33, 55.11, 44.65, 28.11, 21.42.

In an embodiment, the method of synthesizing compound 5 (ethyl 1-(6-(4-isopropoxyphenyl)quinolin-2-yl)piperidine-4-carboxylate) is as follows:

Tetrakis(triphenylphosphine)palladium(0) (95 mg, 0.08 mmol) was added to a stirring suspension of intermediate 1 (ethyl 1-(6-bromoquinolin-2-yl)piperidine-4-carboxylate) (600 mg, 1.65 mmol), (4-isopropoxyphenyl)boronic acid (281 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 5 as a colourless solid (330 mg, 48%).

HPLC-MS [M+H]+ 419.31; MP: 175-178° C.; $^1$H NMR (400 MHz, CDCl$_3$) δ 7.90 (d, J=9.1 Hz, 1H), 7.80-7.70 (m, 3H), 7.61-7.56 (m, 2H), 7.03-6.95 (m, 3H), 4.65-4.55 (m, 1H), 4.47 (dt, J=14.1, 4.2 Hz, 2H), 4.16 (q, J=7.1 Hz, 2H), 3.11 (ddd, J=13.9, 11.6, 2.8 Hz, 2H), 2.59 (tt, J=11.1, 4.0 Hz, 1H), 2.09-2.01 (m, 2H), 1.88-1.76 (m, 2H), 1.37 (d, J=6.0 Hz, 6H), 1.31-1.23 (m, 3H); $^{13}$C NMR (101 MHz, CDCl$_3$) δ 174.79, 157.27, 157.23, 147.04, 137.53, 134.78, 133.30, 128.78, 128.02, 126.91, 124.30, 123.13, 116.20, 110.15, 69.99, 60.50, 44.92, 41.54, 29.71, 27.95, 22.11, 14.24.

In an embodiment, the method of synthesizing Compound 7 (1-(6-(4-isopropoxyphenyl)quinolin-2-yl)piperidine-4-carboxylic acid) is as follows:

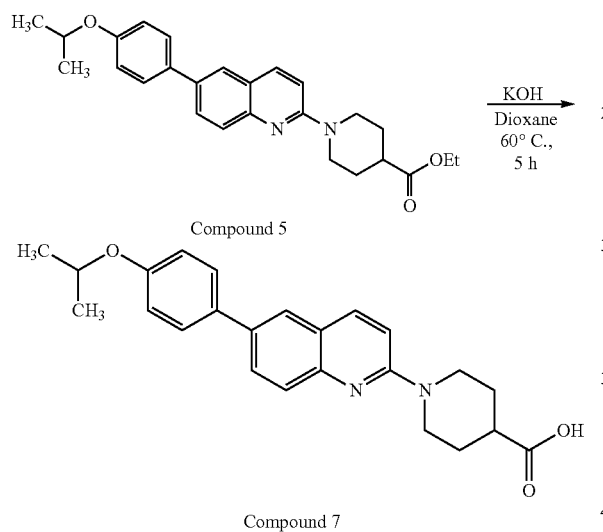

An aqueous solution of potassium hydroxide (4 ml, 5N solution) was added to a solution of compound 5 (ethyl 1-(6-(4-isopropoxyphenyl)quinolin-2-yl)piperidine-4-carboxylate) (200 mg, 0.48 mmol) in dioxane (4 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain Compound 7 as an off-white solid (127 mg, 68%).

HPLC-MS [M+H]+ 391.28; MP: 269-273° C.; $^1$H NMR (500 MHz, DMSO-d$_6$) δ 8.05 (d, J=9.2 Hz, 1H), 7.92 (d, J=2.2 Hz, 1H), 7.80 (dd, J=8.8, 2.2 Hz, 1H), 7.67-7.63 (m, 2H), 7.59 (d, J=8.7 Hz, 1H), 7.26 (d, J=9.3 Hz, 1H), 7.02-6.98 (m, 2H), 4.70-4.60 (m, 1H), 4.43 (dt, J=13.3, 3.8 Hz, 2H), 3.12-3.02 (m, 2H), 2.56 (ddt, J=11.1, 7.1, 3.9 Hz, 1H), 1.92 (dd, J=13.6, 3.8 Hz, 21H), 1.62-1.50 (m, 2H), 1.29 (d, J=6 Hz, 6H); $^{13}$C NMR (126 MHz, DMSO-d$_6$) δ 176.37, 157.29, 146.93, 138.00, 133.74, 132.48, 128.43, 128.03, 126.87, 124.41, 123.27, 116.48, 111.01, 69.65, 44.62, 41.03, 28.09, 22.33.

In an embodiment, the method of synthesizing Compound 8 (ethyl 1-(6-(3-fluorophenyl)quinolin-2-yl)piperidine-4-carboxylate) is as follows:

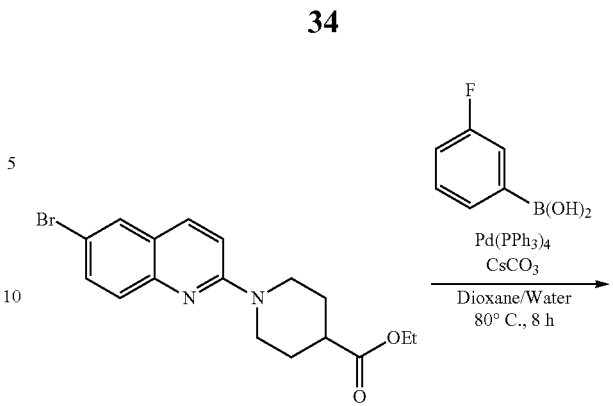

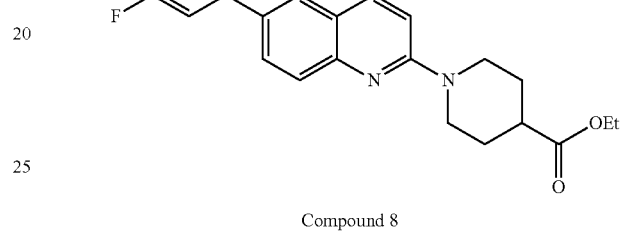

Tetrakis(triphenylphosphine)palladium(0) (95 mg, 0.08 mmol) was added to a stirring suspension of intermediate 1 (ethyl 1-(6-bromoquinolin-2-yl)piperidine-4-carboxylate) (600 mg, 1.65 mmol), (3-fluorophenyl)boronic acid (256 mg, 1.83 mmol) and caesium carbonate (3 ml, 3M solution) in a mixture of dioxane (16 ml) and water (2.6 ml). The suspension was allowed to stir at 80° C. for a duration of 8 hours. The solvent was evaporated in high vacuum and the residue was purified by column chromatography (silica gel, Petrol ether/EtOAc 4:1) to obtain Compound 8 as a colourless solid (320 mg, 51%).

HPLC-MS [M+H]+ 379.23; MP: 121-123° C.; $^1$H NMR (500 MHz, CDCl$_3$) δ 7.92 (d, J=9.2 Hz, 1H), 7.79-7.76 (m, 3H), 7.47-7.36 (m, 3H), 7.03 (dd, J=9.1, 6.7 Hz, 2H), 4.49 (dd, J=13.6, 4.0 Hz, 2H), 4.16 (q, J=7.1 Hz, 2H), 3.18-3.09 (m, 2H), 2.60 (tt, J=11.0, 3.9 Hz, 1H), 2.07-2.03 (m, 2H), 1.85-1.80 (m, 2H), 1.27 (t, J=7.1 Hz, 3H); $^{13}$C NMR (126 MHz, CDCl$_3$) δ 174.71, 164.25, 162.30, 157.46, 137.64, 128.64, 127.13, 122.60, 113.89, 113.72, 113.56, 110.28, 60.52, 44.81, 41.50, 27.95, 14.25.

In an embodiment, the method of synthesizing Compound 11 (1-(6-(3-fluorophenyl)quinolin-2-yl)piperidine-4-carboxylic acid) is as follows:

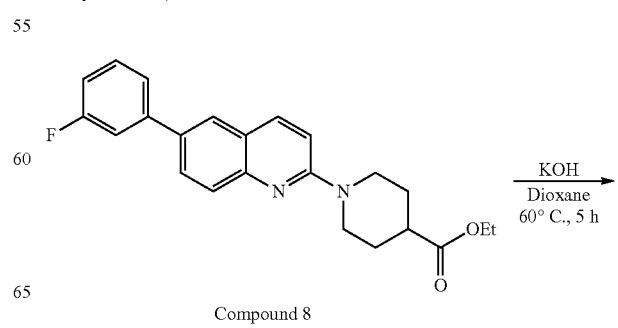

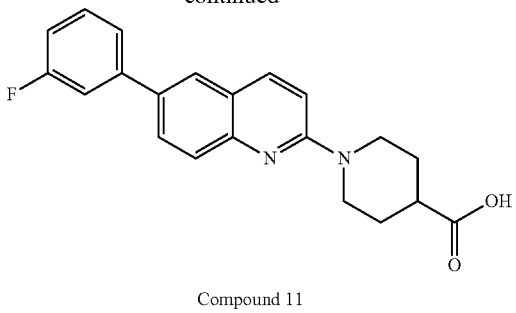

Compound 11

An aqueous solution of potassium hydroxide (4 ml, 5N solution) was added to a solution of compound 8 (ethyl 1-(6-(3-fluorophenyl)quinolin-2-yl)piperidine-4-carboxylate) (275.7 mg, 0.73 mmol) in dioxane (4 ml). The mixture was allowed to stir at 60° C. over 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain Compound 11 as an off-white solid (62 mg, 24%).

HPLC-MS [M+H]$^+$ 351.15; MP: 275-280° C.; $^1$H $^1$H NMR (400 MHz, DMSO-d6) δ 13.32 (bs, 1H), 8.40-7.91 (m, 4H), 7.66-7.61 (m, 2H), 7.60-7.38 (m, 1H), 7.27-7.17 (m, 1H), 4.48 (dt, J=14.0, 4.1 Hz, 2H), 3.58-3.45 (m, 2H), 2.70-2.64 (m, 1H), 2.00 (dd, J=12.7, 4.4 Hz, 2H), 1.72-1.66 (m, 2H); $^{13}$C NMR (126 MHz, DMSO-d6) δ 175.93, 164.20, 162.27, 142.01, 131.45, 131.39, 126.12, 123.05, 122.23, 114.59, 114.53, 113.76, 113.59, 46.08, 40.20, 28.04.

In an embodiment, the method of synthesizing Compound 12 (ethyl 1-(6-(3-fluoro-4-isopropoxyphenyl)quinolin 2 yl)piperidine 4 carboxylate) is as follows:

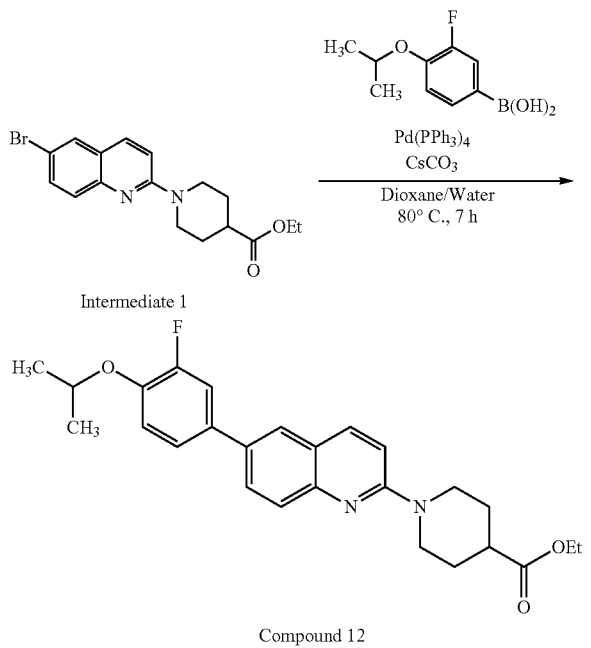

Compound 12

Tetrakis(triphenylphosphine)palladium(0) (95 mg, 0.08 mmol) was added to a stirring suspension of intermediate 1 (ethyl 1-(6-bromoquinolin-2-yl)piperidine-4-carboxylate) (528 mg, 1.46 mmol), (3-fluoro-4-isopropoxyphenyl)boronic acid (318 mg, 1.6 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain Compound 12 as an off-white solid (417.3 mg, 52%).

HPLC-MS [M+H]$^+$ 437.24; MP: 148-150° C.; $^1$H NMR (400 MHz, DMSO-d6) δ 7.90 (d, J=9.1 Hz, 1H), 7.76-7.70 (m, 3H), 7.41 (dd, J=12.6, 2.3 Hz, 1H), 7.35 (ddd, J=8.5, 2.3, 1.1 Hz, 1H), 7.10-6.98 (m, 2H), 4.59 (hept, J=12.2, 6.0 Hz, 1H), 4.47 (dt, J=13.4, 3.9 Hz, 2H), 4.16 (q, J=7.1 Hz, 2H), 3.12 (ddd, J=13.8, 11.6, 2.8 Hz, 2H), 2.59 (tt, J=11.0, 3.9 Hz, 1H), 2.08-2.02 (m, 2H), 1.87-1.77 (m, 2H), 1.40 (d, J=6.1 Hz, 6H), 1.27 (t, J=7.1 Hz, 3H); $^{13}$C NMR (101 MHz, DMSO-d6) δ 169.99, 152.59, 150.42, 147.98, 142.56, 132.80, 129.94, 128.78, 123.73, 122.28, 119.80, 118.27, 117.67, 113.31, 110.23, 105.49, 67.83, 55.76, 40.10, 36.75, 23.19, 17.38, 9.49.

In an embodiment, the method of synthesizing Compound 10 (1-(6-(3-fluoro-4-isopropoxyphenyl)quinolin-2-yl)piperidine-4-carboxylic acid) is as follows:

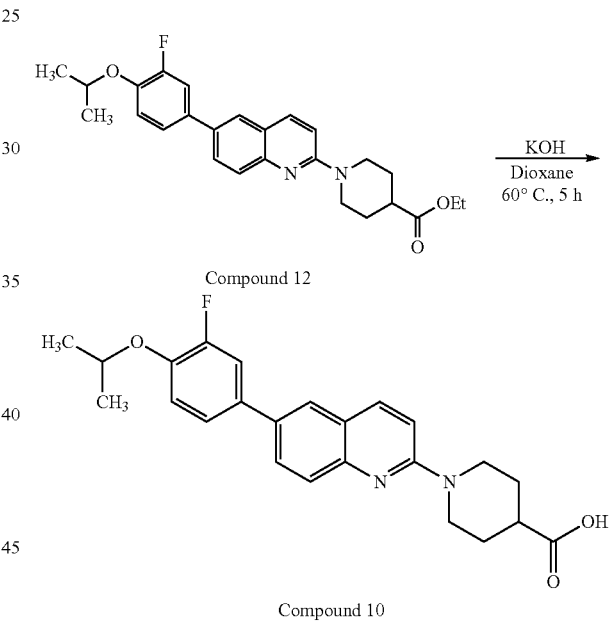

Compound 10

An aqueous solution of potassium hydroxide (4 ml, 5N solution) was added to a solution of compound 12 (ethyl 1 (6 (3-fluoro-4-isopropoxyphenyl)quinolin 2 yl)piperidine 4 carboxylate) (256 mg, 0.59 mmcl) in dioxane (4 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain Compound 10 as a colourless solid (184 mg, 76%).

HPLC-MS [M+H]$^+$ 409.28; MP: 262-266° C.; $^1$H NMR (400 MHz, DMSO-d6) δ 12.26 (bs, 1H), 8.06 (d, J=9.2 Hz, 1H), 7.99 (d, J=2.4 Hz, 1H), 7.87-7.80 (m, 1H), 7.66-7.56 (m, 2H), 7.55-7.45 (m, 1H), 7.32-7.20 (m, 2H), 4.67 (m, 1H), 4.67 (hept, J=6.0 Hz, 1H), 4.44 (dt, J=13.3, 3.8 Hz, 2H), 3.08 (ddd, J=13.7, 11.5, 2.7 Hz, 2H), 2.57 (tt, J 11.0, 3.9 Hz, 1H), 1.93 (dd, J=13.5, 3.7 Hz, 2H), 1.57 (dtd, J=13.1, 11.2, 3.9 Hz, 2H), 1.31 (d, J=6.0 Hz, 6H); $^{13}$C NMR (101 MHz, DMSO-d6) δ 176.31, 157.38, 154.60, 152.18, 147.21, 138.05, 133.61, 132.40, 128.32, 126.88, 124.89, 123.16, 122.82, 117.89, 114.62, 114.43, 111.09, 71.82, 44.57, 40.97, 28.08, 22.30.

In an embodiment, the method of synthesizing Compound 14 (ethyl 1-(6-(6-methoxypyridin-3-yl)quinolin-2-yl)piperidine-4-carboxylate) is as follows:

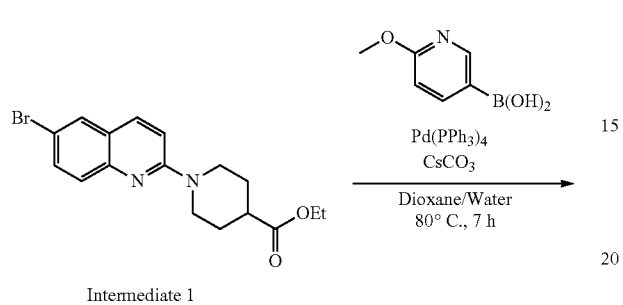

Intermediate 1

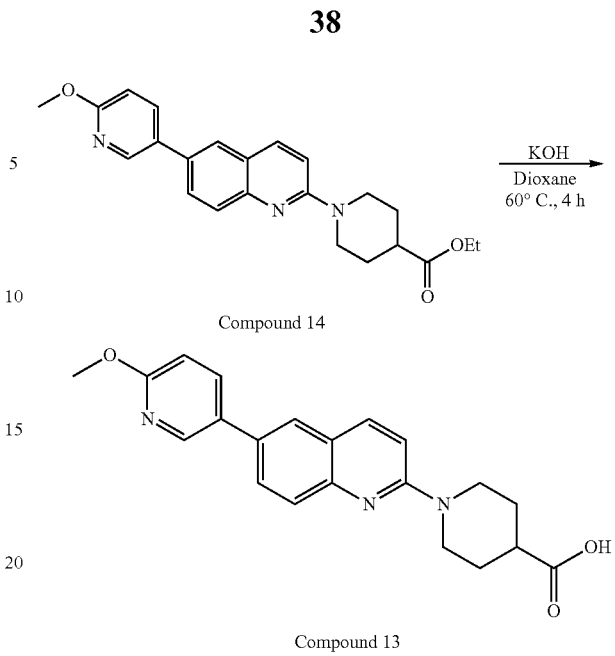

Compound 14

Tetrakis(triphenylphosphine)palladium(0) (95 mg, 0.08 mmol) was added to a stirring suspension of intermediate 1 (ethyl 1-(6-bromoquinolin-2-yl)piperidine-4-carboxylate) (600 mg, 1.65 mmol), (6-methoxypyridin-3-yl)boronic acid (280 mg, 1.81 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain Compound 14 as an off-white solid (116 mg, 18%).

HPLC-MS [M+H]$^+$ 392.30; MP: 141-144° C.; $^1$H NMR (400 MHz, CDCl$_3$) δ 8.46 (dd, J=2.6, 0.7 Hz, 1H), 7.91 (d, J=9.2 Hz, 1H), 7.87 (dd, J=8.6, 2.5 Hz, 1H), 7.79-7.67 (m, 31-H), 7.03 (d, J=9.2 Hz, 1H), 6.83 (d, J=8.5 Hz, 1H), 4.48 (dt, J=13.4, 3.9 Hz, 2H), 4.16 (q, J=7.1 Hz, 2H), 3.99 (s, 3H), 3.13 (ddd, J=13.8, 11.5, 2.9 Hz, 2H), 2.60 (tt, J=11.1, 4.0 Hz, 1H), 2.07-2.02 (m, 2H), 1.87-1.77 (dtd, J=13.3, 11.2, 4.0 Hz, 2H), 1.27 (t, J=7.1 Hz, 3H); $^{13}$C NMR (101 MHz, CDCl$_3$) δ 174.71, 163.36, 157.34, 147.33, 144.85, 137.48, 137.38, 131.67, 129.93, 128.40, 127.24, 124.53, 123.09, 110.77, 110.29, 60.51, 53.55, 44.84, 41.49, 27.94, 14.24.

In an embodiment, the method of synthesizing Compound 13 (1-(6-(6-methoxypyridin-3-yl)quinolin-2-yl)piperidine-4-carboxylic acid) is as follows:

An aqueous solution of potassium hydroxide (5 ml, 5N solution) was added to a solution of compound 14 (ethyl 1-(6-(6-methoxypyridin-3-yl)quinolin-2-yl)piperidine-4-carboxylate) (340 mg, 0.766 mmol) in dioxane (5 ml). The mixture was allowed to stir at 60° C. for a duration of 4 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain Compound 13 as a colourless solid (79 mg, 23%).

HPLC-MS [M+2H]$^+$ 365.21; MP: 221.225° C.; $^1$H NMR (400 MHz, DMSO-d6) δ 11.99 (bs, 1H), 9.00 (m, 2H), 8.14 (m, 1H), 8.09-8.02 (m, 2H), 7.92-7.85 (m, 1H), 7.64 (d, J=8.7 Hz, 1H), 7.30 (d, J=9.3 Hz, 1H), 4.45 (dt, J=13.2, 3.8 Hz, 2H), 3.97 (s, 3H), 3.09 (ddd, J=13.8, 11.5, 2.7 Hz, 2H), 2.56 (ddt, J=11.0, 7.8, 3.9 Hz, 1H), 1.98-1.89 (m, 2H), 1.64-1.49 (m, 2H); $^{13}$C NMR (101 MHz, DMSO-d6) δ 176.31, 167.90, 164.73, 157.52, 157.45, 147.58, 146.54, 137.98, 128.04, 127.73, 127.50, 125.16, 123.19, 111.25, 55.15, 44.49, 40.96, 28.11.

In an embodiment, the method of synthesizing Compound 15 (ethyl 1-(6-(pyridin-4-yl)quinolin-2-yl)piperidine-4-carboxylate hydrochloride) is as follows:

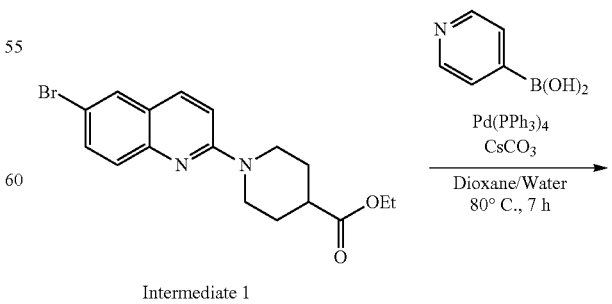

Intermediate 1

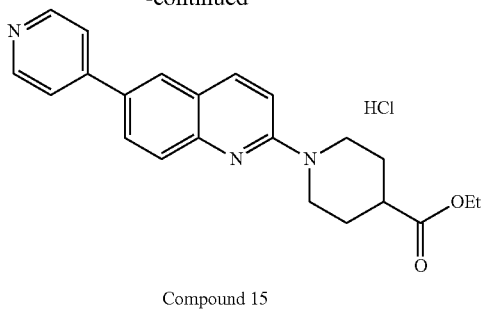

Compound 15

Tetrakis(triphenylphosphine)palladium(0) (92 mg, 0.08 mmol) was added to a stirring suspension of intermediate 1 (ethyl 1-(6-bromoquinolin-2-yl)piperidine-4-carboxylate) (600 mg, 1.65 mmol), pyridine-4-ylboronic acid (230 mg, 1.81 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 2:1-1:2). Fractions with product were collected and the solvent was evaporated. The resulting residue was dissolved in AcOEt and a 2N solution of hydrochloric acid in diethyl ether (3 eq) was added dropwise at 0° C. The precipitate was filtered and dried in high vacuum to obtain title Compound 15 as a colourless solid (181 mg, 28%).

HPLC-MS [M+H]$^+$ 362.24; MP: 249-263° C.; $^1$H NMR (400 MHz, DMSO-d6) δ 9.06-8.99 (m, 2H), 8.77-8.68 (m, 2H), 8.54-8.48 (m, 2H), 8.48-8.37 (m, 2H), 7.71 (d, J=9.8 Hz, 1H), 4.72-4.54 (m, 2H), 4.10 (q, J=7.1 Hz, 2H), 3.59 (ddd, J=14.1, 11.3, 2.8 Hz, 2H), 2.85 (tt, J=10.8, 4.3 Hz, —H), 2.07-2.02 (m, 2H), 1.83-1.73 (m, 2H), 1.20 (t, J=7.1 Hz, 3H); $^{13}$C NMR (101 MHz, DMSO-d6) δ 173.93, 154.53, 152.20, 142.63, 142.41, 139.93, 131.36, 130.50, 128.98, 124.13, 121.55, 120.05, 114.38, 60.64, 47.48, 39.55, 28.06, 14.55.

In an embodiment, the method of synthesizing Compound 18 (1-(6-(pyridin-4-yl)quinolin-2-yl)piperidine-4-carboxylic acid hydrochloride) is as follows:

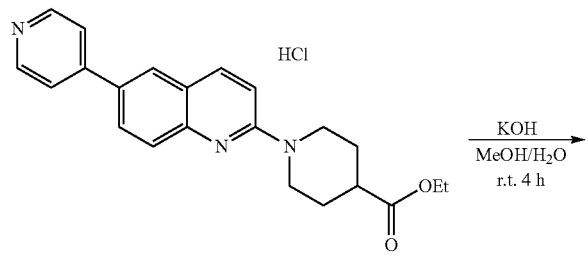

Potassium hydroxide (140 mg, 2.5 mmol) was added to a solution of compound 15 (ethyl 1 (6 (pyridin 4 yl)quinolin 2 yl)piperidine 4 carboxylate hydrochloride) (190 mg, 0.5 mmol) in a solution of MeOH/water (4:2) (3 ml). The mixture was allowed to stir at room temperature over 4.5 hours. The organic solvent was evaporated and the resulting aqueous mixture was acidified with hydrochloric acid (37%) to pH1. The aqueous solution was extracted with a mixture of DCM/isop (7:3), the organic layer was dried with anhydrous Na$_2$SO$_4$, was subsequently filtered and evaporated in high vacuum to obtain compound 18 as a yellow solid (140 mg, 75%).

HPLC-MS [M+H]$^+$ 334.15; MP: 293-297° C.; 1H NMR (400 MHz, DMSO-d6) δ 9.05-8.96 (m, 2H), 8.68 (d, J=2.1 Hz, 1H), 8.56 (d, J=8.8 Hz, 1H), 8.51-8.34 (m, 4H), 7.68 (d, J=9.8 Hz, 1H), 4.64-4.56 (m, 2H), 3.54 (ddd, J=13.8, 11.0, 2.7 Hz, 2H), 2.75 (tt, J=10.6, 4.2 Hz, 1H), 2.07-2.01 (m, 2H), 1.82-1.68 (m, 2H); $^{13}$C NMR (101 MHz, DMSO-d6) δ 175.64, 153.97, 153.40, 152.85, 143.08, 142.22, 131.01, 130.37, 128.82, 123.83, 121.70, 114.01, 47.14, 39.66, 28.13.

In an embodiment, the method of synthesizing Compound 16 (ethyl 1-(6-(furan-2-yl)quinolin-2-yl)piperidine-4-carboxylate) is as follows:

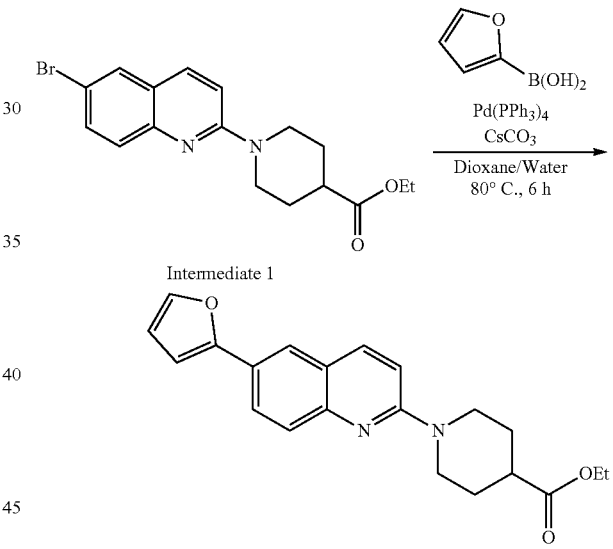

Compound 16

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), furan 2 ylboronic acid (204 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 16 as a yellow solid (123 mg, 21%).

HPLC-MS [M+H]$^+$ 351.17; MP: 202-204° C.; $^1$H NMR (400 MHz, CDCl$_3$) δ 9.03 (d, J=8.8 Hz, 1H), 8.10 (d, J=9.5 Hz, 1H), 7.98-7.91 (m, 1H), 7.88 (d, J=1.9 Hz, 1H), 7.49 (d, J=1.7 Hz, 1H), 7.06 (d, J=9.6 Hz, 1H), 6.74 (d, J=3.3 Hz, 1H), 6.53-6.47 (m, 1H), 4.69-4.50 (bs, 2H), 4.15 (q, J=7.1 Hz, 2H), 3.69 (m, 2H), 2.73 (tt, J=9.5, 4.4 Hz, 1H), 2.21-2.16 (m, 2H), 2.03-1.93 (m, 2H), 1.25 (t, J=7.1 Hz, 3H); $^{13}$C

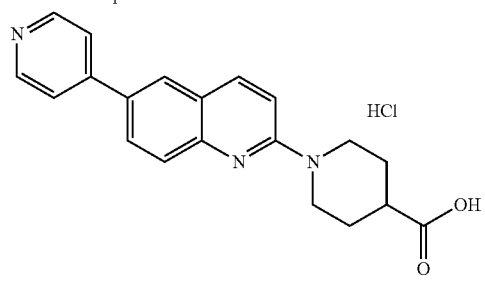

Compound 18

NMR (101 MHz, CDCl$_3$) δ 173.42, 152.08, 150.99, 143.12, 142.91, 129.09, 128.44, 121.41, 121.10, 120.58, 112.07, 111.15, 106.59, 60.99, 47.99, 39.66, 27.87, 14.17.

In an embodiment, the method of synthesizing Compound 17 (1-(6-(furan-2-yl)quinolin-2-yl)piperidine-4-carboxylic acid) is as follows:

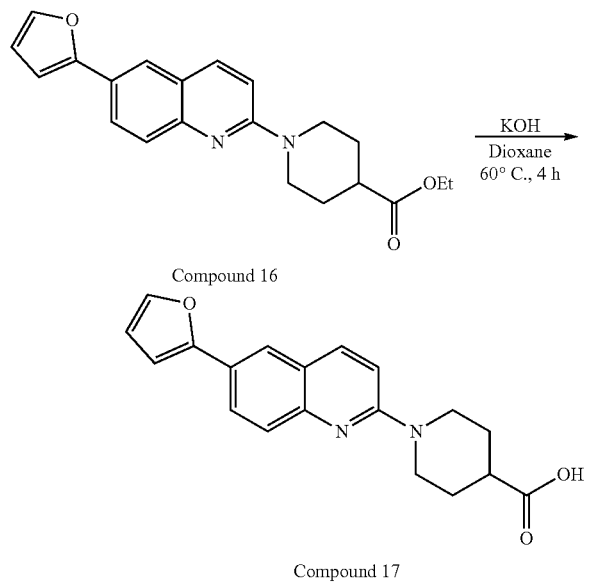

An aqueous solution of potassium hydroxide (5 ml, 5N solution) was added to a solution of compound 16 (ethyl 1-(6-(furan-2-yl)quinolin-2-yl)piperidine-4-carboxylate) (450 mg, 1.29 mmol) in dioxane (5 ml). The mixture was allowed to stir at 60° C. for a duration of 4 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain compound 17 as a yellow solid (324 mg, 78%).

HPLC-MS [M+H]$^+$ 323.14; MP: 210-214° C.; $^1$H NMR (400 MHz, DMSO-d6) δ 12.38 (bs, 1H), 8.44-8.26 (m, 1H), 8.21-8.11 (m, 1H), 8.10 8.00 (m. 1H), 7.93-7.78 (m, 2H), 7.61-7.47 (m, 1H), 7.03 (d, J=3.4 Hz, 1H), 6.69-6.62 (m, 1H), 4.41-4.35 (m, 2H), 3.38-3.25 (m, 2H), 2.72-2.64 (m, 1H), 2.05-1.97 (m, 2H), 1.76-1.64 (m. 2H); $^{13}$C NMR (126 MHz, DMSO-d6) δ 176.12, 157.90, 153.57, 143.10, 139.40, 138.61, 129.69, 126.36, 122.81, 121.97, 112.56, 111.55, 105.70, 44.86, 40.76, 28.05.

In an embodiment, the method of synthesizing Compound 19 (ethyl 1-(6-(2-chloro-4-methoxyphenyl)quinolin-2-yl)piperidine-4-carboxylate) is as follows:

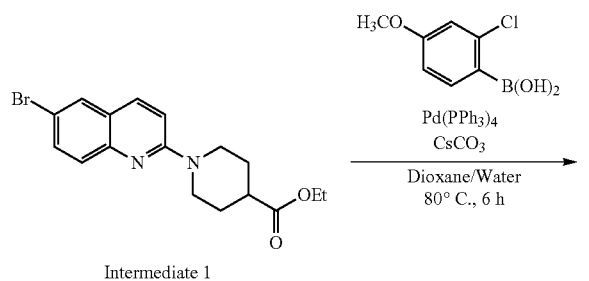

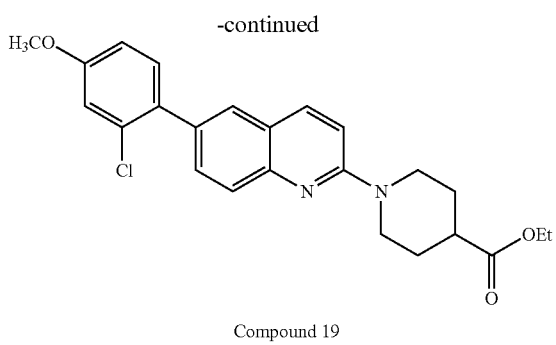

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (2-chloro-4-methoxyphenyl)boronic acid (431 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 19 as a colourless solid (604 mg, 86%).

HPLC-MS [M+H]$^+$ 425.18; MP: 132-135° C.; $^1$H NMR (400 MHz, CDCl$_3$) δ 7.89 (d, J=9.2 Hz, 1H), 7.75-7.68 (m, 1H), 7.65-7.57 (m, 2H), 7.33 (d, J=8.5 Hz, 1H), 7.07-6.98 (m, 21H), 6.92-6.85 (m, 1H), 4.48 (dt, J=13.5, 3.9 Hz, 2H), 4.16 (q, J=7.1 Hz, 2H), 3.85 (s, 3H), 3.12 (ddd, J=13.9, 11.6, 2.9 Hz, 2H), 2.59 (tt, J=11.1, 4.0 Hz, 1H), 2.09-2.00 (m, 2H), 1.39-1.74 (m, 21H), 1.27 (1, J=7.1 Hz, 3H); $^{13}$C NMR (101 MHz, CDCl$_3$) δ 174.74, 159.21, 157.48, 147.15, 137.52, 133.16, 133.11, 132.83, 132.04, 131.39, 127.71, 126.03, 122.51, 115.10, 113.09, 110.05, 60.49, 55.60, 44.91, 41.54, 27.92, 14.24.

In an embodiment, the method of synthesizing Compound 23 (1-(6-(2-chloro-4-methoxyphenyl)quinolin-2-yl)piperidine-4-carboxylic acid) is as follows:

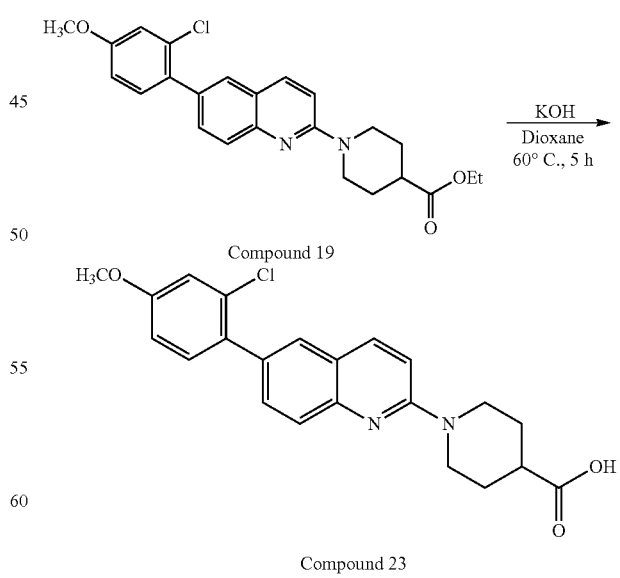

An aqueous solution of potassium hydroxide (5 ml, 5N solution) was added to a solution of compound 19 (ethyl 1-(6-(2-chloro-4-methoxyphenyl)quinolin-2-yl)piperidine- 4-carboxylate) (278 mg, 0.65 mmol) in dioxane (5 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was filtered and evaporated in high vacuum to obtain compound 23 as an off-white solid (204 mg, 79%).

HPLC-MS [M+H]$^+$ 397.17; MP: 190-195° C.; $^1$H NMR (400 MHz, CDCl$_3$) δ 7.90 (d, J=9.0 Hz, 1H), 7.77-7.69 (m, 1H), 7.65-7.58 (m, 2H), 7.33 (d, J=8.5 Hz, 1H), 7.08-6.99 (m, 2H), 6.93-6.82 (m, 1H), 4.47 (dt, J=13.6, 4.0 Hz, 2H), 3.85 (s, 3H), 3.16 (ddd, J=13.8, 11.3, 2.9 Hz, 2H), 2.65 (tt, J=11.0, 4.0 Hz, 1H), 2.09-2.02 (m, 2H), 1.91-1.79 (m, 2H); $^{13}$C NMR (101 MHz, CDCl$_3$) δ 180.47, 177.05, 159.23, 157.38, 146.91, 133.27, 132.77, 132.03, 131.51, 127.73, 125.86, 122.53, 115.11, 113.10, 110.11, 55.60, 44.90, 41.15, 27.66.

In an embodiment, the method of synthesizing Compound 20 (ethyl 1-(6-(4-methoxyphenyl)quinolin-2-yl)piperidine-4-carboxylate) is as follows:

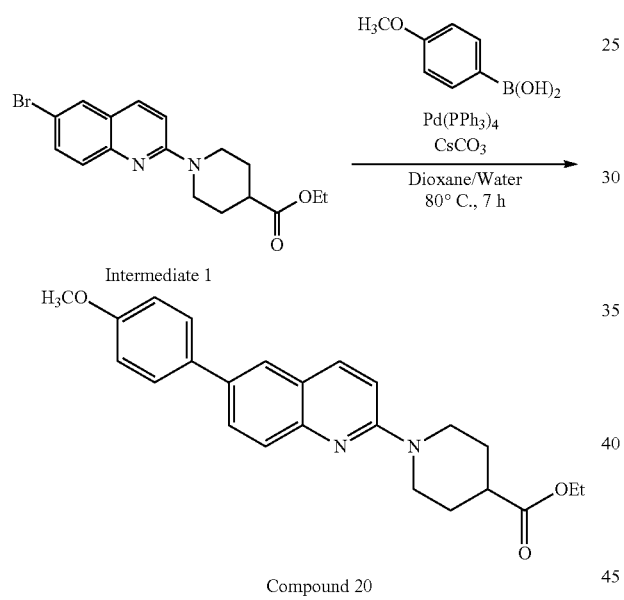

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (4-methoxyphenyl)boronic acid (280 mg, 1.83 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain title Compound 20 as a colourless solid (269 mg, 41%).

HPLC-MS [M+H]$^+$ 391.19; MP: 176-179° C.; $^1$H NMR (400 MHz, CDCl$_3$) δ 7.91 (d, J=9.2 Hz, 1H), 7.81-7.70 (m, 3H), 7.65-7.57 (m, 2H), 7.05-6.96 (m, 3H), 4.47 (dt, J=13.5, 3.9 Hz, 2H), 4.16 (q, J=7.1 Hz, 2H), 3.86 (s, 3H), 3.18-3.06 (m, 2H), 2.59 (tt, J=11.1, 4.0 Hz, 1H), 2.10-1.99 (m, 2H), 1.90-1.75 (m, 2H), 1.27 (t, J=7.1 Hz, 3H); $^{13}$C NMR (101 MHz, CDCl$_3$) δ 174.76, 158.90, 157.26, 147.06, 137.51, 134.69, 133.54, 128.77, 128.02, 126.93, 124.35, 123.11, 114.24, 110.14, 60.49, 55.37, 44.90, 41.53, 27.95, 14.24.

In an embodiment, the method of synthesizing Compound 21 (1-(6-(4-methoxyphenyl)quinolin-2-yl)piperidine-4-carboxylic acid is as follows:

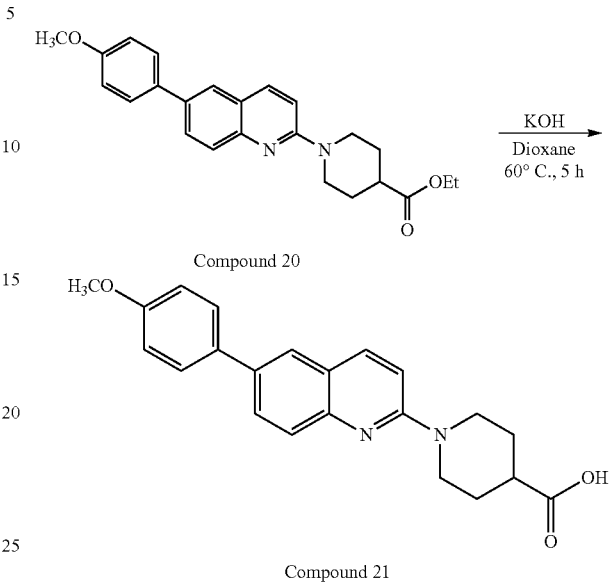

An aqueous solution of potassium hydroxide (3 ml, 5N solution) was added to a solution of compound 20 (ethyl 1-(6-(4-methoxyphenyl)quinolin-2-yl)piperidine-4-carboxylate) (167 mg, 0.43 mmol) in dioxane (3 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain compound 21 as a pale yellow solid (106 mg, 68%).

HPLC-MS [M+H]$^+$ 363.18; MP: not applicable (oil); $^1$H NMR (400 MHz, DMSO-d6) δ 12.23 (bs, 1H), 8.09 (d, J=9.3 Hz, 1H), 7.95 (d, J=2.1 Hz, 1H), 7.86-7.80 (m, 1H), 7.73-7.66 (m, 2H), 7.63 (d, J=8.7 Hz, 1H) 7.29 (d, J=9.3 Hz, 1H), 7.08-6.99 (m, 2H), 4.43 (dt, J=13.3, 3.8 Hz, 2H), 3.80 (s, 3H), 3.16-3.05 (m, 2H), 2.57 (tt, J=10.9, 3.9 Hz, 1H), 1.96-1.88 (m, 2H), 1.66-1.51 (m, 2H); $^{13}$C NMR (126 MHz, DMSO-d6) δ 176.20, 159.18, 156.20, 145.60, 138.42, 134.05, 132.71, 128.69, 128.03, 124.53, 123.15, 114.92, 111.17, 55.67, 44.81, 40.89, 28.07.

In an embodiment, the method of synthesizing Compound 30 (ethyl 1-(6-(3-methoxyphenyl)quinolin-2-yl)piperidine-4-carboxylate) is as follows:

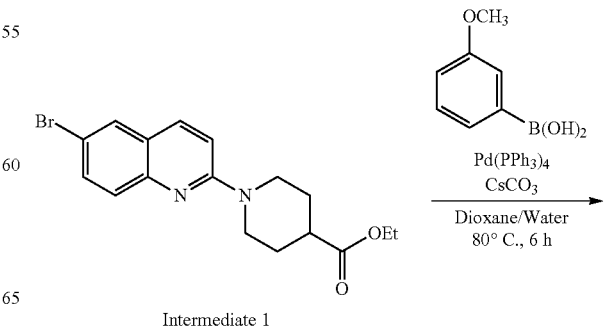

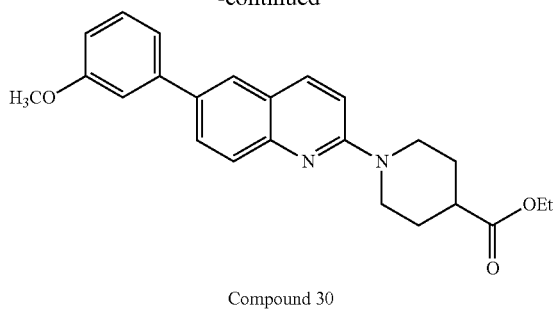

Compound 30

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (3-methoxyphenyl)boronic acid (280 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 30 as an off-white solid (313 mg, 48%).

HPLC-MS [M+H]+ 391.22; MP: 104-107° C.; $^1$H NMR (400 MHz, CDCl$_3$) δ 7.93 (d, J=9.1 Hz, 1H), 7.88-7.66 (m, 3H), 7.42-7.33 (m, 1H), 7.27-7.20 (m, 2H), 7.02 (d, J=9.2 Hz, 1H), 6.96-6.81 (m, 1H), 4.48 (dt, J=13.4, 3.9 Hz, 2H), 4.16 (q, J=7.1 Hz, 2H), 3.89 (s, 3H), 3.19-3.07 (m, 2H), 2.68-2.53 (m, 1H), 2.05 (dd. J=13.5, 3.7 Hz, 2H), 1.90-1.75 (m. 2H), 1.27 (t, J=7.2 Hz, 3H); $^{13}$C NMR (101 MHz, CDCl$_3$) δ 174.74, 160.00, 157.37, 147.51, 142.48, 137.64, 134.84, 129.76, 128.96, 126.95, 125.13, 122.99, 119.57, 112.71, 112.38, 110.16, 60.50, 55.34, 51.78, 44.86, 41.52, 27.93.

In an embodiment, the method of synthesizing Compound 22 (1-(6-(3-methoxyphenyl)quinolin-2-yl)piperidine-4-carboxylic acid) is as follows:

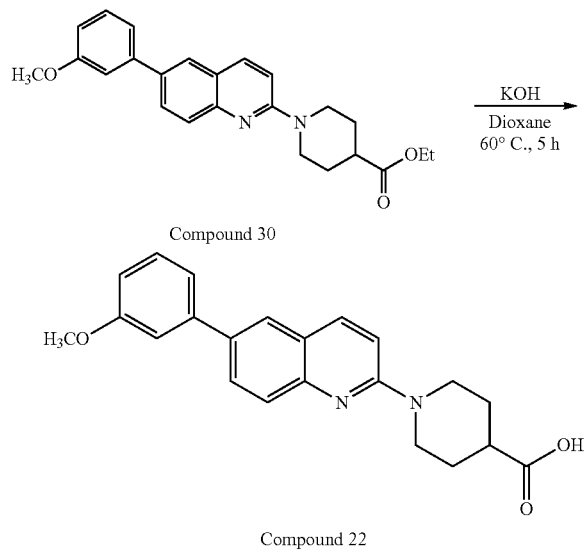

An aqueous solution of potassium hydroxide (3 ml, 5N solution) was added to a solution of compound 30 (ethyl 1-(6-(3-methoxyphenyl)quinolin-2-yl)piperidine-4-carboxylate) (163 mg, 0.42 mmol) in dioxane (3 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na$_2$SO$_4$, was subsequently filtered and evaporated in high vacuum to obtain compound 22 as an off-white solid (134 mg, 88%).

HPLC-MS [M+H]+ 363.18; MP: 200-205° C.; $^1$H NMR (400 MHz, DMSO-d6) δ 12.21 (bs, 1H), 8.12 (d, J=9.1 Hz, 1H), 8.07-9.01 (m, 1H), 7.88 (d, J=8.8 Hz, 1H), 7.72-7.61 (m, 1H), 7.43-7.34 (m, 1H), 7.36-7.25 (m, 3H), 6.97-6.89 (m, 1H), 4.44 (dt, J=13.3, 3.8 Hz, 2H), 3.84 (s, 3H), 3.20-3.05 (m, 2H), 2.64-2.53 (m, 1H), 1.94 (dd, J=13.6, 3.7 Hz, 2H), 1.66-1.51 (m, 2H); $^{13}$C NMR (126 MHz, DMSO-d6) δ 176.17, 160.34, 157.20, 145.40, 141.76, 138.60, 134.19, 130.43, 129.03, 125.50, 123.00, 119.34, 113.23, 112.49, 111.25, 55.65, 44.87, 40.84, 28.09.

In an embodiment, the method of synthesizing Compound 24 (ethyl 1 (6 (4 methoxy 2 (trifluoromethyl)phenyl)quinolin-2-yl)piperidine-4-carboxylate hydrochloride) is as follows:

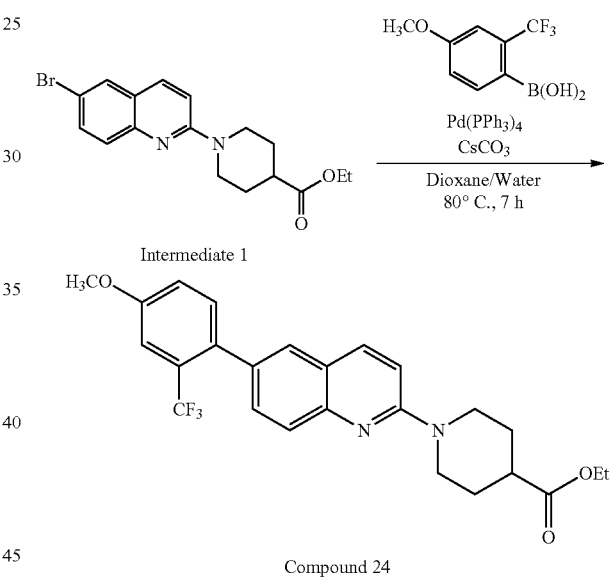

Compound 24

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (4-methoxy-2-(trifluoromethyl)phenyl)boronic acid (402 mg, 1.83 mmol) and caesium carbonate (3 ml, 3M solution) In a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain Compound 24 as an off-white solid (245 mg, 30%).

HPLC-MS [M+H]+ 459.19; MP: 134-137° C.; $^1$H NMR (400 MHz, CD$_3$OD) δ 8.43 (d, J=9.7 Hz, 1H), 7.99 (d, J=8.6 Hz, 1H), 7.86-7.83 (m, 1H), 7.80-7.72 (m, 1H), 7.59 (d, J=9.8 Hz, 1H), 7.43-7.32 (m, 2H), 7.32-7.23 (m, 1H), 4.42 (dt, J=13.8, 4.2 Hz, 2H), 4.21 (q, J=7.1 Hz, 2H), 3.94 (s, 3H), 3.66 (ddd, J=14.0, 11.0, 3.1 Hz, 2H), 2.90 (tt, J=10.3, 4.4 Hz, 1H), 2.29-2.18 (m, 2H), 2.04-1.89 (m, 2H), 1.30 (t, J=7.1 Hz, 3H); $^{13}$C NMR (101 MHz, CD$_3$OD) δ 173.84, 159.52, 151.72, 143.17, 137.33, 136.02, 134.05, 133.39, 131.04, 128.58, 125.29, 122.57, 120.64, 116.77, 116.58, 112.31, 111.78, 60.58, 54.86, 46.29, 39.39, 27.34, 13.09.

In an embodiment, the method of synthesizing Compound 28 (1-(6-(4-methoxy-2-(trifluoromethyl)phenyl)quinolin-2-yl)piperidine-4-carboxylic acid) is as follows:

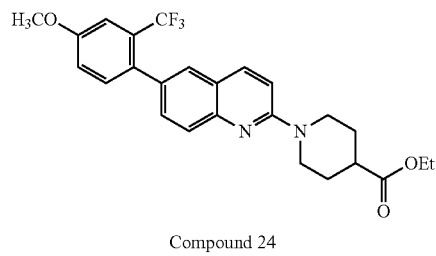

Compound 24

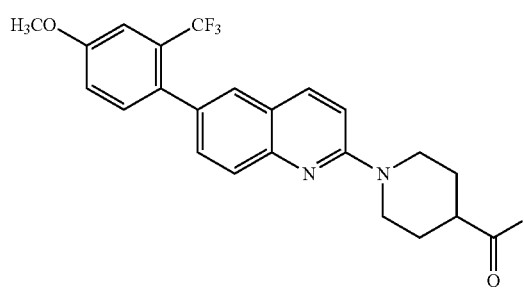

Compound 28

An aqueous solution of potassium hydroxide (3 ml, 5N solution) was added to a solution of compound 24 (ethyl 1-(6-(4-methoxy-2-(trifluoromethyl)phenyl)quinolin-2-yl) piperidine-4-carboxylate hydrochloride) (163 mg, 0.35 mmol) in dioxane (3 ml). The mixture was allowed to stir at 60° C. for a duration of 5 hours. The dioxane was evaporated and the resulting aqueous mixture was acidified with a 37% hydrochloric acid solution. The aqueous solution was extracted with EtOAc, the organic layer was dried with anhydrous Na₂SO₄, was subsequently filtered and evaporated in high vacuum to obtain compound 28 as a pale yellow solid (72 mg, 48%).

HPLC-MS [M+H]⁺ 431.16; MP: 215-217° C.; ¹H NMR (400 MHz, DMSO-d6) δ 12.24 (bs, 1H), 8.15 (bs, 1H), 7.73-7.63 (m, 2H), 7.54-7.56 (m, 1H), 7.41 (d, J=8.3 Hz, 2H), 7.36-7.25 (m, 2H), 4.45 (dt, J=13.7, 3.9 Hz, 2H), 3.90 (s, 3H), 3.26-3.13 (m, 2H), 2.68-2.55 (m, 1H), 2.01-1.93 (m, 2H), 1.69-1.57 (m, 2H); ¹³C NMR (126 MHz, DMSO-d6) δ 176.15, 158.93, 134.33, 132.77, 128.61, 128.38, 128.05, 127.65, 125.47, 123.29, 121.94, 117.92, 112.09, 112.04, 56.16, 45.30, 40.65, 28.04.

In an embodiment, the method of synthesizing Compound 25 (ethyl 1-(6-(3-(trifluoromethoxy)phenyl)quinolin-2-yl) piperidine-4-carboxylate) is as follows:

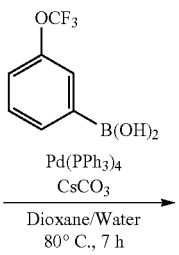

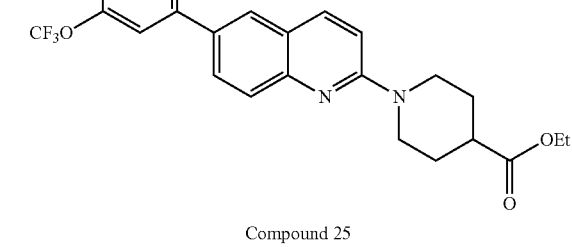

Intermediate 1

Compound 25

Tetrakis(triphenylphosphine)palladium(0) (103 mg, 0.09 mmol) was added to a stirring suspension of intermediate 1 (ethyl 1-(6-bromoquinolin-2-yl)piperidine-4-carboxylate) (650 mg, 1.79 mmol), (3-(trifluoromethoxy)phenyl)boronic acid (375 mg, 1.97 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain Compound 25 as a colourless solid (402 mg, 25%).

HPLC-MS [M+H]⁺ 445.18; MP: 128-129° C.; ¹H NMR (400 MHz, CDCl₃) δ 7.92 (d, J=9.2 Hz, 1H), 7.79-7.73 (m, 3H), 7.72-7.63 (m, 2H), 7.34-7.25 (m, 2H), 7.03 (d, J=9.2 Hz, 1H), 4.49 (dt, J=13.5, 4.0 Hz, 2H), 4.17 (q, J=7.1 Hz, 2H), 3.14 (ddd, J=13.8, 11.4, 2.8 Hz, 2H), 2.60 (tt, J=11.0, 4.0 Hz, 1H), 2.05 (dt, J=12.3, 3.8 Hz, 2H), 1.82 (dtd, J=13.3, 11.2, 4.0 Hz, 2H), 1.27 (t, J=7.1 Hz, 3H); ¹³C NMR (101 MHz, CDCl₃) δ 174.70, 157.40, 148.36, 139.75, 137.60, 133.53, 128.69, 128.26, 127.13, 125.18, 122.97, 121.82, 121.28, 119.26, 110.30, 60.52, 44.82, 41.48, 27.94, 14.24.

In an embodiment, the method of synthesizing Compound 29 (1-(6-(3-(trifluoromethoxy)phenyl)quinolin-2-yl)piperidine-4-carboxylic acid) is as follows:

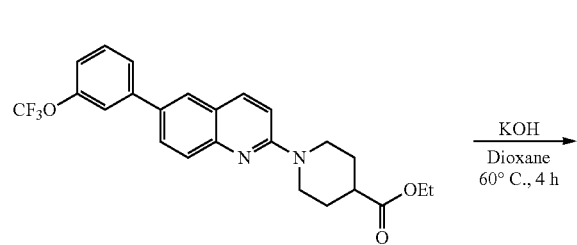

Compound 25

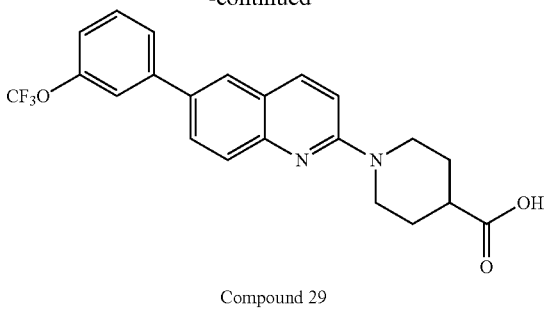

Compound 29

An aqueous solution of potassium hydroxide (5 ml, 5N solution) was added to a solution of compound 25 (ethyl 1-(6-(3-(trifluoromethoxy)phenyl)quinolin-2-yl)piperidine-4-carboxylate) (208 mg, 0.47 mmol) in dioxane (5 ml). The mixture was allowed to stir at 60° C. for a duration of 4 hours. The dioxane was evaporated and the resulting aqueous mixture was acidified with a 37% hydrochloric acid solution at 0° C. The product was precipitated and Compound 29 was isolated as a colourless solid (187 mg, 100%).

HPLC-MS [M+H]$^+$ 417.16; MP: 261-264° C.; $^1$H NMR (500 MHz, DMSO-d6) δ 8.43 (d, J=9.7 Hz, 1H), 8.34-8.30 (m, 1H), 8.26 (d, J=8.6 Hz, 1H), 8.19-8.12 (m, 1H), 7.85 (d, J=7.9 Hz, 1H), 7.78 (s, 1H), 7.70-7.61 (m, 2H), 7.43 (d, J=8.6 Hz, 1H), 4.51-4.44 (m, 2H), 3.59-3.49 (m, 2H), 2.74 (tt, J=10.5, 2.9 Hz, 1H), 2.06 (m, 2H), 1.81-1.70 (m, 2H); $^{13}$C NMR (126 MHz, DMSO-d6) δ 175.64, 149.54, 142.75, 141.40, 134.96, 131.55, 131.14, 126.57, 126.27, 121.64, 120.61, 119.71, 119.58, 113.53, 46.88, 40.11, 27.98.

In an embodiment, the method of synthesizing Compound 26 (ethyl 1-(6-(3-hydroxyphenyl)quinolin-2-yl)piperidine-4-carboxylate) is as follows:

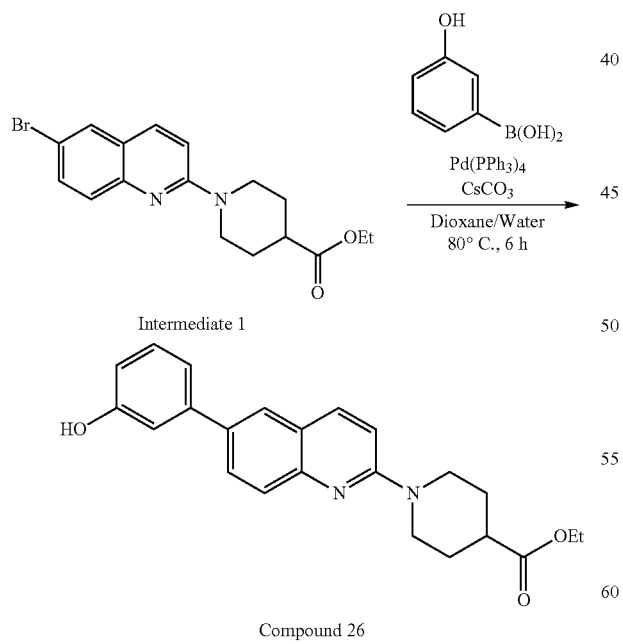

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (3-hydroxyphenyl)boronic acid (252 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 26 as an off-white solid (486 mg, 78%).

HPLC-MS [M+H]J 377.25; MP: 153-155° C.; $^1$H NMR (400 MHz, DMSO-d6) δ 9.51 (s, 1H), 8.10 (d, J=9.2 Hz, 1H), 7.94 (d, J=2.1 Hz, 1H), 7.82-7.75 (m, 1H), 7.62 (d, J=8.7 Hz, 1H), 7.29-7.25 (m, 1H), 7.20-7.07 (m, 2H), 6.80-6.72 (m, 1H), 4.44 (dt, J=13.2, 3.8 Hz, 21H), 4.08 (q, J=7.1 Hz, 2H), 3.16-3.04 (m, 21H), 2.67 (ddt, J=11.1, 7.1, 4.0 Hz, 1H), 1.98-1.88 (m, 2H), 1.66-1.51 (m, 21H), 1.19 (t, J=7.1 Hz, 3H); $^{13}$C NMR (101 MHz, DMSO-d6) δ 174.57, 158.89, 158.31, 141.74, 134.20, 130.38, 128.71, 125.22, 123.13, 117.74, 114.52, 113.75, 111.11, 106.63, 102.92, 60.39, 44.54, 40.93, 27.97, 14.56.

In an embodiment, the method of synthesizing Compound 27 (1-(6-(3-hydroxyphenyl)quinolin-2-yl)piperidine-4-carboxylic acid is as follows:

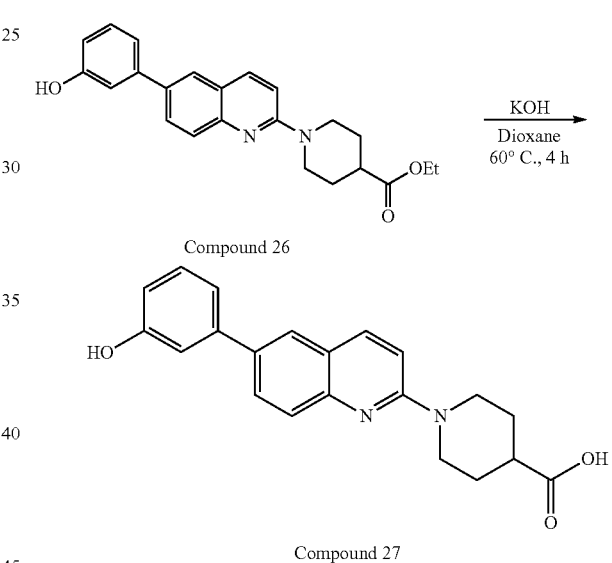

An aqueous solution of potassium hydroxide (5 ml, 5N solution) was added to a solution of compound 26 (ethyl 1-(6-(3-hydroxyphenyl)quinolin-2-yl)piperidine-4-carboxylate) (281 mg, 0.75 mmol) in dioxane (5 ml). The mixture was allowed to stir at 60° C. for a duration of 4 hours. The dioxane was evaporated and the aqueous mixture was acidified with acetic acid to give a suspension. Product was isolated by filtration, was washed with water and was dried in high vacuum at 40° C. Compound 27 was isolated as a pale yellow solid (250 mg, 96%).

HPLC-MS [M+H]$^+$ 349.14; MP: 316-319° C.; $^1$H NMR (400 MHz, DMSO-d6) δ 12.90 (bs, 1H), 9.70 (bs, 1H), 8.43 (d, J=9.6 Hz, 1H), 8.30 (bs, 1H), 8.18-8.13 (m, 1H), 8.02 (d, J=8.8 Hz, 1H), 7.61 (d, J=9.8 Hz, 1H), 7.32-7.28 (m, 1H), 7.19-7.11 (m, 2H), 6.83 (d, J=8.0, 1H), 4.58-4.45 (m, 2H), 3.56-3.50 (m, 2H), 2.73 (tt, J=10.7, 4.1 Hz, 1H), 2.07-2.01 (m, 2H), 1.79-1.70 (m, 2H); $^{13}$C NMR (126 MHz, DMSO-d6) δ175.64, 158.51, 152.30, 140.39, 137.20, 131.21, 130.55, 125.95, 121.65, 117.87, 115.38, 114.01, 113.27, 47.11, 39.04, 28.05.

In an embodiment, the method of synthesizing Compound 31 (ethyl 1-(6-(4-(trifluoromethyl)phenyl)quinolin-2-yl)piperidine-4 carboxylate) is as follows:

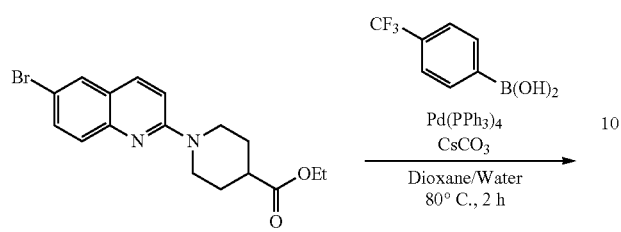

Intermediate 1

Compound 31

Tetrakis(triphenylphosphine)palladium(0) (75 mg, 0.05 mmol) was added to a stirring suspension of intermediate 1 (ethyl 1-(6-bromoquinolin-2-yl)piperidine-4-carboxylate) (500 mg, 1.3 mmol), (4-(trifluoromethyl)phenyl)boronic acid (280 mg, 1.5 mmol) and caesium carbonate (2.5 ml, 3M solution) in a mixture of dioxane (13 ml) and water (2.1 ml). The suspension was allowed to stir at 80° C. for a duration of 2 hours. The solvent was evaporated in high vacuum and the residue was purified by column chromatography (silica gel, Petrol ether/EtOAc 8:1-2:1) to obtain Compound 31 as an off-white solid (380 mg, 70%).

HPLC-MS [M+H]$^+$ 429.22; MP: 175-177° C.; $^1$H NMR (400 MHz, CDCl$_3$) δ 7.93 (d, J=9.2 Hz, 1H), 7.84-7.73 (m, 5H), 7.72-7.68 (m, 2H), 7.04 (d, J=9.2 Hz, 1H), 4.49 (dt, J=13.7, 3.9 Hz, 2H), 4.17 (q, J=7.2 Hz, 2H), 3.20-3.08 (m, 2H), 2.61 (tt, J=11.0, 4.0 Hz, 1H), 2.06 (dt, J=13.4, 3.9 Hz, 2H), 1.82 (dtd, J=13.3, 11.2, 4.0 Hz, 2H), 1.27 (t, J=7.1 Hz, 3H); $^{13}$C NMR (101 MHz, CDCl$_3$) δ 174.69, 157.51, 147.88, 144.46, 137.66, 133.30, 129.02, 128.70, 128.62, 127.24, 227.17, 125.69, 125.56, 122.96, 110.34, 60.53, 44.77, 41.47, 27.94, 14.24.

In an embodiment, the method of synthesizing Compound 36 (1-(6-(4-(trifluoromethyl)phenyl)quinolin-2-yl)piperidine-4-carboxylic acid) is as follows:

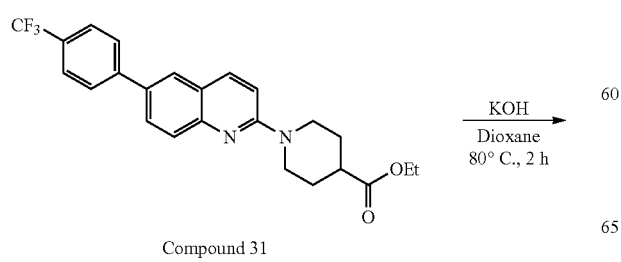

Compound 31

Compound 36

An aqueous solution of potassium hydroxide (5 ml, 5N solution) was added to a solution of compound 31 (ethyl 1-(6-(4-(trifluoromethyl)phenyl)quinolin-2-yl)piperidine-4-carboxylate) (210 mg, 0.4 mmol) in dioxane (5 ml). The mixture was allowed to stir at 80° C. for a duration of 2 hours. The dioxane was evaporated and the resulting aqueous mixture was acidified with 37% hydrochloric acid solution. The aqueous solution was extracted with a mixture of DCM/Isop (7:3), the organic layer was dried with anhydrous Na$_2$SO$_4$, was filtered and evaporated in high vacuum to obtain compound 36 as a colourless solid (100 mg, 60%).

HPLC-MS [M+H]$^+$ 401.19; MP: 278-281° C.; $^1$H NMR (400 MHz, DMSO-d6) δ 13.54 (bs, 1H), 8.55-8.39 (m, 2H), 8.36-8.31 (m, 1H), 8.21-8.12 (m, 1H), 8.01 (d, J=8.2 Hz, 2H), 7.88 (d, J=8.3 Hz, 2H), 7.66 (d, J=9.7 Hz, 1H), 4.62-4.43 (m, 2H), 3.56-3.48 (m, 2H), 2.75 (tt, J=10.6, 4.1 Hz, 1H), 2.05 (dd, J=13.7, 3.9 Hz, 2H), 1.84-1.69 (m, 2H; $^{13}$C NMR (126 MHz, DMSO-d6) δ 175.54, 152.60, 143.09, 142.77, 139.00, 135.98, 135.19, 131.18, 128.75, 128.40, 127.93, 126.77, 126.36, 121.72, 113.52, 47.21, 39.60, 28.06.

In an embodiment, the method of synthesizing Compound 32 (ethyl 1-(6-(3-nitrophenyl)quinolin-2-yl)piperidine-4-carboxylate) is as follows:

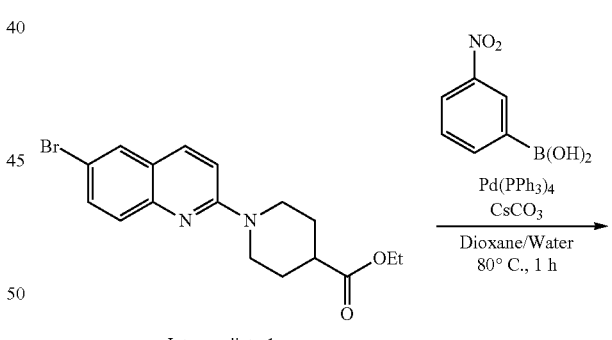

Intermediate 1

Compound 32

Tetrakis(triphenylphosphine)palladium(0) (75 mg, 0.06 mmol) was added to a stirring suspension of intermediate 1

(ethyl 1-(6-bromoquinolin-2-yl)piperidine-4-carboxylate) (500 mg, 1.3 mmol), (3-nitrophenyl)boronic acid (230 mg, 1.4 mmol) and caesium carbonate (2.5 ml, 3M solution) in a mixture of dioxane (13 ml) and water (2.1 ml). The suspension was allowed to stir at 80° C. for a duration of 1 hour. The solvent was evaporated in high vacuum and the residue was purified by column chromatography (silica gel, Petrol ether/EtOAc 2:1) to obtain Compound 32 as a yellow solid (330 mg, 52%).

HPLC-MS [M+H]$^+$ 406.25; MP: 134-137° C.; $^1$H NMR (400 MHz, CDCl$_3$) δ 8.56-8.50 (m, 1H), 8.21-8.14 (m, 1H), 8.02-7.96 (m, 1H), 7.95 (d, J=9.2 Hz, 1H), 7.88-7.72 (m, 3H), 7.66-7.57 (m, 1H), 7.06 (d, J=9.2 Hz, 1H): 4.50 (dt, J=13.4, 3.9 Hz, 2H), 4.17 (q, J=7.1 Hz, 2H), 3.16 (ddd, J=13.9, 11.6, 2.9 Hz, 2H), 2.61 (tt, J=11.0, 4.0 Hz, 1H), 2.06 (dd, J=14.0, 3.3 Hz, 2H), 1.90-1.75 (m, 21H), 1.27 (t, J=7.1 Hz, 3H); $^{13}$C NMR (101 MHz, CDCl$_3$) δ 174.68, 157.57, 148.79, 148.02, 142.65, 137.68, 132.79, 132.15, 129.69, 128.32, 127.41, 125.58, 122.98, 121.68, 121.56, 110.48, 60.55, 44.73, 41.45, 27.94, 14.24.

In an embodiment, the method of synthesizing Compound 39 (1-(6-(3-nitrophenyl)quinolin-2-yl)piperidine-4-carboxylic acid) is as follows:

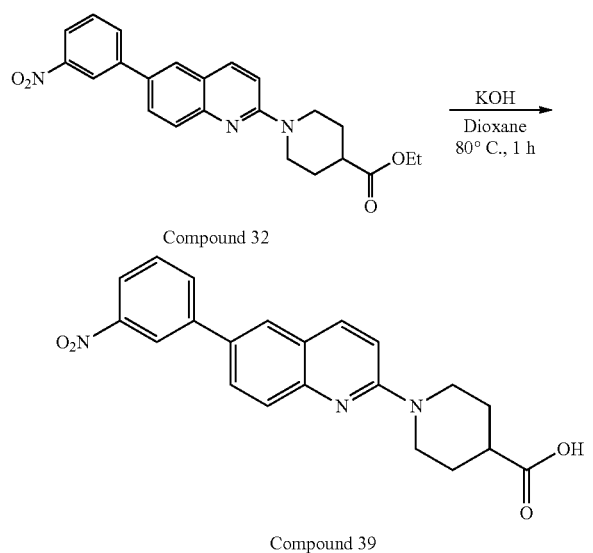

An aqueous solution of potassium hydroxide (3.8 ml, 5N solution) was added to a solution of compound 32 (ethyl 1-(6-(3-nitrophenyl)quinolin-2-yl)piperidine-4-carboxylate) (150 mg, 0.3 mmol) in dioxane (3.8 ml). The mixture was allowed to stir at 60° C. for a duration of 1 hour. The dioxane was evaporated and the resulting aqueous mixture was acidified with a 37% Hydrochloric acid solution. The aqueous solution was extracted with a mixture of DCM/Isop (7:3), the organic layer was dried with anhydrous Na$_2$SO$_4$, was filtered and evaporated in high vacuum to obtain compound 39 as an off-white solid (100 mg, 66%).

HPLC-MS [M+H]$^+$ 378.2; MP: 282-286° C.; $^1$H NMR (400 MHz, DMSO-d6) δ 13.58 (bs, 1H), 8.59-8.53 (m, 1H), 8.53-8.31 (m, 3H), 8.30-8.24 (m, 2H), 8.24-8.18 (m, 1H), 7.86-7.77 (m, 1H), 7.70-7.61 (m, 1H), 4.64-4.42 (m, 2H), 3.61-3.41 (m, 2H), 2.75 (tt, J=10.2, 4.0 Hz, 1H), 2.05 (dd, J=13.8, 4.0 Hz, 2H), 1.84-1.65 (m, 2H); $^{13}$C NMR (126 MHz, DMSO-d6) δ 175.66, 151.80, 148.93, 140.63, 134.25, 133.61, 131.14, 126.79, 122.90, 121.68, 121.46, 114.15, 113.56, 47.12, 40.60, 28.07.

In an embodiment, the method of synthesizing Compound 33 (ethyl 1-(6-(4-fluorophenyl)quinolin-2-yl)piperidine-4-carboxylate) is as follows:

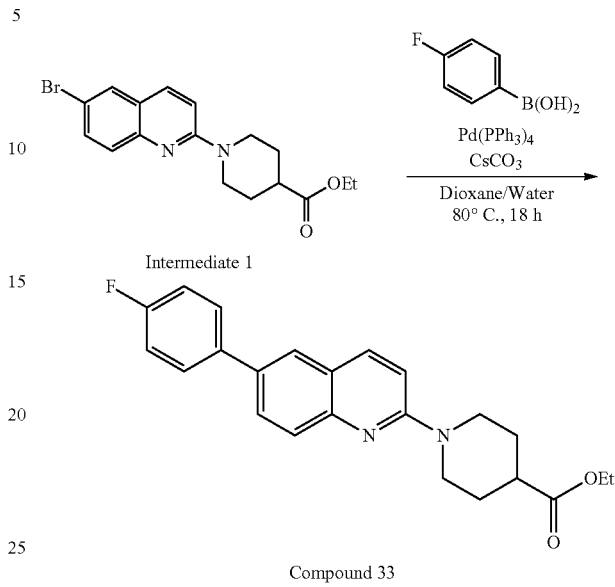

Tetrakis(triphenylphosphine)palladium(0) (75 mg, 0.06 mmol) was added to a stirring suspension of intermediate 1 (ethyl 1-(6-bromoquinolin-2-yl)piperidine-4-carboxylate) (500 mg, 1.3 mmol), (4-fluorophenyl)boronic acid (200 mg, 1.5 mmol) and caesium carbonate (2.5 ml, 3M solution) in a mixture of dioxane (13 ml) and water (2.1 ml). The suspension was allowed to stir at 80° C. for a duration of 18 hours. The solvent was evaporated in high vacuum and the residue was purified by column chromatography (silica gel, Petrol ether/EtOAc 4:1-1:1) to obtain Compound 33 as a colourless solid (190 mg, 40%).

HPLC-MS [M+H]$^+$ 379.23; MP: 144-146° C.; $^1$H NMR (400 MHz, CDCl$_3$) δ 7.91 (d, J=9.2 Hz, 1H), 7.80-7.71 (m, 3H), 7.67-7.56 (m, 2H), 7.19-7.08 (m, 2H), 7.02 (d, J=9.2 Hz, 1H), 4.48 (dt, J=13.5, 3.9 Hz, 2H), 4.16 (q, J=7.1 Hz, 2H), 3.13 (ddd, J=13.9, 11.6, 2.9 Hz, 2H), 2.60 (tt, J=11.1, 4.0 Hz, 1H), 2.11-1.99 (m, 2H), 1.90-1.75 (m, 2H), 1.27 (t, J=7.1 Hz, 3H); $^{13}$C NMR (101 MHz, CDCl$_3$) δ 174.73, 163.47, 157.36, 147.33, 137.55, 137.08, 134.02, 128.77, 128.56, 128.48, 127.05, 124.91, 123.01, 115.72, 115.51, 110.25, 60.51, 44.84, 41.50, 27.94, 14.24.

In an embodiment, the method of synthesizing Compound 47 (1-(6-(4-fluorophenyl)quinolin-2-yl)piperidine-4-carboxylic acid) is as follows:

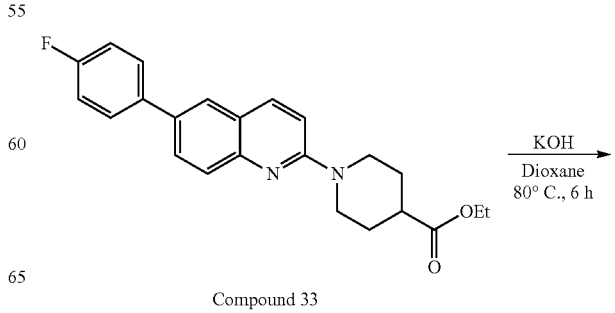

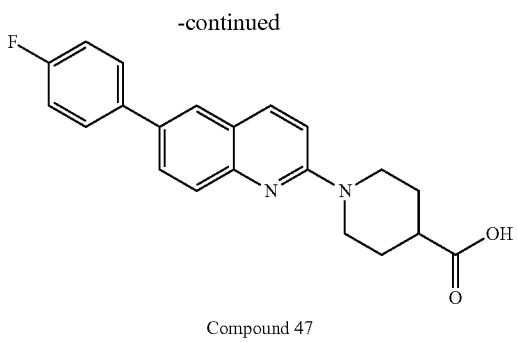

Compound 47

An aqueous solution of potassium hydroxide (11 ml, 5N solution) was added to a solution of compound 33 (ethyl 1 (6 (4 fluorophenyl)quinolin 2 yl)piperidine 4 carboxylate) (350 mg, 0.9 mmol) in dioxane (11 ml). The mixture was allowed to stir at 80° C. for a duration of 6 hours. The dioxane was evaporated and the resulting aqueous mixture was acidified with a 37% Hydrochloric acid solution to give a suspension at 0° C. The product was isolated by filtration, was washed with water and was dried in high vacuum at 40° C. Compound 47 was isolated as a yellow solid (360 mg, 95%).

HPLC-MS [M+H]+ 351.20; MP: 304-308° C.; 1H NMR (400 MHz, DMSO-d6) δ 13.67 (bs, 1H), 8.57-8.39 (m, 2H), 8.22 (bs, 1H), 8.09 (dd, J=8.8 Hz, 1H), 7.88-7.77 (m, 2H), 7.64 (d, J=9.7 Hz, 1H), 7.41-7.30 (m, 2H), 4.66-4.51 (m, 2H), 3.60-3.51 (m, 2H), 2.75 (tt, J=10.7, 4.2 Hz, 1H), 2.04 (dd, J=13.8, 3.8 Hz, 2H), 1.83-1.68 (m, 2H); 13C NMR (101 MHz, DMSO-d6) δ 175.61, 163.76, 161.32, 135.53, 131.16, 129.26, 129.17, 126.03, 121.65, 116.51, 116.30, 113.43, 47.21, 39.66, 28.06.

In an embodiment, the method of synthesizing Compound 34 (ethyl 1-(6-(pyridin-3-yl)quinolin-2-yl)piperidine-4-carboxylate) is as follows:

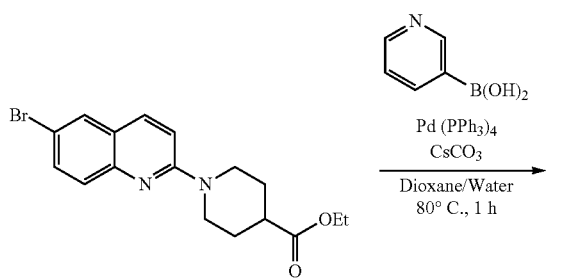

Compound 34

Tetrakis(triphenylphosphine)palladium(0) (75 mg, 0.06 mmol) was added to a stirring suspension of intermediate 1 (ethyl 1-(6-bromoquinolin-2-yl)piperidine-4-carboxylate) (500 mg, 1.3 mmol), pyridine-3-ylboronic acid (180 mg, 1.5 mmol) and caesium carbonate (2.5 ml, 3M solution) in a mixture of dioxane (13 ml) and water (2.1 ml). The suspension was allowed to stir at 80° C. for a duration of 1 hour. The solvent was evaporated in high vacuum and the residue was purified by column chromatography (silica gel, Petrol ether/EtOAc 1:2) to obtain Compound 34 as an off-white solid (240 mg, 46%).

HPLC-MS [M+H]+ 362.25; MP: 106-109° C.; 1H NMR (400 MHz, CDCl3) δ 8.93 (dd, J=2.4, 0.9 Hz, 1H), 8.37 (dd, J=4.8, 1.6 Hz, 1H), 7.99-7.90 (m, 2H), 7.82-7.72 (m, 3H), 7.41-7.33 (m, 1H), 7.04 (d, J=9.2 Hz, 1H), 4.49 (dt, J=13.3, 3.6 Hz, 2H), 4.16 q, J=7.1 Hz, 2H), 3.20-3.08 (m, 2H), 2.60 (tt, J=11.0, 4.0 Hz, 1H), 2.11-2.00 (m, 2H), 1.89-1.78 (m, 2H), 1.27 (t, J=7.1 Hz, 3H); 13C NMR (101 MHz, CDCl3) δ 174.68, 157.48, 148.25, 148.05, 147.79, 137.59, 136.44, 134.13, 131.42, 128.47, 127.40, 125.37, 123.54, 123.04, 110.36, 60.52, 44.76, 41.47, 27.94, 14.24.

In an embodiment, the method of synthesizing Compound 49 (1-(6-(pyridin-3-yl)quinolin-2-yl)piperidine-4-carboxylic acid hydrochloride) is as follows:

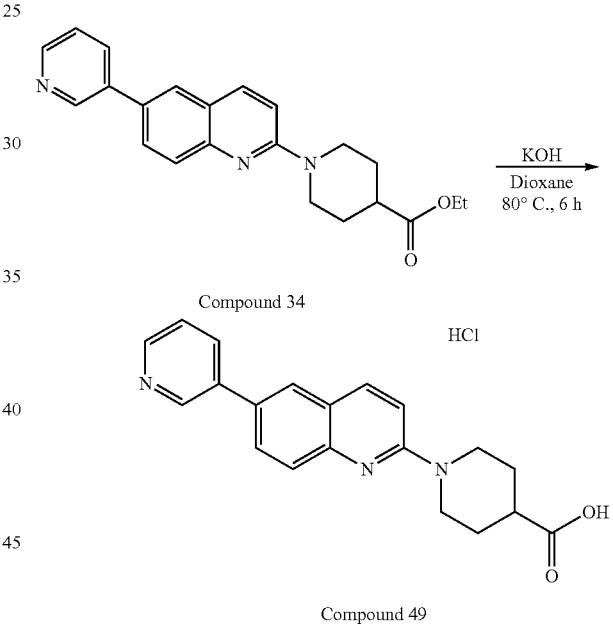

A aqueous solution of potassium hydroxide (6.3 ml, 5N solution) was added to a solution of compound 34 (ethyl 1-(6-(pyridin-3-yl)quinolin-2-yl)piperidine-4-carboxylate) (200 mg, 0.766 mmol) in dioxane (6.3 ml). The mixture was allowed to stir at 80° C. over 6 hours. The dioxane was evaporated and the resulting aqueous mixture was acidified with a 37% Hydrochloric acid solution to give a suspension at 0° C. The product was isolated by filtration, was washed with water and was dried in high vacuum at 40° C. Compound 49 was isolated as a yellow solid (160 mg, 96%).

HPLC-MS [M+H]+ 334.15; MP: 309-313° C.; 1H NMR (400 MHz, DMSO-d6) δ 9.31 (bs, 1H), 8.93-8.81 (m, 2H), 8.63 (d, J=8.8 Hz, 1H), 8.49 (bs, 1H), 8.42 (d, J=9.8 Hz, 1H), 8.31-8.19 (m, 1H), 8.11-7.99 (m, 1H), 7.69 (d, J=9.8 Hz, 1H), 4.65-4.55 (m, 2H), 3.57 (ddd, J=14.0, 11.3, 2.8 Hz, 2H), 2.76 (tt, J=10.5, 4.2 Hz, 1H), 2.05 (dd, J=13.8, 3.8 Hz, 2H), 1.84-1.70 (m, 2H); 13C NMR (101 MHz, DMSO-d6) δ

175.59, 152.01, 142.62, 141.77, 141.65, 137.24, 131.18, 131.01, 127.47, 127.16, 121.56, 119.86, 114.04, 47.39, 40.38, 28.10.

In an embodiment, the method of synthesizing Compound 35 (ethyl 1-(6-(6-fluoropyridin-3-yl)quinolin-2-yl)piperidine-4-carboxylate) is as follows:

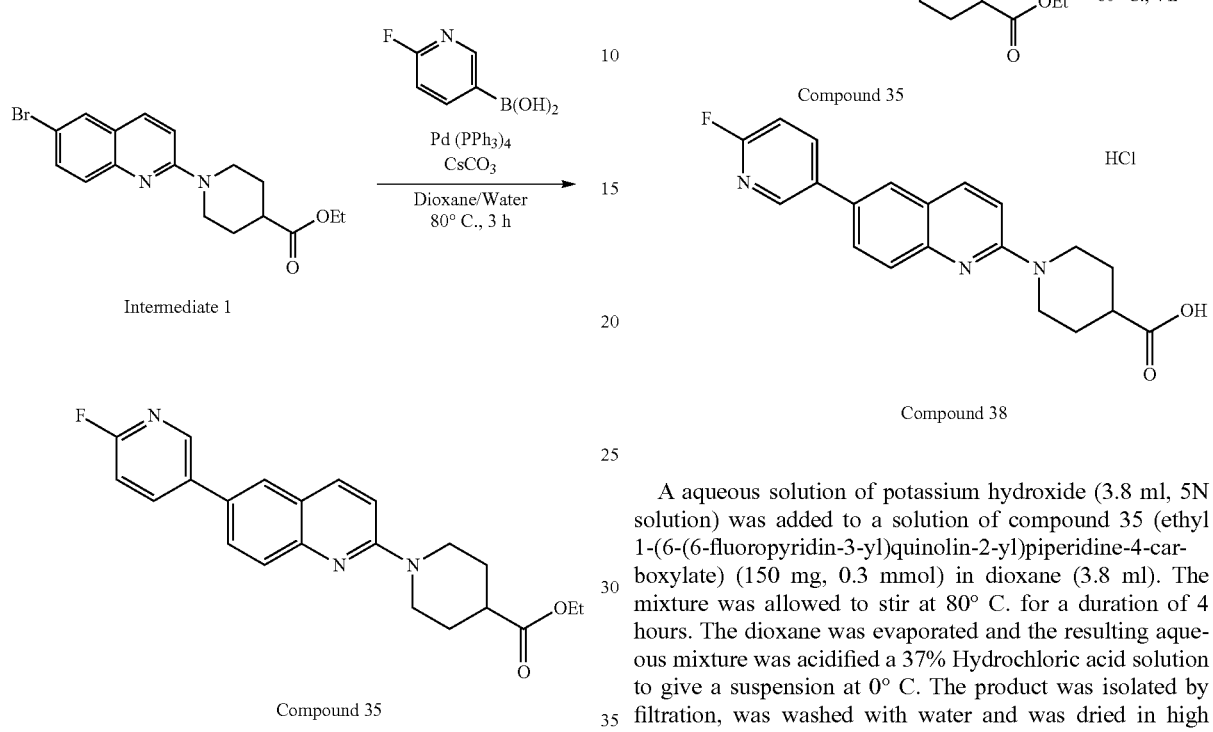

Tetrakis(triphenylphosphine)palladium(0) (75 mg, 0.06 mmol) was added to a stirring suspension of intermediate 1 (ethyl 1-(6-bromoquinolin-2-yl)piperidine-4-carboxylate) (500 mg, 1.3 mmol), (6-fluoropyridin-3-yl)boronic acid (211 mg, 1.5 mmol) and caesium carbonate (2.5 ml, 3M solution) in a mixture of dioxane (13 ml) and water (2.1 ml). The suspension was allowed to stir at 80° C. for a duration of 3 hours. The solvent was evaporated in high vacuum and the residue was purified by column chromatography (silica gel, Petrol ether/EtOAc 2:1) to obtain Compound 35 as an off-white solid (270 mg, 53%).

HPLC-MS [M+H]⁺ 380.24; MP: 108-110° C.; $^1$H NMR (400 MHz, CDCl$_3$) δ 8.49 (m, 1H), 8.09-7.99 (m, 1H), 7.92 (d, J=9.2 Hz, 1H), 7.81-7.66 (m, 3H), 7.08-6.98 (m, 2H), 4.49 (dt, J=13.5, 3.9 Hz, 2H), 4.16 (q, J=7.1 Hz, 2H), 3.14 (ddd, J=13.8, 11.5, 2.9 Hz, 2H), 2.61 (tt, J=11.0, 4.0 Hz, 1H), 2.11-2.00 (m, 2H), 1.89-1.74 (m, 2H), 1.27 (t, J=7.1 Hz, 3H); $^{13}$C NMR (101 MHz, CDCl$_3$) δ 174.69, 164.05, 157.50, 147.73, 145.67, 139.60, 137.55, 134.73, 130.28, 128.35, 127.42, 125.28, 123.01, 110.48, 109.61, 60.55, 44.76, 41.45, 27.93, 14.23.

In an embodiment, the method of synthesizing Compound 38 (1-(6-(5-fluoropyridin-3-yl)quinolin-2-yl)piperidine-4-carboxylic acid hydrochloride) is as follows:

A aqueous solution of potassium hydroxide (3.8 ml, 5N solution) was added to a solution of compound 35 (ethyl 1-(6-(6-fluoropyridin-3-yl)quinolin-2-yl)piperidine-4-carboxylate) (150 mg, 0.3 mmol) in dioxane (3.8 ml). The mixture was allowed to stir at 80° C. for a duration of 4 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 38 was isolated as an off-white solid (116 mg, 100%).

HPLC-MS [M+H]+ 352.16; MP: 271-274° C.; $^1$H NMR (400 MHz, DMSO-d6) δ 13.68 (bs, 1H), 12.41 (bs, 1H), 8.66 (d, J=2.6 Hz, 1H), 8.63-8.44 (m, 1H), 8.45-8.35 (m, 2H), 8.33-8.28 (m, 1H), 8.18-8.05 (m, 1H), 7.65 (d, J=9.8 Hz, 1H), 7.42-7.31 (m, 1H), 4.78-4.47 (m, 2H), 3.60-3.49 (m, 2H). 2.75 (tt, J=10.7, 4.3 Hz, 1H), 2.04 (dd, J=13.8, 3.9 Hz, 2H), 1.84-1.69 (m, 2H); $^{13}$C NMR (101 MHz, DMSO-d6) δ 175.61, 164.34, 161.99, 146.04, 145.89, 140.83, 133.26, 132.62, 131.12, 126.49, 121.63, 113.65, 110.50, 110.12, 47.21, 39.45, 28.06.

In an embodiment, the method of synthesizing Compound 37 (ethyl 1-(6-(2-fluoropyridin-4-yl)quinolin-2-yl)piperidine-4-carboxylate) is as follows:

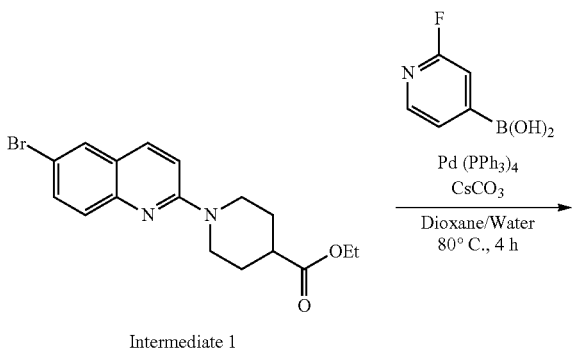

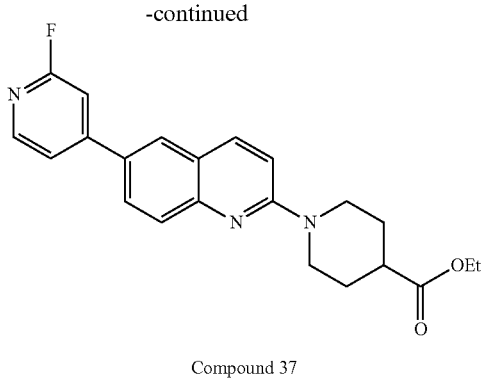

Compound 37

Tetrakis(triphenylphosphine)palladium(0) (75 mg, 0.06 mmol) was added to a stirring suspension of intermediate 1 (ethyl 1-(6-bromoquinolin-2-yl)piperidine-4-carboxylate) (500 mg, 1.3 mmol), (2-fluoropyridin-4-yl)boronic acid (211 mg, 1.5 mmol) and caesium carbonate (2.5 ml, 3M solution) in a mixture of dioxane (13 ml) and water (2.1 ml). The suspension was allowed to stir at 80° C. for a duration of 4 hours. The solvent was evaporated in high vacuum and the residue was purified by column chromatography (silica gel, Petrol ether/EtOAc 2:1) to obtain Compound 37 as an off-white solid (150 mg, 23%).

HPLC-MS [M+H]$^+$ 380.23; MP: 120-121° C.; $^1$H NMR (400 MHz, CDCl$_3$) δ 8.25 (d, J=5.3 Hz, 1H), 7.93 (d, J=9.2 Hz, 2H), 7.88-7.85 (m, 1H), 7.81-7.74 (m, 2H), 7.48 (dt, J=5.3, 1.7 Hz, 1H), 7.20 (bs, 1H), 7.05 (d, J=9.2 Hz, 1H), 4.50 (dt, J=13.9, 4.0 Hz, 2H), 4.16 (q, J=7.1 Hz, 2H), 3.22-3.10 (m, 2H), 2.61 (tt, J=11.0, 4.0 Hz, 1H), 2.05 (dq, J=12.3 Hz, 2H), 1.81 (dtd, J=13.4, 11.2, 4.0 Hz, 2H), 1.77 (t, J=7.1 Hz, 3H); $^{13}$C NMR (101 MHz, CDCl$_3$) δ 174.61, 165.84, 157.68, 153.73, 148.79, 147.96, 137.78, 130.25, 127.83, 127.48, 125.91, 122.79, 119.15, 110.48, 106.36, 60.55, 44.63, 41.41, 27.94, 14.23.

In an embodiment, the method of synthesizing Compound 51 (1-(6-(2-fluoropyridin-4-yl)quinolin-2-yl)piperidine-4-carboxylic acid hydrochloride) is as follows:

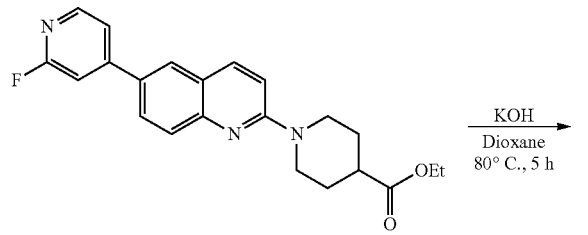

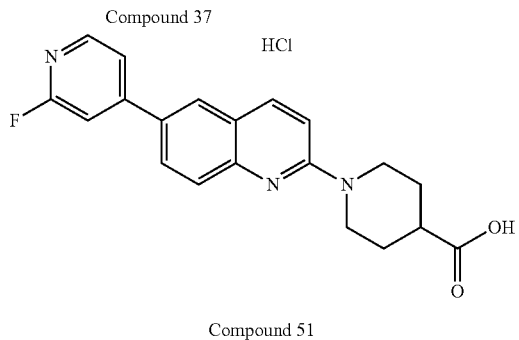

Compound 51

A aqueous solution of potassium hydroxide (15.7 ml, 5N solution) was added to a solution of compound 37 (ethyl 1-(6-(2-fluoropyridin-4-yl)quinolin-2-yl)piperidine-4-carboxylate) (500 mg, 1.3 mmol) in dioxane (15.7 ml). The mixture was allowed to stir at 80° C. for a duration of 5 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 51 was isolated as an off-white solid (509 mg, 100%).

HPLC-MS [M+H]$^+$ 352.13; MP: 326-330° C.; $^1$H NMR (400 MHz, DMSO-d6) δ 13.78 (bs, 1H), 12.39 (bs, 1H), 8.64-8.44 (m, 2H), 8.45-8.33 (m, 2H), 8.29-8.19 (m, 1H), 7.85-7.78 (m, 1H), 7.70-7.59 (m, 2H), 4.69-4.47 (m, 2H), 3.59-3.51 (m, 2H), 2.75 (tt, J=10.7, 4.3 Hz, 1H), 2.04 (dd, J=13.8, 4.0 Hz, 2H), 1.83-1.68 (m, 2H); $^{13}$C NMR (101 MHz, DMSO-d6) δ 175.63, 165.78, 163.45, 152.18, 148.87, 148.71, 130.74, 127.34, 121.59, 119.88, 113.77, 107.09, 106.70, 47.16, 39.76, 32.58, 28.08.

In an embodiment, the method of synthesizing Compound 40 (ethyl 1-(6-(2-methylpyridin-4-yl)quinolin-2-yl)piperidine-4-carboxylate) is as follows:

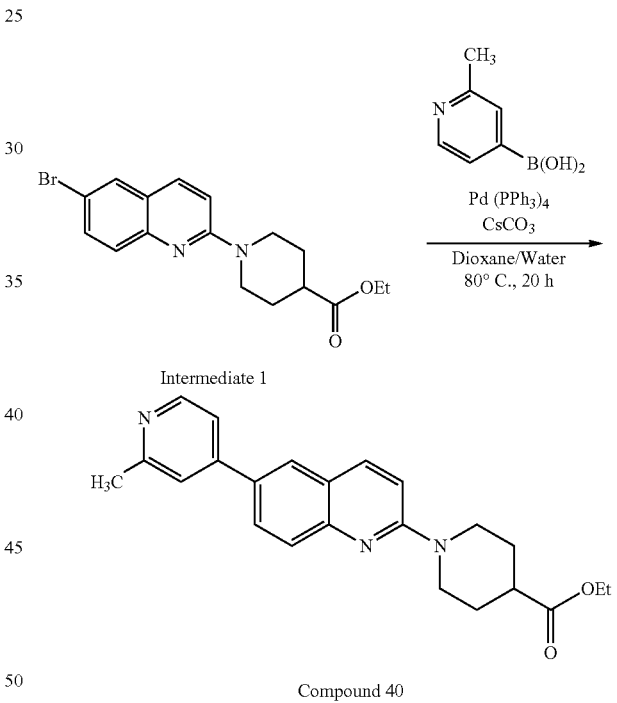

Compound 40

Tetrakis(triphenylphosphine)palladium(0) (100 mg, 0.09 mmol) was added to a stirring suspension of intermediate 1 (ethyl 1-(6-bromoquinolin-2-yl)piperidine-4-carboxylate) (700 mg, 1.9 mmol), (2-methylpyridin-4-yl)boronic acid (290 mg, 2.1 mmol) and caesium carbonate (3.5 ml, 3M solution) in a mixture of dioxane (18 ml) and water (3 ml). The suspension was allowed to stir at 80° C. for a duration of 20 hours. The solvent was evaporated in high vacuum and the residue was purified by column chromatography (silica gel, Petrol ether/EtOAc 1:2) to obtain Compound 40 as a yellow solid (160 mg, 20%).

HPLC-MS [M+H]$^+$ 376.35; MP: 134-135° C.; $^1$H NMR (500 MHz, CDCl$_3$) δ 8.58-8.50 (m, 1H), 7.93 (d, J=9.1 Hz, 1H), 7.86 (d, J=2.1 Hz, 1H), 7.81 (dd, J=8.7, 2.1 Hz, 1H), 7.76 (d, J=8.7 Hz, 1H), 7.47 (s, 1H), 7.43-7.38 (m, 1H), 7.03

(d, J=9.2 Hz, 1H), 4.49 (dt, J=13.6, 3.9 Hz, 2H), 4.16 (q, J=7.1 Hz, 2H), 3.15 (ddd, J=13.9, 11.6, 2.9 Hz, 2H), 2.64 (s, 3H), 2.63-2.57 (m, 1H), 2.09-2.00 (m, 2H), 1.87-1.75 (m, 21H), 1.27 (t, J=7.1 Hz, 3H); $^{13}$C NMR (126 MHz. CDCl$_3$) δ 174.64, 158.62, 157.55, 149.25, 148.63, 148.39, 137.77, 131.66, 128.13, 127.29, 125.64, 122.88, 120.98, 118.65, 110.35, 60.54, 44.72, 41.44, 27.95, 24.46, 14.24.

In an embodiment, the method of synthesizing Compound 53 (1-(6-(2-methylpyridin-4-yl)quinolin-2-yl)piperidine-4-carboxylic acid hydrochloride) is as follows:

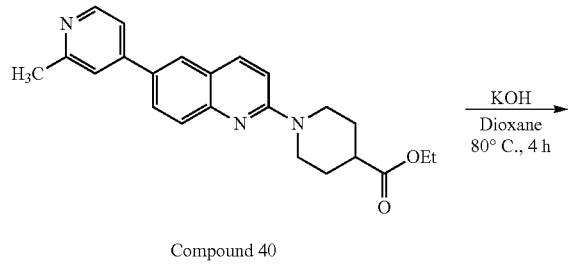

Compound 40

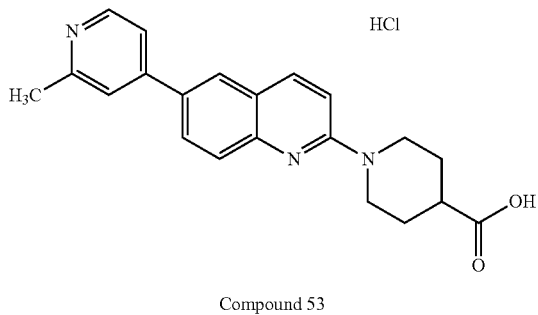

Compound 53

A aqueous solution of potassium hydroxide (8.4 ml, 5N solution) was added to a solution of compound 40 (ethyl 1-(6-(2-methylpyridin-4-yl)quinolin-2-yl)piperidine-4-carboxylate) (270 mg, 0.7 mmol) in dioxane (8.4 ml). The mixture was allowed to stir at 80° C. for a duration of 4 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 53 was isolated as a yellow solid (280 mg, 100%).

HPLC-MS [M+H]$^+$ 348.16; MP: 340-345° C.; $^1$H NMR (400 MHz, DMSO-d6) δ 12.41 (bs, 1H), 8.87-8.80 (m, 1H), 8.68-8.62 (m, 1H), 8.59-8.31 (m, 4H), 8.32-8.25 (m, 1H), 7.65 (d, J=9.7 Hz, 1H), 4.69-4.47 (m, 2H), 3.64-3.54 (m, 2H), 2.82 (s, 3H), 2.74 (tt, J=10.3, 4.1 Hz, 1H), 2.03 (dd, J=13.9, 3.9 Hz, 2H), 1.83-1.62 (m, 2H); $^{13}$C NMR (126 MHz, DMSO-d6) δ 175.75, 154.20, 134.20, 141.50, 141.82, 130.64, 128.78, 124.36, 121.89, 121.21, 113.67, 46.68, 40.54, 28.12, 19.89.

In an embodiment, the method of synthesizing Compound 41 (ethyl 1-(6-(3,5-dimethoxyphenyl)quinolin-2-yl)piperidine-4-carboxylate) is as follows:

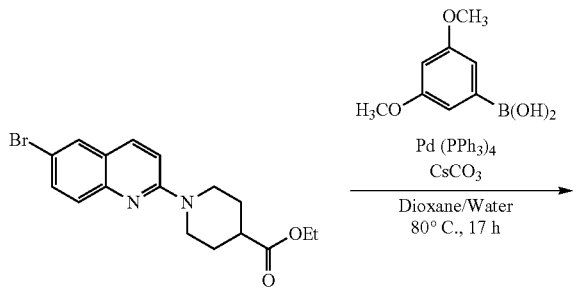

Intermediate 1

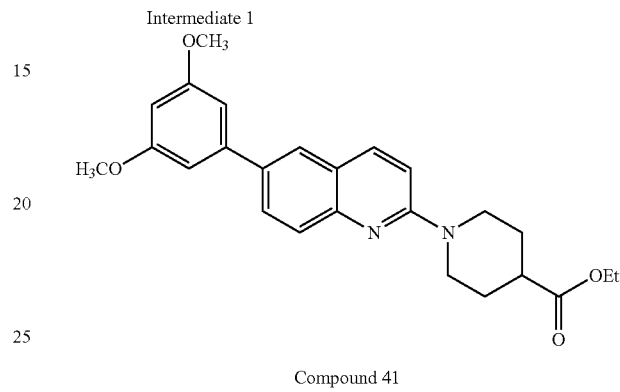

Compound 41

Tetrakis(triphenylphosphine)palladium(0) (100 mg, 0.09 mmol) was added to a stirring suspension of intermediate 1 (ethyl 1-(6-bromoquinolin-2-yl)piperidine-4-carboxylate) (700 mg, 1.9 mmol), (3,5-dimethoxyphenyl)boronic acid (380 mg, 2.1 mmol) and caesium carbonate (3.5 ml, 3M solution) in a mixture of dioxane (18 ml) and water (3 ml). The suspension was allowed to stir at 80° C. for a duration of 17 hours. The solvent was evaporated in high vacuum and the residue was purified by column chromatography (silica gel, Petrol ether/EtOAc 4:1) to obtain Compound 41 as off-white solid (520 mg, 63%).

HPLC-MS [M+H]$^+$ 421.30; MP: 85-87° C.; $^1$H NMR (500 MHz, CDCl$_3$) δ 7.92 (d, J=9.2 Hz, 1H), 7.81-7.71 (m, 3H), 7.02 (d, J=9.2 Hz, 1H), 6.82 (d, J=2.2 Hz, 2H), 6.54-6.43 (m, 1H), 4.48 (dt, J=13.5, 4.1 Hz, 2H), 4.16 (q, J=7.1 Hz, 2H), 3.87 (s, 6H), 3.21-3.08 (m, 2H), 2.60 (tt, J=11.0, 4.0 Hz, 1H), 2.09-2.01 (m, 2H), 1.89-1.76 (m, 2H), 1.27 (t, J=7.1 Hz, 3H); $^{13}$C NMR (126 MHz, CDCl$_3$) δ 174.73, 171.56, 161.12, 157.36, 143.17, 137.70, 134.97, 128.99, 126.85, 125.16, 122.92, 110.20, 105.33, 99.07, 60.52, 55.46, 44.90, 41.49, 27.95, 14.25.

In an embodiment, the method of synthesizing Compound 46 (1-(6-(3,5-dimethoxyphenyl)quinolin-2-yl)piperidine-4-carboxylic acid) is as follows:

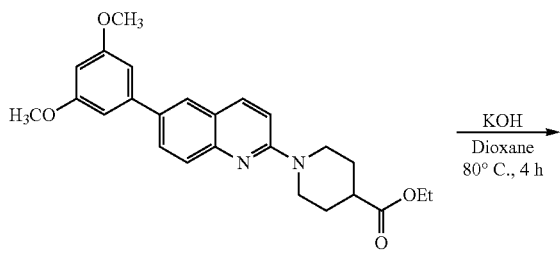

Compound 41

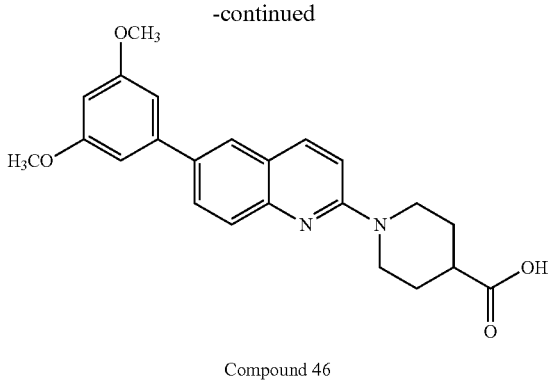

Compound 46

A aqueous solution of potassium hydroxide (5 ml, 5N solution) was added to a solution of compound 41 (ethyl 1-(6-(3,5-dimethoxyphenyl)quinolin-2-yl)piperidine-4-carboxylate) (200 mg, 0.4 mmol) in dioxane (5 ml). The mixture was allowed to stir at 80° C. for a duration of 4 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 46 was isolated as a colourless solid (170 mg, 100%).

HPLC-MS [M+H]$^+$ 393.25; MP: 248-251° C.; $^1$H NMR (400 MHz, DMSO-d6) δ 12.49 (bs, 1H), 8.43 (d, J=9.7 Hz, 1H), 8.33-8.24 (m, 2H), 8.16-8.09 (m, 1H), 7.64 (d, J=9.8 Hz, 1H), 6.92 (d, J=2.2 Hz, 2H), 6.56 (t, J=2.2 Hz, 1H), 4.53-4.45 (m, 2H), 3.84 (s, 6H), 3.53-3.47 (m, 2H), 2.74 (tt, J=10.5, 4.2 Hz, 1H), 2.10-2.00 (m, 2H), 1.83-1.69 (m, 2H); $^{13}$C NMR (126 MHz, DMSO-d6) δ 175.65, 161.46, 151.90, 142.98, 141.05, 136.78, 132.49, 131.38, 126.25, 121.54, 113.31, 105.30, 100.16, 55.85, 47.19, 40.36, 28.07.

In an embodiment, the method of synthesizing Compound 42 (ethyl 1-(6-(1H-indol-5-yl)quinolin-2-yl)piperidine-4-carboxylate) is as follows:

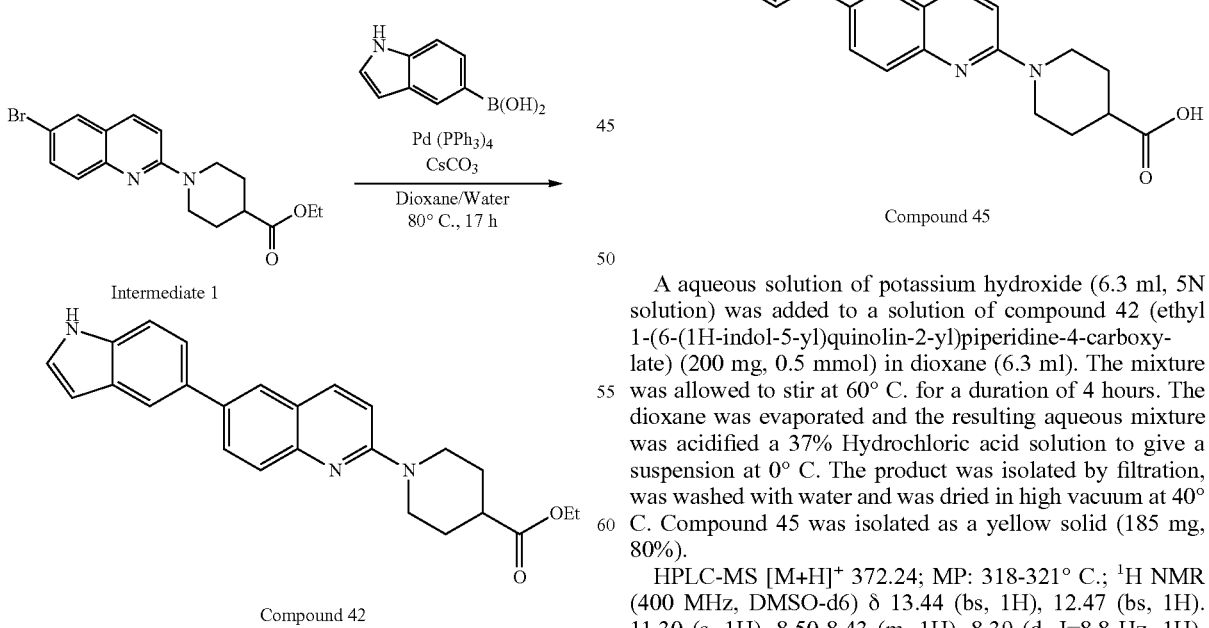

Tetrakis(triphenylphosphine)palladium(0) (100 mg, 0.09 mmol) was added to a stirring suspension of intermediate 1 (ethyl 1-(6-bromoquinolin-2-yl)piperidine-4-carboxylate) (700 mg, 1.9 mmol), (1H-indol-5-yl)boronic acid (330 mg, 2.1 mmol) and caesium carbonate (3.5 ml, 3M solution) in a mixture of dioxane (18 ml) and water (3 ml). The suspension was allowed to stir at 80° C. for a duration of 17 hours. The solvent was evaporated in high vacuum and the residue was purified by column chromatography (silica gel, Petrol ether/EtOAc 4:1) to obtain Compound 42 as a grey solid (470 mg, 57%).

HPLC-MS [M+H]$^+$ 400.22; MP: 159-162° C.; $^1$H NMR (400 MHz, CDCl$_3$) δ 8.27 (bs, 1H), 7.96-7.92 (m, 2H), 7.90 (dd, J=8.7, 2.2 Hz, 1H), 7.84 (d, J=2 Hz, 1H), 7.78 (d, J=8.7 Hz, 1H), 7.58-7.50 (m, 1H), 7.50-7.42 (m, 1H), 7.25-7.23 (m, 1H), 7.02 (d, J=9.2 Hz, 1H), 6.63-6.61 (m, 1H), 4.48 (dt, J=13.7, 3.9 Hz, 2H), 4.17 (q, J=7.1 Hz, 2H), 3.12 (ddd, J=13.3, 11.5, 2.9 Hz, 2H), 2.59 (tt, J=11.1, 4.0 Hz, 1H), 2.11-2.00 (m, 2H), 1.91-1.76 (m, 2H), 1.28 (t, J=7.1 Hz, 3H); $^{13}$C NMR (101 MHz, CDCl$_3$) δ 174.83, 157.25, 146.91, 137.59, 136.52, 135.18, 133.11, 129.60, 128.49, 126.80, 124.89, 124.83, 123.22, 121.87, 119.12, 111.28, 110.10, 102.98, 60.50, 44.98, 41.56, 27.97, 14.25.

In an embodiment, the method of synthesizing Compound 45 (1-(6-(1H-indol-5-yl)quinolin-2-yl)piperidine-4-carboxylic acid hydrochloride) is as follows:

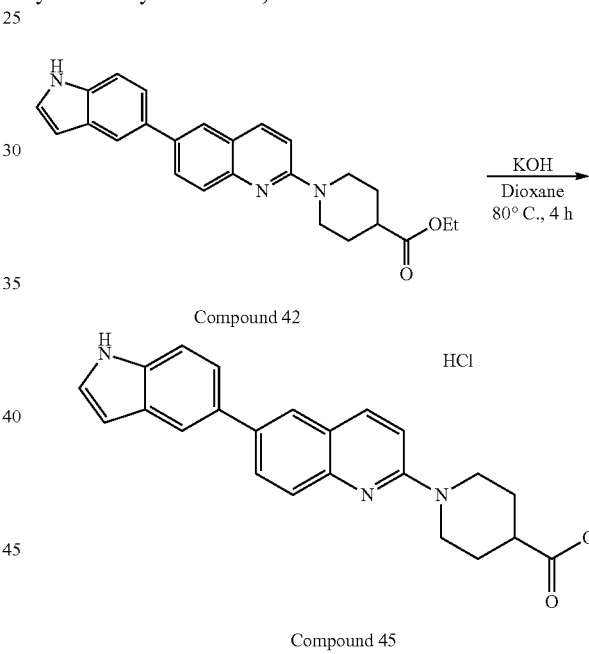

A aqueous solution of potassium hydroxide (6.3 ml, 5N solution) was added to a solution of compound 42 (ethyl 1-(6-(1H-indol-5-yl)quinolin-2-yl)piperidine-4-carboxylate) (200 mg, 0.5 mmol) in dioxane (6.3 ml). The mixture was allowed to stir at 60° C. for a duration of 4 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 45 was isolated as a yellow solid (185 mg, 80%).

HPLC-MS [M+H]$^+$ 372.24; MP: 318-321° C.; $^1$H NMR (400 MHz, DMSO-d6) δ 13.44 (bs, 1H), 12.47 (bs, 1H). 11.30 (s, 1H), 8.50-8.43 (m, 1H), 8.39 (d, J=8.8 Hz, 1H), 8.22 (d, J=2.1 Hz, 1H), 8.18-8.10 (m, 1H), 7.94 (d, J=1.5 Hz, 1H), 7.62 (d, J=9.8 Hz, 1H), 7.57-7.47 (m, 2H), 7.46-7.37 (m, 1H), 6.55-6.49 (m, 1H), 4.56-4.47 (m, 2H), 3.58-3.48

(m, 2H), 2.75 (tt, J=10.5, 4.2 Hz, 1H), 2.11-2.00 (m, 2H), 1.84-1.69 (m, 2H); ¹³C NMR (126 MHz, DMSO-d6) δ 175.65, 151.56, 143.08, 138.90, 136.15, 131.53, 130.01, 128.77, 126.81, 125.48, 121.77, 120.68, 118.79, 113.04, 112.52, 102.04, 47.15, 40.36, 28.06.

In an embodiment, the method of synthesizing Compound 43 (ethyl 1-(6-(6-(trifluoromethyl)pyridin-3-yl)quinolin-2-yl)piperidine-4-carboxylate) is as follows:

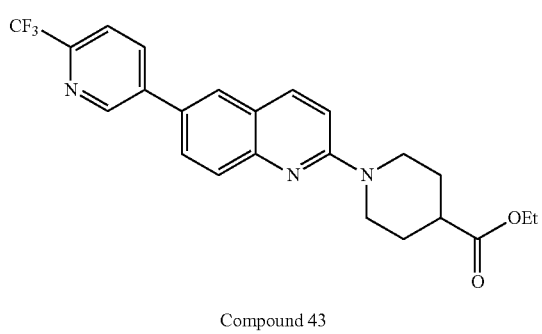

Intermediate 1

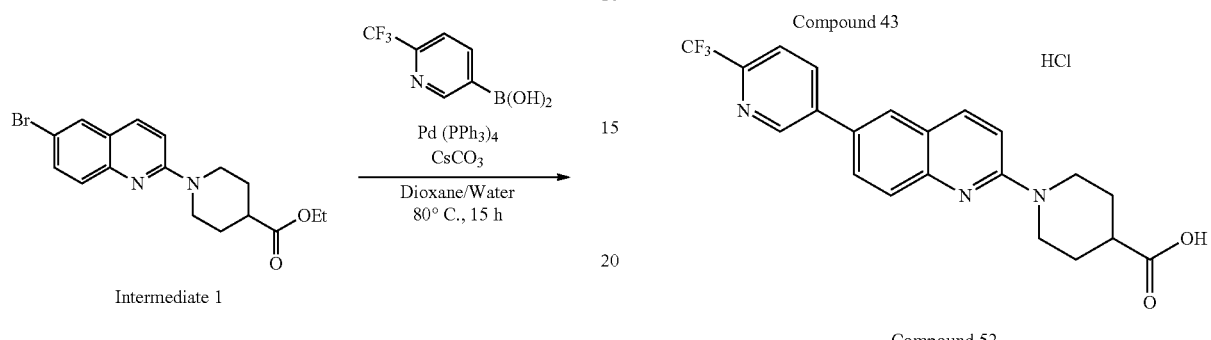

Compound 43

Tetrakis(triphenylphosphine)palladium(0) (100 mg, 0.09 mmol) was added to a stirring suspension of intermediate 1 (ethyl 1-(6-bromoquinolin-2-yl)piperidine-4-carboxylate) (700 mg, 1.9 mmol), (6-(trifluoromethyl)pyridin-3-yl)boronic acid (400 mg, 2.1 mmol) and caesium carbonate (3.5 ml, 3M solution) in a mixture of dioxane (18 ml) and water (3 ml). The suspension was allowed to stir at 80° C. for a duration of 15 hours. The solvent was evaporated in high vacuum and the residue was purified by column chromatography (silica gel, Petrol ether/EtOAc 4:1) to obtain Compound 43 as a colourless solid (230 mg, 26%).

HPLC-MS [M+H]⁺ 430.21; MP: 183-184° C.; ¹H NMR (400 MHz, CDCl₃) δ 9.02 (d, J=2.2 Hz, 1H), 8.14-8.07 (m, 1H), 7.94 (d, J=9.2 Hz, 1H), 7.85-7.72 (m, 4H), 7.06 (d, J=9.2 Hz, 1H), 4.51 (dt, J=13.5, 3.9 Hz, 2H), 4.17 (a, J=7.1 Hz, 2H), 3.16 (ddd, J=13.8, 11.4, 2.9 Hz, 2H), 2.62 (tt, J=11.0, 4.0 Hz, 1H), 2.11-2.00 (m, 2H), 1.92-1.74 (m, 21H), 1.27 (t, J=7.1 Hz, 3H); ¹³C NMR (101 MHz, CDCl₃) δ 174.62, 157.61, 148.29, 146.41, 146.06, 139.29, 137.64, 135.09, 129.72, 128.22, 127.69, 125.93, 123.13, 122.99, 120.43, 110.52, 60.55, 44.67, 41.43, 27.93, 14.23.

In an embodiment, the method of synthesizing Compound 52 (1-(6-(6-(trifluoromethyl)pyridin-3-yl)quinolin-2-yl)piperidine-4-carboxylic acid hydrochloride) is as follows:

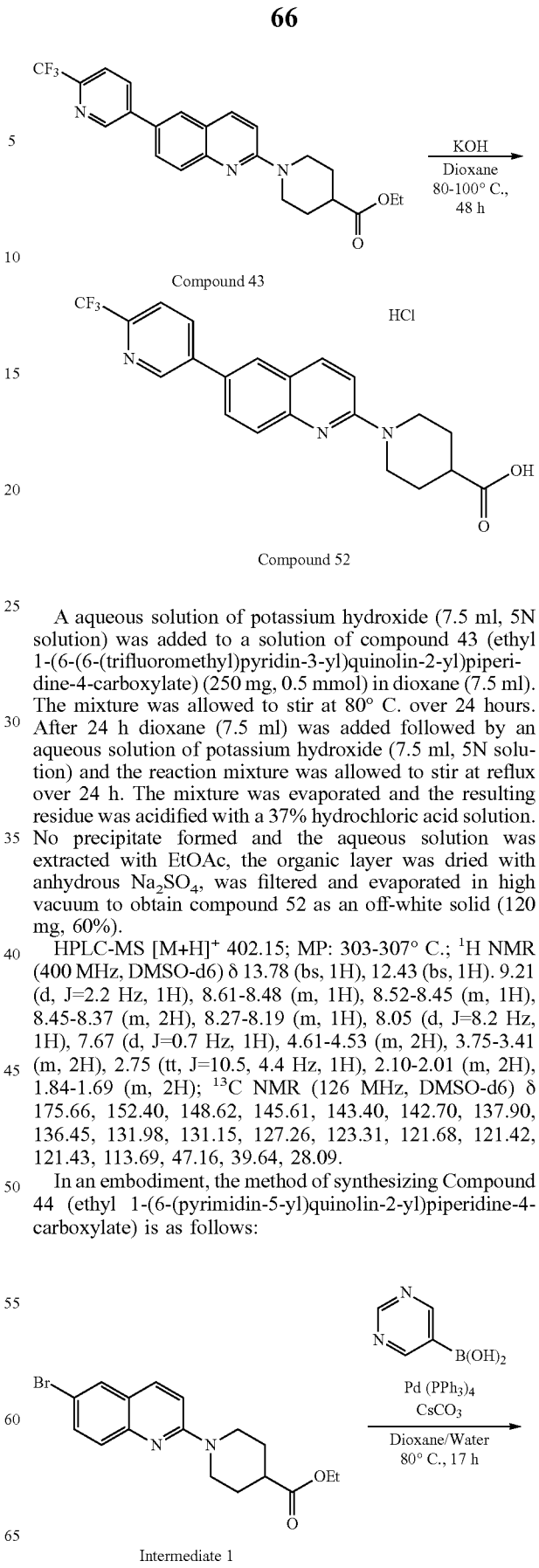

A aqueous solution of potassium hydroxide (7.5 ml, 5N solution) was added to a solution of compound 43 (ethyl 1-(6-(6-(trifluoromethyl)pyridin-3-yl)quinolin-2-yl)piperidine-4-carboxylate) (250 mg, 0.5 mmol) in dioxane (7.5 ml). The mixture was allowed to stir at 80° C. over 24 hours. After 24 h dioxane (7.5 ml) was added followed by an aqueous solution of potassium hydroxide (7.5 ml, 5N solution) and the reaction mixture was allowed to stir at reflux over 24 h. The mixture was evaporated and the resulting residue was acidified with a 37% hydrochloric acid solution. No precipitate formed and the aqueous solution was extracted with EtOAc, the organic layer was dried with anhydrous Na₂SO₄, was filtered and evaporated in high vacuum to obtain compound 52 as an off-white solid (120 mg, 60%).

HPLC-MS [M+H]⁺ 402.15; MP: 303-307° C.; ¹H NMR (400 MHz, DMSO-d6) δ 13.78 (bs, 1H), 12.43 (bs, 1H). 9.21 (d, J=2.2 Hz, 1H), 8.61-8.48 (m, 1H), 8.52-8.45 (m, 1H), 8.45-8.37 (m, 2H), 8.27-8.19 (m, 1H), 8.05 (d, J=8.2 Hz, 1H), 7.67 (d, J=0.7 Hz, 1H), 4.61-4.53 (m, 2H), 3.75-3.41 (m, 2H), 2.75 (tt, J=10.5, 4.4 Hz, 1H), 2.10-2.01 (m, 2H), 1.84-1.69 (m, 2H); ¹³C NMR (126 MHz, DMSO-d6) δ 175.66, 152.40, 148.62, 145.61, 143.40, 142.70, 137.90, 136.45, 131.98, 131.15, 127.26, 123.31, 121.68, 121.42, 121.43, 113.69, 47.16, 39.64, 28.09.

In an embodiment, the method of synthesizing Compound 44 (ethyl 1-(6-(pyrimidin-5-yl)quinolin-2-yl)piperidine-4-carboxylate) is as follows:

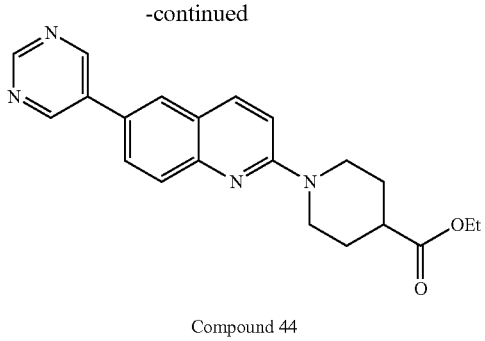

Compound 44

Tetrakis(triphenylphosphine)palladium(0) (92.4 mg, 0.08 mmol) was added to a stirring suspension of intermediate 1 (ethyl 1-(6-bromoquinolin-2-yl)piperidine-4-carboxylate) (600 mg, 1.6 mmol), pyrimidin-5-ylboronic acid (223 mg, 1.8 mmol) and caesium carbonate (3 ml, 3M solution) in a mixture of dioxane (15 ml) and water (2.5 ml). The suspension was allowed to stir at 80° C. for a duration of 17 hours. The solvent was evaporated in high vacuum and the residue was purified by column chromatography (silica gel, Petrol ether/EtOAc 1:2; to obtain Compound 44 as a colourless solid (360 mg, 60%).

HPLC-MS [M+H]$^+$ 363.22; MP: 128-130° C.; $^1$H NMR (400 MHz, CDCl$_3$) δ 9.18 (s, 1H), 9.03 (s, 2H), 7.94 (d, J=9.1 Hz, 1H), 7.83-7.77 (m, 2H), 7.77-7.70 (m, 1H), 7.05 (d, J=9.2 Hz, 1H), 4.50 (dt, J=13.8, 3.9 Hz, 2H), 4.16 (q, J=7.1 Hz, 2H), 3.21-3.09 (m, 2H), 2.61 (tt, J=11.0, 4.0 Hz, 1H), 2.11-2.00 (m, 2H), 1.89-1.74 (m, 2H), 1.27 (t, J=7.1 Hz, 3H); $^{13}$C NMR (101 MHz, CDCl$_3$) δ 174.62, 157.60, 157.00, 154.69, 148.24, 137.55, 134.18, 127.82, 127.61, 125.52, 123.06, 110.55, 60.54, 44.66, 41.42, 27.93, 14.23.

In an embodiment, the method of synthesizing Compound 48 (1-(6-(pyrimidin-5-yl)quinolin-2-yl)piperidine-4-carboxylic acid hydrochloride) is as follows:

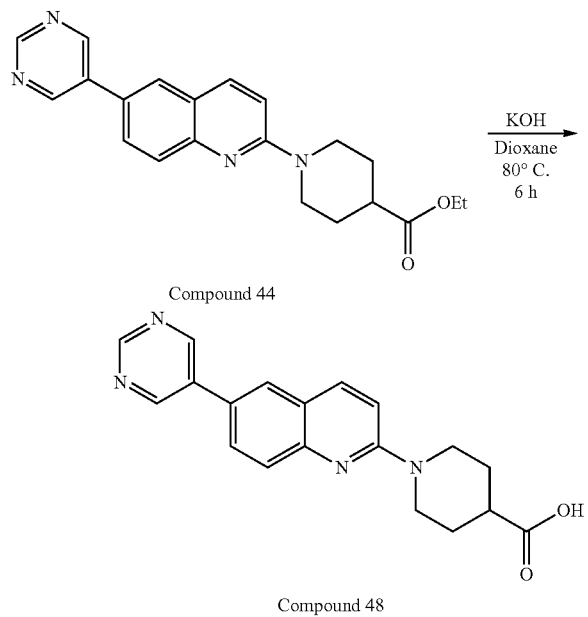

A aqueous solution of potassium hydroxide (6.3 ml, 5N solution) was added to a solution of compound 44 (ethyl 1 (6 (pyrimidin 5 yl)quinolin 2 yl)piperidine 4 carboxylate) (200 mg, 0.5 mmol) in dioxane (6.3 ml). The mixture was allowed to stir at 80° C. for a duration of 6 hours. The dioxane was evaporated and the resulting aqueous mixture was acidified a 37% Hydrochloric acid solution to give a suspension at 0° C. The product was isolated by filtration, was washed with water and was dried in high vacuum at 40° C. Compound 48 was Isolated as a colourless solid (200 mg, 100%).

HPLC-MS [M+H]$^+$ 335.20; MP: 306-310° C.; $^1$H NMR (400 MHz, DMSO-d6) δ 13.94 (bs, 1H), 9.35-9.14 (m, 3H), 8.70 (d, J=8.8 Hz, 1H), 8.51-8.39 (m, 2H), 8.29-8.21 (m, 1H), 7.70 (d, J=9.8 Hz, 1H), 4.61 (bs, 2H), 3.65-3.53 (m, 2H), 2.76 (tt, J=10.6, 4.3 Hz, 1H), 2.05 (dd, J=14.0, 3.9 Hz, 2H), 1.85-1.70 (m, 2H); $^{13}$C NMR (101 MHz, DMSO-d6) δ 175.56, 157.86, 155.21, 151.71, 142.78, 137.81, 132.35, 131.02, 130.60, 126.84, 121.57, 119.59, 113.99, 47.52, 39.54, 28.11.

In an embodiment, the method of synthesizing Compound 50 (ethyl 1-(6-(6-methylpyridin-3-yl)quinolin-2-yl)piperidine-4-carboxylate) is as follows:

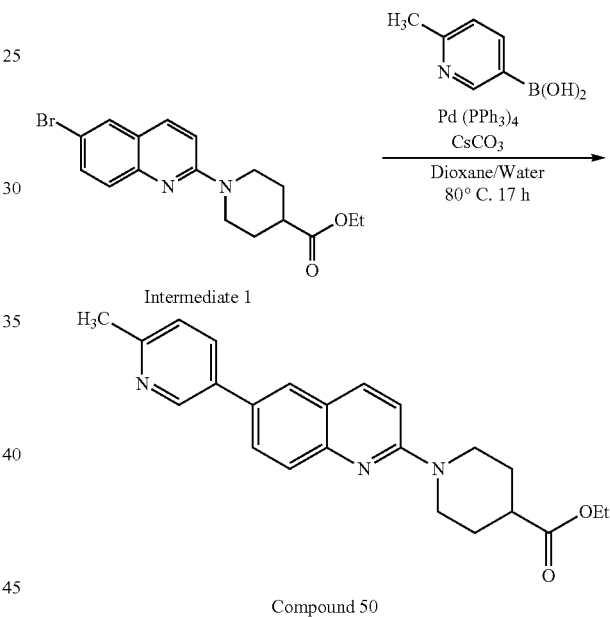

Compound 50

Tetrakis(triphenylphosphine)palladium(0) (150 mg, 0.13 mmol) was added to a stirring suspension of intermediate 1 (ethyl 1-(6-bromoquinolin-2-yl)piperidine-4-carboxylate) (1 g, 2.7 mmol), (6-methylpyridin-3-yl)boronic acid (410 mg, 3.0 mmol) and caesium carbonate (5 ml, 3M solution) in a mixture of dioxane (26 ml) and water (4.2 ml). The suspension was allowed to stir at 80° C. for a duration of 24 hours. The solvent was evaporated in high vacuum and the residue was purified by column chromatography (silica gel, Petrol ether/EtOAc 2:1-1:1) to obtain Compound 50 as an orange solid (160 mg, 14%).

HPLC-MS [M+H]$^+$ 376.24; MP: 214-218° C.; $^1$H NMR (400 MHz, CDCl$_3$) δ 8.86-8.78 (m, 1H), 7.93 (d, J=9.2 Hz, 1H), 7.91-7.81 (m, 1H), 7.83-7.68 (m, 3H), 7.23 (d, J=8.0 Hz, 1H), 7.03 (d, J=9.2 Hz, 1H), 4.48 (dt, J=13.5, 3.9 Hz, 2H), 4.16 (q, J=7.1 Hz, 2H), 3.14 (ddd, J=13.9, 11.5, 2.9 Hz, 2H), 2.70-2.48 (m, 4H), 2.05 (dd, J=13.4, 3.9 Hz, 2H), 1.89-1.74 (m, 2H), 1.27 (t, J=7.1 Hz, 3H); $^{13}$C NMR (126 MHz, CDCl$_3$) δ 174.70, 157.40, 156.73, 147.60, 147.40, 137.57, 134.56, 133.51, 131.56, 128.45, 127.31, 125.01, 123.17, 123.06, 110.31, 60.52, 44.79, 41.48, 27.95, 24.10, 14.25.

In an embodiment, the method of synthesizing Compound 80 (1-(6-(6-methylpyridin-3-yl)quinolin-2-yl)piperidine-4-carboxylic acid hydrochloride) is as follows:

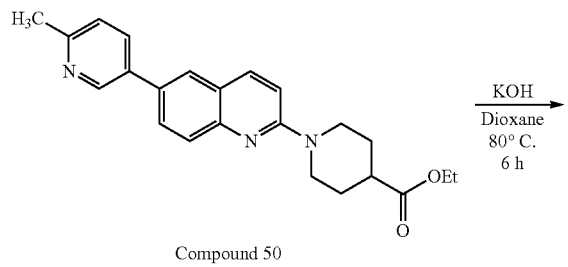

Compound 50

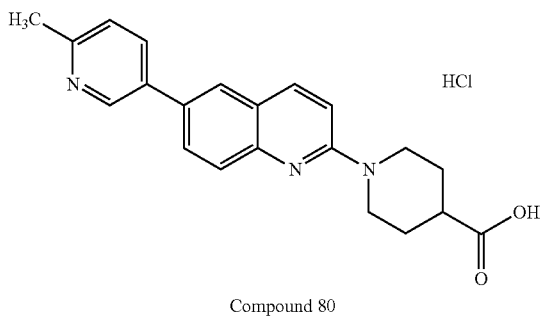

Compound 80

A aqueous solution of potassium hydroxide (4 ml, 5N solution) was added to a solution of compound 50 (ethyl 1-(6-(6-methylpyridin-3-yl)quinolin-2-yl)piperidine-4-carboxylate) (130 mg, 0.3 mmol) in dioxane (4 ml). The mixture was allowed to stir at 80° C. for a duration of 2 hours. The dioxane was evaporated and the resulting aqueous mixture was acidified a 37% Hydrochloric acid solution. No precipitate formed and the aqueous solution was extracted with a mixture of DCM/isop (7:3), the organic layer was dried with anhydrous $Na_2SO_4$, was filtered and evaporated in high vacuum to obtain Compound 80 as a yellow solid (112 mg, 100%). HPLC-MS [M+H]$^+$ 348.15; MP: 281-284° C.; $^1$H NMR (400 MHz, $D_2O$) δ 9.15 (d, J=2.2 Hz, 1H), 8.94 (dd, J=8.5, 2.1 Hz, 1H), 8.57 (d, J=9.8 Hz, 1H), 8.38 (d, J=2.0 Hz, 1H), 8.27 (dd, J=8.8, 2.0 Hz, 1H), 8.17 (t, J=8.5 Hz, 2H), 7.64 (d, J=9.8 Hz, 1H), 4.52 (dt, J=14.1, 4.2 Hz, 2H), 3.78 (ddd, J=14.0, 11.0, 3.0 Hz, 2H), 3.11 (tt, J=10.3, 4.5 Hz, 1H), 3.03 (s, 3H), 2.41 (dt, J=12.5, 4.0 Hz, 2H), 2.08 (qd, J=10.8, 5.5 Hz, 2H); $^{13}$C NMR (126 MHz, $D_2O$) δ 152.08, 150.13, 145.41, 144.40, 143.31, 138.41, 137.08, 135.99, 131.30, 128.44, 127.30, 121.49, 118.76, 118.09, 113.16, 46.62, 39.45, 27.24, 18.88.

In an embodiment, the method of synthesizing Compound 54 (ethyl 1-(6-(pyridin-4-yl)quinolin-2-yl)piperidine-3-carboxylate) is as follows:

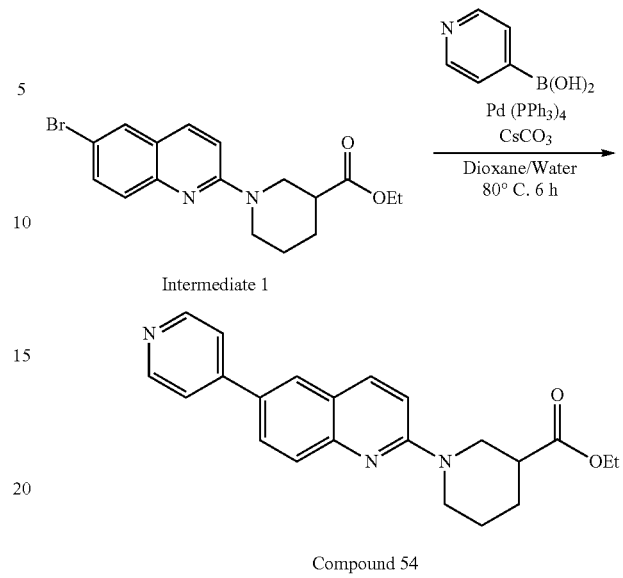

Intermediate 1

Compound 54

Tetrakis(triphenylphosphine)palladium(0) (207 mg, 0.18 mmol) was added to a stirring suspension of intermediate 1 (ethyl 1-(6-bromoquinolin-2-yl)piperidine-4-carboxylate) (1.3 g, 3.5 mmol), pyridine-4-ylboronic acid (480 mg, 3.9 mmol) and caesium carbonate (6.5 ml, 3M solution) in a mixture of dioxane (33 ml) and water (5.5 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 54 as a colourless solid (750 mg, 57%).

HPLC-MS [M+H]$^+$ 362.22; MP: 84-87° C.; $^1$H NMR (400 MHz, $CDCl_3$) δ 8.72-8.64 (m, 2H), 7.95 (d, J=9.2 Hz, 1H), 7.89 (d, J=2.1 Hz, 1H), 7.84 (dd, J=8.8, 2.1 Hz, 1H), 7.80 (d, J=8.7 Hz, 1H), 7.64-7.59 (m, 2H), 7.10 (d, J=9.2 Hz, 1H), 4.60 (ddd, J=13.3, 3.6, 1.8 Hz, 1H), 4.32 (ddd, J=13.2, 4.8, 3.2 Hz, 1H), 4.20 (q, J=7.1 Hz, 2H), 3.40 (m, 1H), 3.28 (ddd, J=13.5, 10.8, 3.0 Hz, 1H), 2.65 (tt, J=9.9, 4.0 Hz, 1H), 2.21-2.09 (m, 1H), 1.94-1.78 (m, 2H), 1.75-1.59 (m, 1H), 1.30 (t, J=7.1 Hz, 3H); $^{13}$C NMR (101 MHz, $CDCl_3$) δ 173.67, 157.46, 150.21, 148.42, 148.03, 137.73, 131.44, 127.98, 127.40, 125.60, 122.8B, 121.32, 110.46, 60.61, 47.36, 45.56, 41.30, 27.58, 24.20, 14.25.

In an embodiment, the method of synthesizing Compound 62 (1-(6-(pyridin-4-yl)quinolin-2-yl)piperidine-3-carboxylic acid hydrochloride) is as follows:

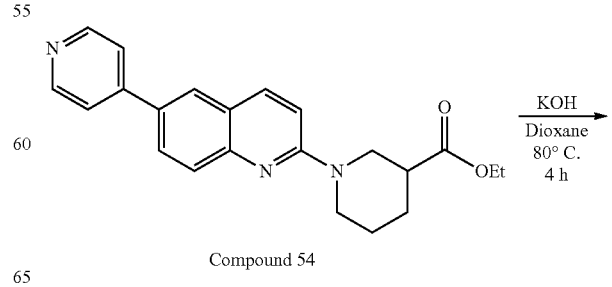

Compound 54

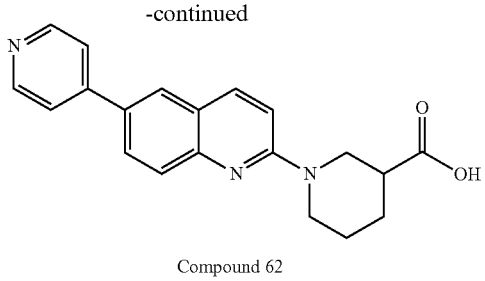

Compound 62

A aqueous solution of potassium hydroxide (14 ml, 5N solution) was added to a solution of compound 54 (ethyl 1 (6 (pyridin 4 yl)quinolin 2 yl)piperidine 3 carboxylate) (450 mg, 1.2 mmol) in dioxane (14 ml). The mixture was allowed to stir at 80° C. for a duration of 4 hours. The mixture was evaporated and the resulting residue was acidified with a 37% hydrochloric acid solution. The aqueous solution was extracted with a mixture of DCM/Isop (7:3), the organic layer was dried with anhydrous $Na_2SO_4$, was filtered and evaporated in high vacuum to give a yellow residue. The residue was suspended in EtOAc and a solution of hydrochloric acid in diethyl ether (1.5 mL, 2N) was added dropwise at 0° C. to afford a suspension. The solid was separated by filtration and Compound 62 was isolated as an orange solid (74 mg, 51%).

HPLC-MS [M+H]$^+$ 334.19; MP; 245-250° C.; $^1$H NMR (500 MHz, DMSO-d6) δ 8.98 (d, J=5.9 Hz, 2H), 8.69-8.66 (m, 1H), 8.48-8.33 (m, 5H), 7.72-7.62 (m, 1H), 4.51-4.37 (m, 1H), 4.37-4.38 (m, 1H), 3.43-3.45 (m, 1H), 2.90-2.81 (m, 1H), 2.79-2.71 (m, 1H), 2.09-2.00 (m, 1H), 1.89-1.77 (m, 2H), 1.76-1.62 (m, 1H); $^{13}$C NMR (126 MHz, DMSO-d6) δ 174.53, 173.46, 153.82, 148.22, 143.30, 141.81, 130.76, 128.76, 123.72, 121.86, 114.61, 113.92, 65.37, 52.17, 48.94, 26.96, 24.28, 15.63.

In an embodiment, the method of synthesizing Compound 55 (ethyl 1-(6-(pyridin-2-yl)quinolin-2-yl)piperidine-4-carboxylate) is as follows:

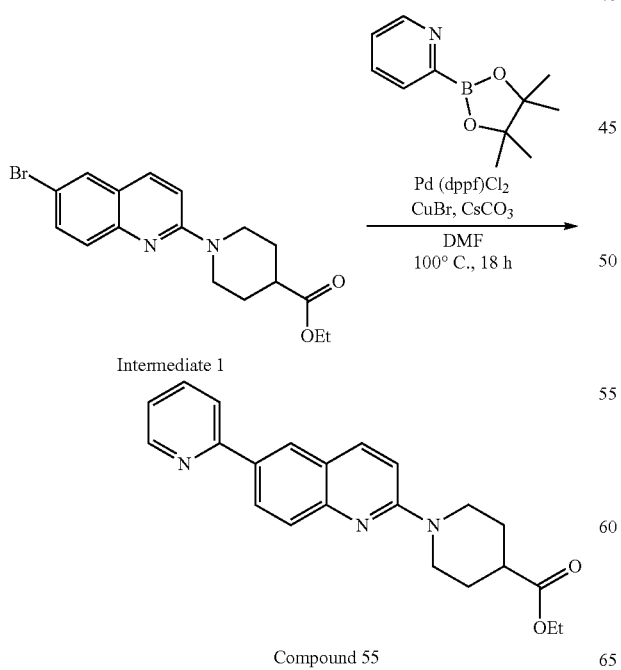

Intermediate 1 (ethyl 1-(6-bromoquinolin-2-yl)piperidine-4-carboxylate) (250 mg, 0.69 mmol), pyridine-2-boronic acid, pinacol ester (290 mg, 1.39 mmol), Copper bromide (100 mg, 0.69 mmol), caesium carbonate (950 mg, 2.9 mmol) and [1,1'-Bis(diphenylphosphino)ferrocene]dichloropalladium(II) (51 mg, 0.069 mmol) were placed in a flask. The flask was degassed with $N_2$ for 10 minutes. Dry DMF (25 ml) was added and the resulting mixture was degassed for another 10 minutes before the reaction mixture was heated at 100° C. for a duration of 18 hours. Water was added and the aqueous solution was extracted with EtOAc, the organic layer was dried with anhydrous $Na_2SO_4$, was filtered and evaporated in high vacuum. The resulting residue was purified by column chromatography (silica gel, Petrol ether/EtOAc 2:1) to obtain Compound 55 as a colourless solid (167 mg, 46%).

HPLC-MS [M+H]$^+$ 362.24; MP: 134-137° C.; $^1$H NMR (500 MHz, CDCl$_3$) δ 8.73-8.68 (m, 1H), 8.30 (d, J=2.0 Hz, 1H), 8.22-8.16 (m, 1H), 8.07-7.90 (m, 2H), 7.84-7.74 (m, 2H), 7.26-7.19 (m, 1H), 7.02 (d, J=9.2 Hz, 1H), 4.54-4.48 (m, 2H), 4.16 (q, J=7.1 Hz, 2H), 3.33-3.10 (m, 2H), 2.62 (tt, J=10.8, 4.0 Hz, 1H), 2.11-2.02 (m, 2H), 1.91-1.80 (m, 2H), 1.27 (t, J=7.1 Hz, 3H); $^{13}$C NMR (126 MHz, DMSO-d6) δ 174.58, 157.60, 156.27, 149.94, 148.36, 138.56, 137.64, 132.51, 128.12, 126.62, 125.93, 122.90, 122.53, 120.25, 111.06, 60.41, 44.42, 40.94, 28.02, 14.57.

In an embodiment, the method of synthesizing Compound 61 (1-(6-(pyridin-2-yl)quinolin-2-yl)piperidine-4-carboxylic acid) is as follows:

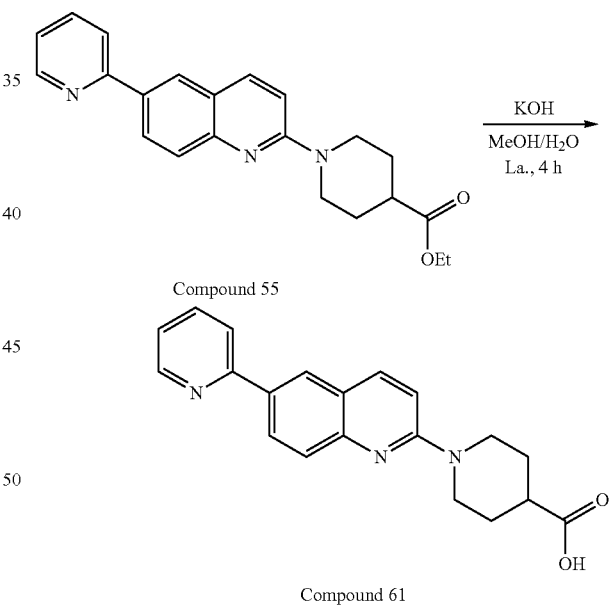

Potassium hydroxide (85 mg, 1.5 mmol) was added to a solution of compound 55 (ethyl 1-(6-(pyridin-2-yl)quinolin-2-yl)piperidine-4-carboxylate) (100 mg, 0.3 mmol) in a mixture of MeOH and water (2.2 ml). The mixture was allowed to stir at room temperature over 4 hours. The MeOH was evaporated and the resulting aqueous mixture was acidified with acetic acid. The aqueous solution was extracted with EtOAc, the organic layer was dried with anhydrous $Na_2SO_4$, was filtered and evaporated in high vacuum. Compound 61 was isolated as a yellow solid (53 mg, 48%).

HPLC-MS [M+H]+ 334.19; MP: 280-283° C.; ¹H NMR (400 MHz, DMSO-d6) δ 8.70-8.63 (m, 1H), 8.44 (d, J=2.1 Hz, 1H), 8.31-8.22 (m, 1H), 8.12 (d, J=9.2 Hz, 1H), 8.07-7.99 (m, 1H), 7.93-7.84 (m, 1H), 7.62 (d, J=8.8 Hz, 1H), 7.37-7.25 (m, 2H), 4.49-4.41 (m, 2H), 3.12-3.05 (m, 2H), 2.48-2.42 (m, 1H), 1.95-1.88 (m, 2H), 1.60-1.50 (m, 2H); ¹³C NMR (101 MHz, DMSO-d6) δ 176.84, 157.68, 156.31, 149.91, 148.49, 138.42, 137.61, 132.31, 128.03, 126.61, 125.90, 122.82, 122.47, 120.21, 111.02, 44.71, 41.90, 28.54.

In an embodiment, the method of synthesizing Compound 57 (1-(ethyl 1-(4-methyl-6-(pyridin-4-yl)quinolin-2-yl)piperidine-4-carboxylate) is as follows:

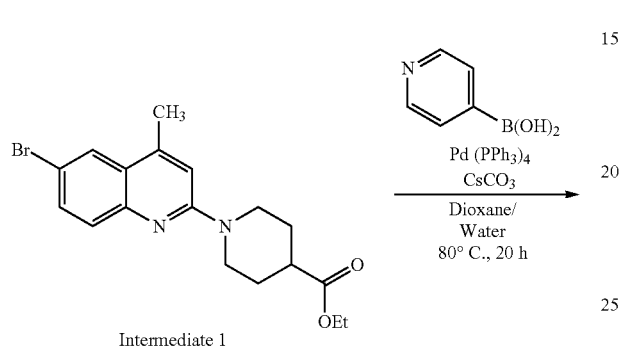

Intermediate 1

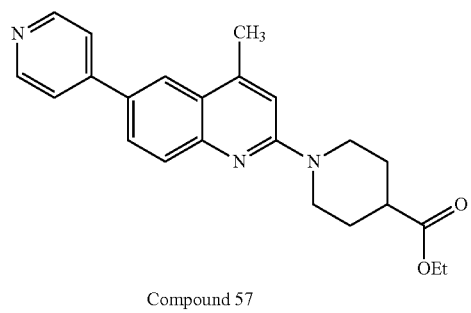

Compound 57

Tetrakis(triphenylphosphine)palladium(0) (175 mg, 0.15 mmol) was added to a stirring suspension of intermediate 1 (ethyl 1-(6-bromoquinolin-2-yl)piperidine-4-carboxylate) (1.1 g, 3.03 mmol), pyridine-4-ylboronic acid (410 mg, 3.33 mmol) and caesium carbonate (6 ml, 3M solution) in a mixture of dioxane (20 ml) and water (4 ml). The suspension was allowed to stir at 80° C. for a duration of 20 hours. The solvent was evaporated in high vacuum and the residue was purified by column chromatography (silica gel, Petrol ether/EtOAc 2:1-2:1) to obtain Compound 57 as a colourless solid (600 mg, 53%).

HPLC-MS [M+H]+ 376.29; MP: 287-289° C.; ¹H NMR (400 MHz, DMSO-d6) δ 9.01-8.90 (m, 2H), 8.54-8.41 (m, 3H), 8.35 (dd, J=8.8, 2.1 Hz, 1H), 7.65-7.52 (m, 2H), 4.63-4.47 (m, 2H), 4.10 (q, J=7.1 Hz, 2H), 2.88-2.72 (m, 5H), 2.55-2.49 (m, 1H), 2.05 (dd, J=14.0, 4.1 Hz, 2H), 1.81-1.69 (m, 2H), 1.21 (t, J=7.1, 3H); ¹³C NMR (101 MHz, DMSO-d6) δ 174.00, 167.86, 148.76, 131.98, 131.88, 129.28, 129.16, 125.46, 123.87, 122.09, 114.11, 112.91, 73.90, 60.63, 46.74, 34.61, 28.03, 19.61, 14.55.

In an embodiment, the method of synthesizing Compound 56 (1-(4-methyl-6-(pyridin-4-yl)quinolin-2-yl)piperidine-4-carboxylic acid) is as follows:

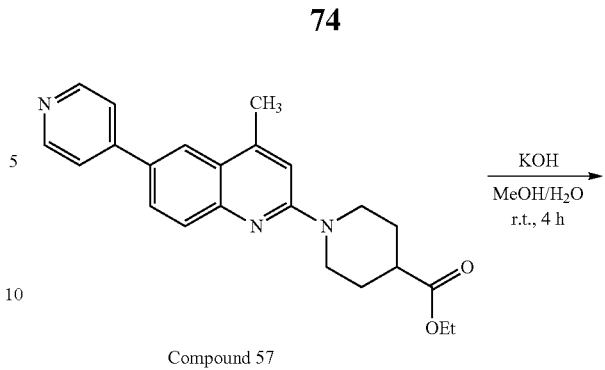

Compound 57

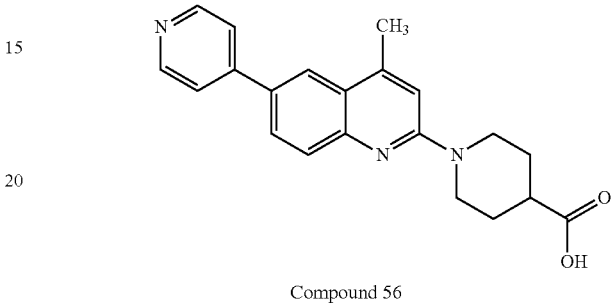

Compound 56

Potassium hydroxide (300 mg, 5.33 mmol) was added to a solution of compound 57 (1-(ethyl 1-(4-methyl-6-(pyridin-4-yl)quinolin-2-yl)piperidine-4-carboxylate) (400 mg, 1.07 mmol) in a mixture of MeOH and water (11 ml). The mixture was allowed to stir at room temperature over 4 hours. The MeOH was evaporated and the resulting aqueous mixture was acidified with acetic acid. The aqueous solution was extracted with EtOAc, the organic layer was dried with anhydrous Na₂SO₄, was filtered and evaporated in high vacuum. Compound 56 was isolated as a colourless solid (300 mg, 85%).

HPLC-MS [M+H]+ 348.23; MP: 340-342° C.; 1H NMR (500 MHz, DMSO-d6) δ 8.66-8.61 (m, 2H), 8.23-8.18 (m, 1H), 7.99-7.93 (m, 1H), 7.87-7.82 (m, 2H), 7.65 (d, J=8.7 Hz, 1H), 7.21 (bs, 1H), 4.52-4.43 (m, 2H), 3.15-3.07 (m, 2H), 2.66 (s, 3H), 2.62-2.55 (m, 1H), 1.96-1.89 (m, 2H), 1.59-1.51 (m, 2H); ¹³C NMR (126 MHz, DMSO-d6) δ 176.65, 157.53, 150.36, 148.50, 147.39, 146.09, 130.13, 127.95, 127.64, 123.37, 122.73, 121.32, 111.13, 44.09, 40.26, 27.83, 19.29.

In an embodiment, the method of synthesizing Compound 58 (ethyl 1-(6-(3-fluoro-4-methoxyphenyl)quinolin-2-yl)piperidine-4-carboxylate) is as follows:

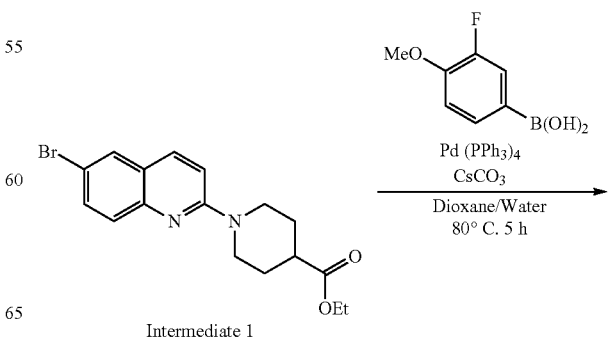

Intermediate 1

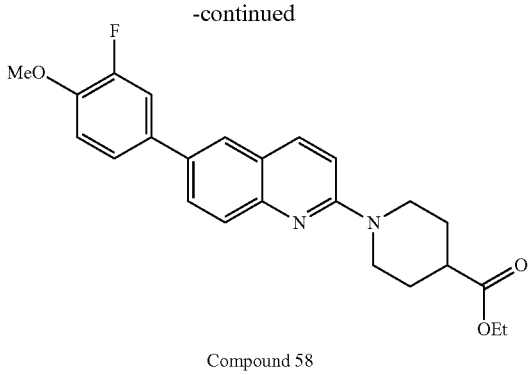

Compound 58

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (3-fluoro-4-methoxyphenyl)boronic acid (310 mg, 1.83 mmol) and caesium carbonate (3 ml, 3M solution) in a mixture of dioxane (16 ml) and water (2.6 ml). The suspension was allowed to stir at 80° C. for a duration of 5 hours. The solvent was evaporated in high vacuum and the residue was purified by column chromatography (silica gel, Petrol ether/EtOAc 3:1) to obtain Compound 58 as a colourless solid (417.3 mg, 52%).

HPLC-MS [M+H]$^+$ 409.27; MP: 150-152° C.; $^1$H NMR (400 MHz, CDCl$_3$) δ 7.91 (d, J=9.1 Hz, 1H), 7.79-7.69 (m, 3H), 7.44-7.34 (m, 2H), 7.08-6.97 (m, 2H), 4.47 (dt, J=13.5, 3.9 Hz, 2H), 4.16 (q, J=7.2 Hz, 2H), 3.94 (s, 3H), 3.13 (ddd, J=13.8, 11.5, 2.9 Hz, 2H), 2.59 (tt, J=11.0, 4.0 Hz, 1H), 2.11-1.99 (m, 2H), 1.89-1.74 (m, 2H), 1.27 (t, J=7.1 Hz, 3H); $^{13}$C NMR (101 MHz, CDCl$_3$) δ 174.73, 157.28, 153.86, 151.43, 146.71, 137.59, 134.29, 133.52, 126.98, 124.55, 123.01, 122.48, 114.64, 113.72, 110.26, 60.52, 56.40, 44.87, 41.48, 27.94, 14.23.

In an embodiment, the method of synthesizing Compound 59 (ethyl 1-(6-(3-chloro-4-methoxyphenyl)quinolin-2-yl)piperidine-4-carboxylate) is as follows:

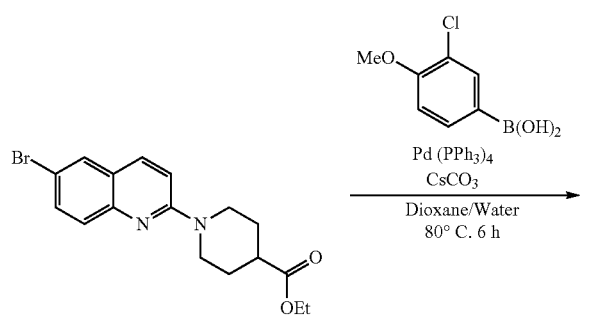

Tetrakis(triphenylphosphine)palladium(0) (96 mg, 0.083 mmol) was added to a stirring suspension of intermediate 1 (ethyl 1-(6-bromoquinolin-2-yl)piperidine-4-carboxylate) (600 mg, 1.66 mmol), (3-chloro-4-methoxyphenyl)boronic acid (341 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 3:1) to obtain Compound 59 as a colourless solid (400 mg, S7% A).

HPLC-MS [M+H]$^+$ 425.24; MP: 145-147° C.; 1H NMR (400 MHz, CDCl$_3$) δ 7.91 (d, J=9.1 Hz, 1H), 7.79-7.65 (m, 4H), 7.58-7.49 (m, 1H), 7.06-6.97 (m, 2H), 4.47 (dt, J=13.5, 3.9 Hz, 2H), 4.16 (q, 1=7.1 Hz, 2H), 3.95 (s, 3H), 3.13 (ddd, J=13.8, 11.5, 2.9 Hz, 2H), 2.59 (tt, J=11.0, 4.0 Hz, 1H), 2.11-1.99 (m, 2H), 1.89-1.74 (m, 2H), 1.27 (t, J=7.1 Hz, 3H); $^{13}$C NMR (101 MHz, CDCl$_3$) δ 174.73, 157.29, 154.14, 137.59, 137.12, 134.48, 133.35, 132.04, 128.70, 127.00, 126.09, 124.56, 123.02, 122.81, 112.34, 110.27, 60.52, 56.28, 44.87, 41.48, 27.94, 14.23.

In an embodiment, the method of synthesizing Compound 60 (ethyl 1-(6-(3,4-dimethoxyphenyl)quinolin-2-yl)piperidine-4-carboxylate) is as follows:

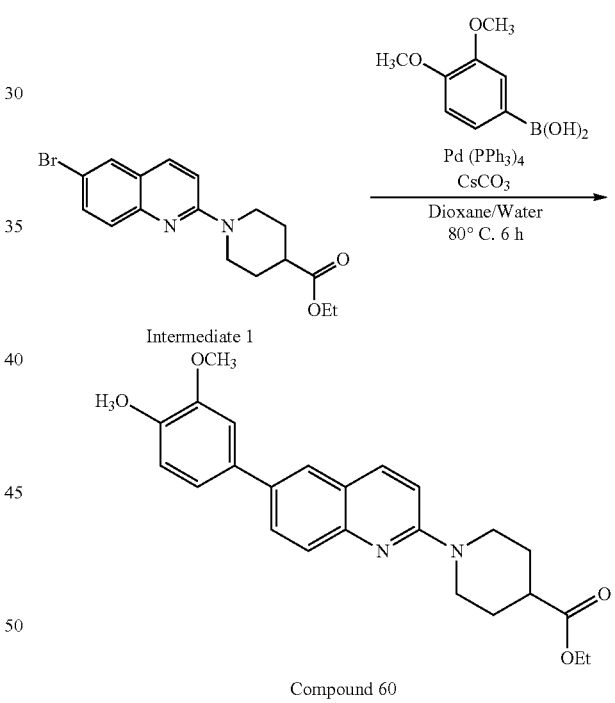

Compound 60

Tetrakis(triphenylphosphine)palladium(0) (135 mg, 0.12 mmol) was added to a stirring suspension of intermediate 1 (ethyl 1-(6-bromoquinolin-2-yl)piperidine-4-carboxylate) (840 mg, 2.33 mmol), (3,4-dimethoxyphenyl)boronic acid (470 mg, 2.56 mmol) and caesium carbonate (4.2 ml, 3M solution) in a mixture of dioxane (22 ml) and water (3.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 60 as a colourless solid (500 mg, 51%).

HPLC-MS [M+H]$^+$ 421.29; MP: 151-153° C.; $^1$H NMR (400 MHz, CDCl$_3$) δ 7.92 (d, J=9.2 Hz, 1H), 7.81-7.67 (m,

3H), 7.24-7.15 (m, 2H), 7.02 (d, J=9.2 Hz, 1H), 6.96 (m, 1H), 4.47 (dt, J=13.4, 3.9 Hz, 2H), 4.16 (q, J=7.1 Hz, 2H), 3.98 (s, 3H), 3.93 (s, 3H), 3.12 (ddd, J=13.8, 11.4, 2.8 Hz, 2H), 2.59 (tt, J=11.1, 4.0 Hz, 1H), 2.11-1.99 (m, 2H), 1.90-1.75 (m, 2H), 1.27 (t, J=7.1 Hz, 3H); $^{13}$C NMR (101 MHz, CDCl$_3$) δ 174.76, 157.27, 149.20, 148.39, 137.53, 134.90, 134.01, 128.86, 126.90, 124.49, 123.06, 119.29, 111.55, 110.35, 110.20, 60.51, 55.99, 44.90, 41.50, 27.95, 14.24.

In an embodiment, the method of synthesizing Compound 63 (ethyl 1-(6-(4-chloro-3-fluorophenyl)quinolin-2-yl)piperidine-4-carboxylate) is as follows:

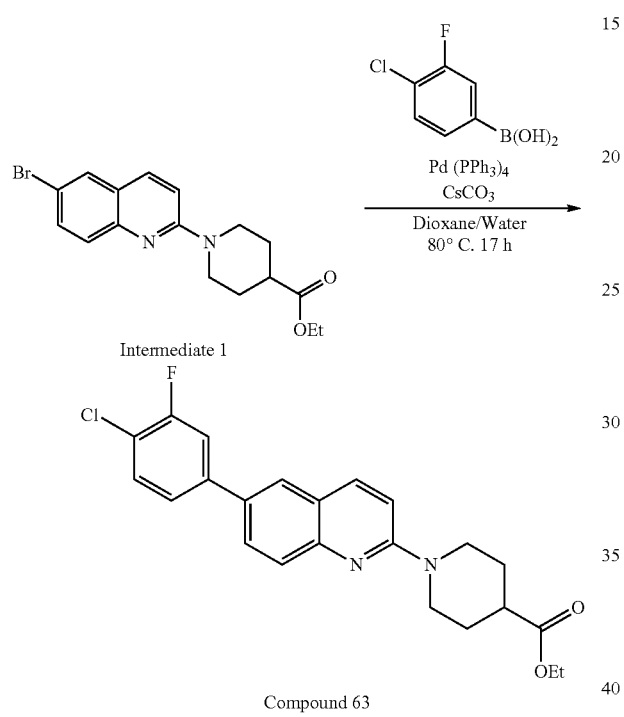

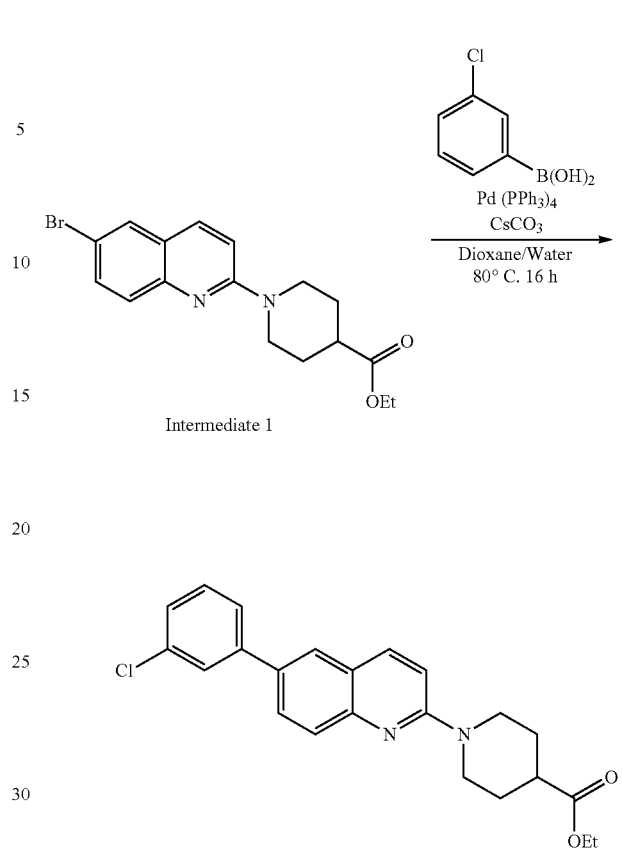

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (4-chloro-3-fluorophenyl)boronic acid (300 mg, 1.7 mmol) and caesium carbonate (3 ml, 3M solution) in a mixture of dioxane (15 ml) and water (2.6 ml). The suspension was allowed to stir at 80° C. for a duration of 17 hours. The solvent was evaporated in high vacuum and the residue was purified by column chromatography (silica gel, Petrol ether/EtOAc 6:1-4:1) to obtain Compound 63 as a colourless solid (510 mg, 75%).

HPLC-MS [M+H]$^+$ 413.19; MP: 115-116° C.; $^1$H NMR (500 MHz, CDCl$_3$) δ 7.90 (d, J=9.1 Hz, 1H), 7.84-7.63 (m, 3H), 7.55-7.40 (m, 2H), 7.41-7.33 (m, 1H), 7.02 (d, J=9.2 Hz, 1H), 4.49 (dt, J=13.7, 4.0 Hz, 2H), 4.16 (a, J=7.1 Hz, 2H), 3.24-3.10 (m, 2H), 2.60 (tt, J=11.0, 3.9 Hz, 1H), 2.05 (dd, J=13.5, 3.7 Hz, 2H), 1.88-1.76 (m, 2H), 1.27 (t, J=7.1 Hz, 3H); $^{13}$C NMR (126 MHz, CDCl$_3$) δ 174.66, 159.35, 157.38, 141.63, 137.68, 130.78, 128.36, 127.49, 125.16, 123.19, 122.89, 119.44, 119.30, 114.98, 114.81, 110.38, 60.54, 44.81, 41.44, 27.95, 14.25.

In an embodiment, the method of synthesizing Compound 64 (ethyl 1-(6-(3-chlorophenyl)quinolin-2-yl)piperidine-4-carboxylate) is as follows:

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (3-chlorophenyl)boronic acid (284 mg, 1.8 mmol) and caesium carbonate (3 ml, 3M solution) in a mixture of dioxane (15 mi) and water (3 ml). The suspension was allowed to stir at 80° C. for a duration of 16 hours. The solvent was evaporated in high vacuum and the residue was purified by column chromatography (silica gel, Petrol ether/EtOAc 6:1) to obtain Compound 64, as an off-white solid (510 mg, 80%).

HPLC-MS [M+H]$^+$ 395.21; MP: 117-120° C.; $^1$H NMR (500 MHz, CDCl$_3$) δ 7.92 (d, J=9.1 Hz, 1H), 7.80-7.73 (m, 3H), 7.66 (bs, 1H), 7.55 (d, J=7.7, 1H), 7.38 (m, 1H), 7.30 (d, J=7.9 Hz, 1H), 7.03 (d, J=9.2 Hz, 1H), 4.49 (dt, J=13.4, 4.0 Hz, 2H), 4.16 (q, J=7.1 Hz, 2H), 3.20-3.09 (m, 2H), 2.60 (tt, J=11.1, 4.0 Hz, 1H), 2.05 (dd, J=13.3, 3.8 Hz, 2H), 1.88-1.76 (m, 2H), 1.27 (t, J=7.1 Hz, 3H); $^{13}$C NMR (126 MHz, CDCl$_3$) δ 174.72, 157.46, 147.82, 142.82, 137.64, 134.69, 133.43, 130.01, 128.62, 127.16, 127.10, 126.86, 125.27, 125.13, 122.98, 110.29, 60.53, 44.80, 41.50, 27.96, 14.27.

In an embodiment, the method of synthesizing Compound 65 (ethyl 1-(6-(4-chlorophenyl)quinolin-2-yl)piperidine-4-carboxylate) is as follows:

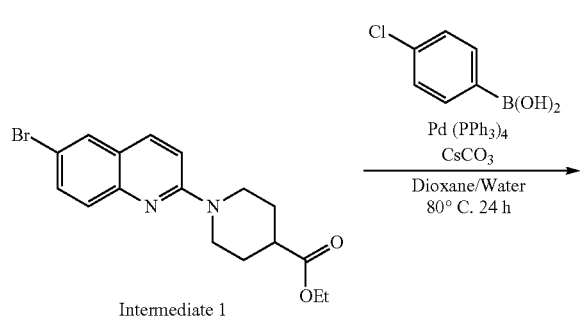

Intermediate 1

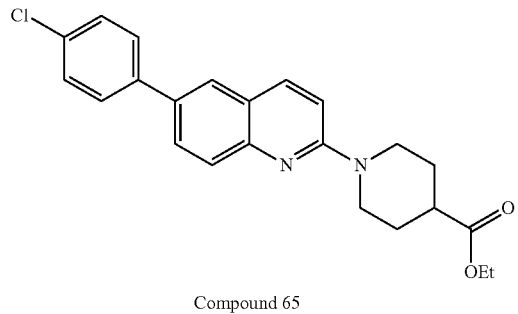

Compound 65

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (4-chlorophenyl)boronic acid (284 mg, 1.8 mmol) and caesium carbonate (3 ml, 3M solution) in a mixture of dioxane (15 ml) and water (2.6 ml). The suspension was allowed to stir at 80° C. for a duration of 24 hours. The solvent was evaporated in high vacuum and the residue was purified by column chromatography (silica gel, Petrol ether/EtOAc 4:1-2:1) to obtain Compound 65 as an off-white solid (390 mg, 60%).

HPLC-MS [M+H]$^+$ 395.21; MP: 160-164° C.; $^1$H NMR (500 MHz, CDCl$_3$) δ 7.91 (d, J=9.1 Hz, 1H), 7.81-7.69 (m, 3H), 7.59 (d, J=8.1 Hz, 2H), 7.41 (d, J=8.2 Hz, 2H), 7.02 (d, J=9.1 Hz, 1H), 4.53-4.44 (m, 2H), 4.16 (q, J=7.1 Hz, 2H), 3.22-3.04 (m, 2H), 2.60 (tt, J=11.1, 4.0 Hz, 1H), 2.05 (dd, J=13.5, 3.8 Hz, 2H), 1.88-1.76 (m, 2H), 1.27 (t, J=7.1 Hz, 3H); $^{13}$C NMR (126 MHz, CDCl$_3$) δ 174.63, 166.58, 154.29, 139.28, 137.63, 133.01, 128.94, 128.44, 128.24, 127.80, 126.46, 125.01, 122.88, 110.32, 60.56, 44.96, 41.38, 27.96, 14.25.

In an embodiment, the method of synthesizing Compound 66 (ethyl 1-(6-(3-(trifluoromethyl)phenyl)quinolin-2-yl)piperidine-4-carboxylate) is as follows:

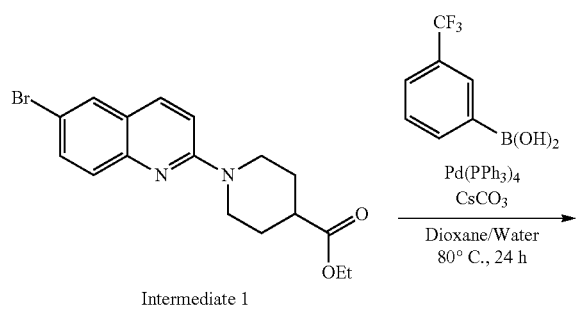

Intermediate 1

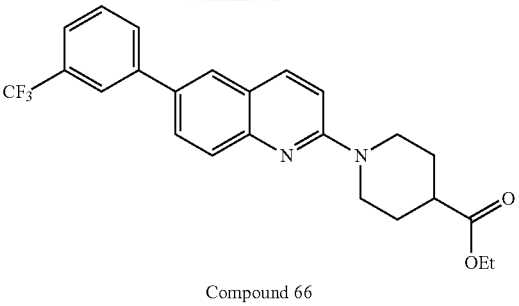

Compound 66

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (43-(trifluoromethyl)phenyl)boronic acid (345 mg, 1.7 mmol) and caesium carbonate (3 ml, 3M solution) in a mixture of dioxane (16 ml) and water (2.6 ml). The suspension was allowed to stir at 80° C. for a duration of 24 hours. The solvent was evaporated in high vacuum and the residue was purified by column chromatography (silica gel, Petrol ether/EtOAc 4:1) to obtain Compound 66 as an off-white solid (520 mg, 75%).

HPLC-MS [M+H]$^+$ 429.22; MP: 135-136° C.; $^1$H NMR (500 MHz, CDCl$_3$) δ 7.97-7.90 (m, 2H), 7.87-7.74 (m, 4H), 7.62-7.53 (m, 2H), 7.04 (d, J=9.1 Hz, 1H), 4.50 (dt, J=13.6, 4.0 Hz, 2H), 4.17 (q, J=7.1 Hz, 2H), 3.15 (t, J=12.3 Hz, 2H), 2.61 (tt, J=11.0, 4.0 Hz, 1H), 2.06 (dd, J=13.4, 3.7 Hz, 2H), 1.89-1.77 (m, 2H), 1.27 (t, J=7.1 Hz, 3H); $^{13}$C NMR (126 MHz, CDCl$_3$) δ 199.02, 174.68, 157.41, 141.73, 137.69, 131.57, 131.31, 131.05, 130.24, 129.24, 128.64, 127.25, 125.40, 123.73, 123.53, 122.98, 110.36, 60.54, 44.83, 41.46, 27.96, 14.24.

In an embodiment, the method of synthesizing Compound 67 (ethyl 1-(6-(pyridin-4-yl)quinolin-2-yl)pyrrolidine-3-carboxylate) is as follows:

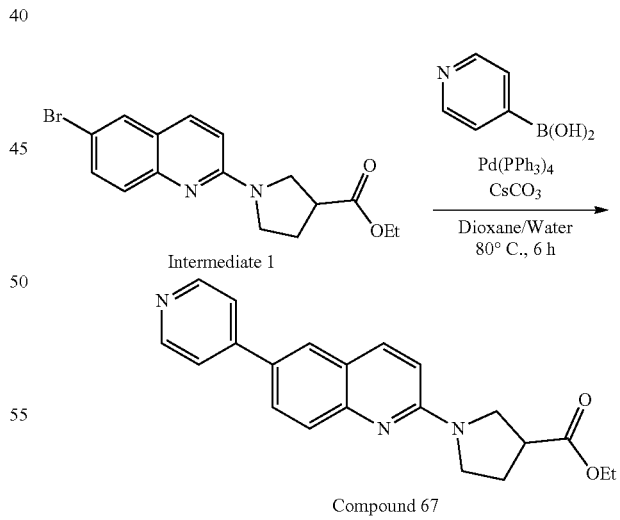

Intermediate 1

Compound 67

Tetrakis(triphenylphosphine)palladium(0) (127 mg, 0.11 mmol) was added to a stirring suspension of intermediate 1 (ethyl 1-(6-bromoquinolin-2-yl)piperidine-4-carboxylate) (800 mg, 2.3 mmol), pyridine 4 ylboronic acid (310 mg, 2.5 mmol) and caesium carbonate (4 ml, 3M solution) in a mixture of dioxane (20 ml) and water (3.4 ml). The suspension was allowed to stir at 80° C. for a duration of 6 hours.

The solvent was evaporated in high vacuum and the residue was purified by column chromatography (silica gel, Petrol ether/EtOAc 1:2). The product was recrystallized from isop and Compound 67 was isolated as a yellow solid (279 mg, 50%).

HPLC-MS [M+H]+ 348.20; MP: 145-147° C.; $^1$H NMR (500 MHz, CDCl$_3$) δ 8.67-8.62 (m, 2H), 7.93 (d, J=9.0 Hz, 1H), 7.90-7.79 (m, 3H), 7.61-7.56 (m, 2H), 6.78 (d, J=8.9 Hz, 1H), 4.20 (q, J=7.1 Hz, 2H), 4.03-3.64 (m, 4H), 3.30-3.20 (m, 1H), 2.39-2.31 (m, 2H), 1.29 (t, J=7.1 Hz, 3H); $^{13}$C NMR (126 MHz, CDCl$_3$) δ 173.18, 167.28, 150.15, 148.04, 137.81, 131.05, 128.26, 126.75, 125.93, 122.64, 121.31, 110.82, 61.07, 49.40, 46.58, 43.05, 28.69, 14.23.

In an embodiment, the method of synthesizing Compound 68 (ethyl 1-(6-(benzo[b]thiophen-2-yl)quinolin-2-yl)piperidine-4-carboxylate) is as follows:

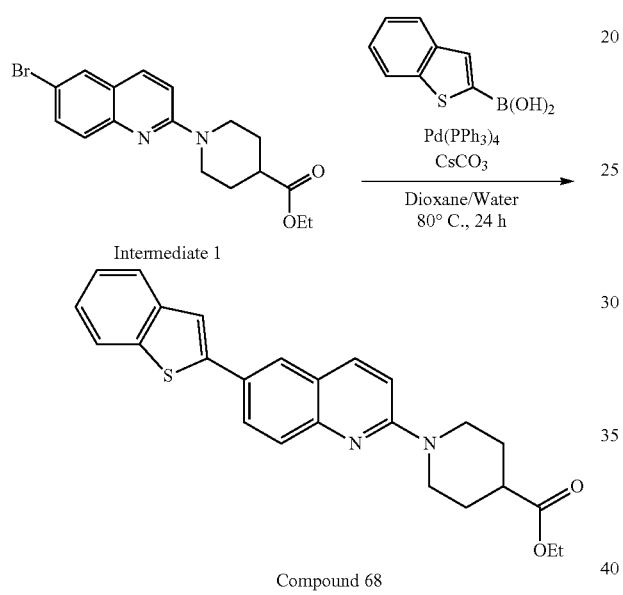

Compound 68

Tetrakis(triphenylphosphine)palladium(0) (90 mg, 0.08 mmol) was added to a stirring suspension of Intermediate 1 (ethyl 1-(6-bromoquinolin-2-yl)piperidine-4-carboxylate) (600 mg, 1.6 mmol), benzo[b]thiophen-2-ylboronic acid (323 mg, 1.8 mmol) and caesium carbonate (3 ml, 3M solution) in a mixture of dioxane (15 ml) and water (2.6 ml). The suspension was allowed to stir at 80° C. for a duration of 24 hours. The solvent was evaporated in high vacuum and the residue was purified by column chromatography (silica gel, Petrol ether/EtOAc 8:1) to obtain Compound 68 as a light brown solid (100 mg, 12%).

HPLC-MS [M+H]+ 417.20; MP: 199-201° C.; $^1$H NMR (500 MHz, CDCl$_3$) δ 8.02-7.86 (m, 3H), 7.89-7.69 (m, 3H), 7.58 (s, 1H), 7.39-7.27 (m, 2H), 7.02 (d, J=9.1 Hz, 1H), 4.49 (dt, J=13.8, 4.0 Hz, 2H), 4.17 (q, J=7.1 Hz, 2H), 3.21-3.09 (m, 2H), 2.60 (tt, J=11.0, 4.0 Hz, 1H), 2.10-2.01 (m, 2H), 1.88-1.76 (m, 2H), 1.28 (t, J=7.1 Hz, 3H); $^{13}$C NMR (126 MHz, CDCl$_3$) δ 174.66, 169.30, 144.30, 140.91, 140.07, 139.32, 137.62, 127.99, 127.97, 124.70, 124.52, 124.15, 123.40, 122.22, 118.95, 110.37, 6055, 44.82, 41.43, 27.96, 14.25.

In an embodiment, the method of synthesizing Compound 69 (ethyl 1-(6-(2-(trifluoromethyl)phenyl)quinolin-2-yl)piperidine-4-carboxylate) is as follows:

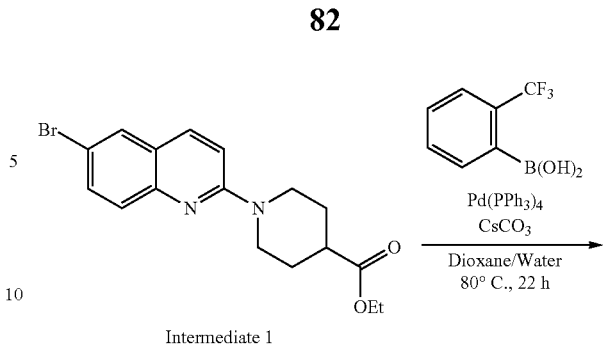

Intermediate 1

Compound 69

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (2-(trifluoromethyl)phenyl)boronic acid (345 mg, 1.8 mmol) and caesium carbonate (3 ml, 3M solution) in a mixture of dioxane (15 ml) and water (2.6 ml). The suspension was allowed to stir at 80° C. for a duration of 22 hours. The solvent was evaporated in high vacuum and the residue was purified by column chromatography (silica gel, Petrol ether/EtOAc 6:1) to obtain Compound 69 as a colourless solid (509 mg, 70%).

HPLC-MS [M+H]+ 429.15; MP: 168-170° C.; $^1$H NMR (400 MHz, CDCl$_3$) δ 8.58-8.30 (m, 2H), 7.96-7.85 (m, 2H), 7.82-7.75 (m, 1H), 7.75-7.60 (m, 3H), 7.49 (d, J=7.6 Hz, 1H), 4.62-4.48 (m, 2H), 4.11 (q, J=7.1 Hz, 2H), 3.59-3.48 (m, 2H), 2.84 (tt, J=10.5, 6.1 Hz, 1H), 2.05 (dd, J=14.1, 3.7 Hz, 2H), 1.85-1.71 (m, 2H), 1.20 (t, J=7.1 Hz, 3H); $^{13}$C NMR (101 MHz, CDCl$_3$) δ 178.71, 144.41, 137.97, 137.68, 137.50, 133.75, 133.42, 133.18, 132.40, 132.11, 131.42, 131.37, 130.69, 127.97, 125.53, 118.45, 51.79, 44.63, 32.72, 19.30.

In an embodiment, the method of synthesizing Compound 70 (ethyl 1-(6-(2-(trifluoromethoxy)phenyl)quinolin-2-yl)piperidine-4-carboxylate) is as follows:

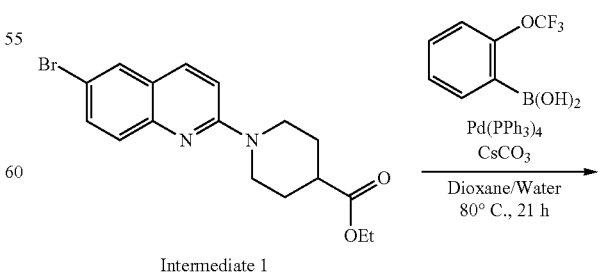

Intermediate 1

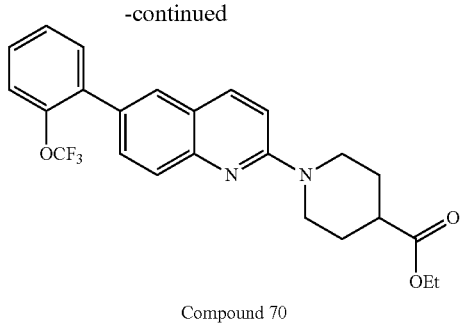

Compound 70

Tetrakis(triphenylphosphine)palladium(0) (90 mg, 0.08 mmol) was added to a stirring suspension of intermediate 1 (ethyl 1-(6-bromoquinolin-2-yl)piperidine-4-carboxylate) (600 mg, 1.6 mmol), (2-(trifluoromethoxy)phenyl)boronic acid (354 mg, 1.8 mmol) and caesium carbonate (3 ml, 3M solution) in a mixture of dioxane (15 ml) and water (2.6 ml). The suspension was allowed to stir at 80° C. for a duration of 21 hours. The solvent was evaporated in high vacuum and the residue was purified by column chromatography (silica gel, Petrol ether/EtOAc 6:1) to obtain Compound 70 as a colourless solid (564 mg, 75%).

HPLC-MS [M+H]$^+$ 445.12; MP: 161-164° C.; $^1$H NMR (400 MHz, CDCl$_3$) δ 8.49-8.37 (m, 2H), 8.04 (d, J=2.0 Hz, 1H), 7.90-7.83 (m, 1H), 7.68-7.48 (m, 5H), 4.60-4.51 (m, 2H), 4.10 (q, J=7.1 Hz, 2H), 3.58-3.45 (m, 2H), 2.84 (ddt, J=15.0, 10.6, 4.7 Hz, 1H), 2.05 (dd, J=13.6, 3.9 Hz, 21H), 1.85-1.70 (m, 2H), 1.20 (t, J=7.1 Hz, 3H); $^{13}$C NMR (126 MHz, CDCl$_3$) δ 173.44, 151.64, 146.13, 143.11, 137.78, 134.27, 133.37, 131.41, 129.48, 127.79, 127.41, 121.60, 120.82, 120.31, 111.09, 60.98, 47.85, 39.73, 27.90, 14.16.

In an embodiment, the method of synthesizing Compound 71 (ethyl 1-(6-(4-fluoro-2-methoxyphenyl)quinolin-2-yl)piperidine-4-carboxylate) is as follows:

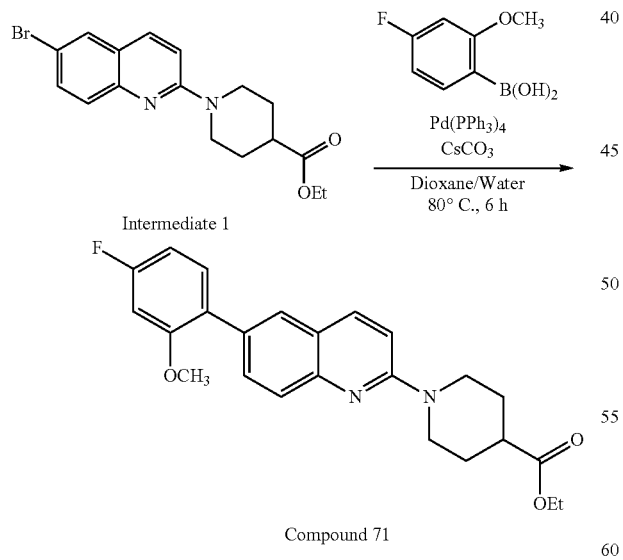

Compound 71

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (4-fluoro-2-methoxyphenyl)boronic acid (311 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 71 as a colourless solid (442 mg, 65%).

HPLC-MS [M+H]$^+$ 409.24; MP: 93-96° C.; $^1$H NMR (400 MHz, CDCl$_3$) δ 7.92 (d, J=9.2 Hz, 1H), 7.78-7.67 (m, 3H), 7.40-7.31 (m, 1H), 7.03 (d, J=9.2 Hz, 1H), 6.82-6.71 (m, 2H), 4.50 (dt, J=13.4, 3.9 Hz, 2H), 4.19 (q, J=7.1 Hz, 2H), 3.84 (s, 3H), 3.22-3.10 (m, 2H), 2.62 (tt, J=11.0, 4.0 Hz, 1H), 2.07 (dd, J=13.5, 3.8 Hz, 2H), 1.92-1.77 (m, 2H), 1.30 (t, J=7.1 Hz, 3H); $^{13}$C NMR (101 MHz, CDCl$_3$) δ 174.72, 164.17, 161.73, 157.65, 137.71, 131.51, 127.44, 126.44, 122.66, 109.94, 107.24, 107.03, 99.58, 99.33, 60.50, 55.80, 45.04, 41.48, 27.91, 14.24.

In an embodiment, the method of synthesizing Compound 72 (ethyl 1-(6-(4-methoxy-3-(trifluoromethyl)phenyl)quinolin-2-yl)piperidine-4-carboxylate) is as follows:

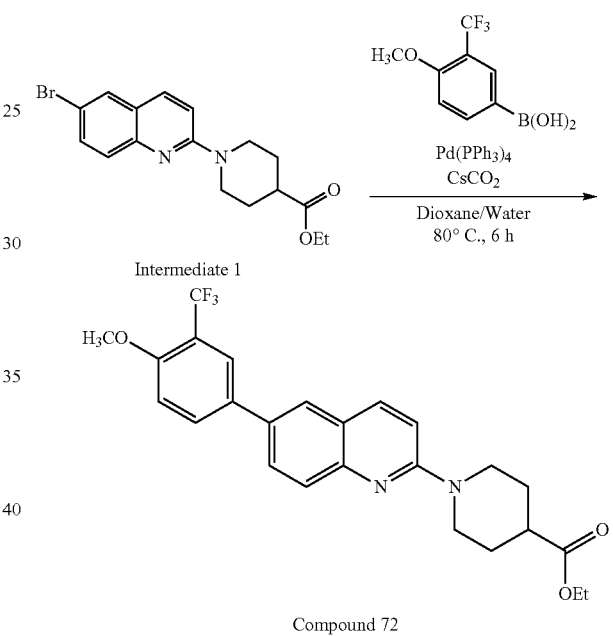

Compound 72

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (4-methoxy-3-(trifluoromethyl)phenyl)boronic acid (402 mg, 1.83 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 72 as a colourless solid (749 mg, 98%).

HPLC-MS [M+H]$^+$ 459.10; MP: 137-141° C.; $^1$H NMR (400 MHz, CDCl$_3$) δ 7.95 (d, J=9.2 Hz, 1H), 7.86 (d, J=2.4 Hz, 2H), 7.80-7.72 (m, 3H), 7.09 (d, J=8.6 Hz, 1H), 7.04 (d, J=9.2 Hz, 1H), 4.49 (dt, J=13.5, 4.0 Hz, 2H), 4.17 (q, J=7.1 Hz, 2H), 3.96 (s, 3H), 3.25-3.10 (m, 2H), 2.62 (tt, J=10.9, 4.0 Hz, 1H), 2.12-2.02 (m, 2H), 1.92-1.77 (m, 2H), 1.27 (t, J=7.2 Hz, 3H); $^{13}$C NMR (101 MHz, CDCl$_3$) δ 174.57, 156.67, 132.90, 132.14, 131.49, 128.56, 128.44, 127.74, 125.65, 125.03, 124.66, 122.84, 122.32, 119.25, 118.94, 112.48, 110.39, 60.58, 56.13, 45.14, 41.27, 27.93, 14.23.

In an embodiment, the method of synthesizing Compound 73 (ethyl 1-(6-(4-chloro-3-methoxyphenyl)quinolin-2-yl)piperidine-4-carboxylate) is as follows:

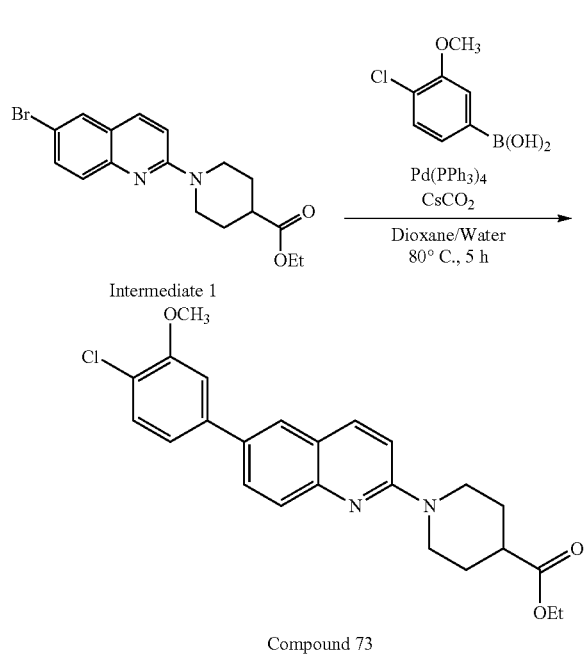

Intermediate 1

Compound 73

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (4-chloro-3-methoxyphenyl)boronic acid (371 mg, 1.99 mmol) and caesium carbonate (3 ml, 3M solution) in a mixture of dioxane (16 ml) and water (2.6 ml). The suspension was allowed to stir at 80° C. for a duration of 5 hours. The solvent was evaporated in high vacuum and the residue was purified by column chromatography (silica gel, Petrol ether/EtOAc 4:1) to obtain Compound 73 as a colourless solid (420 mg, 60%).

HPLC-MS [M+H]$^+$ 425.18; MP: 146-148° C.; $^1$H NMR (400 MHz, CDCl$_3$) δ 8.28-7.94 (m, 2H), 7.85-7.68 (m, 2H), 7.47-7.40 (m, 1H), 7.21-7.13 (m. 2H), 7.08-7.01 (m, 1H), 4.55-4.45 (m, 2H), 4.16 (q, J=7.1 Hz, 21H), 3.99 (s, 3H), 3.39-3.21 (m, 2H), 2.64 (tt, J=10.7, 4.1 Hz, 111), 2.19-2.02 (m, 2H), 1.96-1.76 (m, 2H), 1.27 (t, J=7.1 Hz, 311); $^{13}$C NMR (126 MHz, CDCl$_3$) δ 174.45, 156.67, 155.22, 131.79, 130.44, 130.02, 125.14, 122.53, 121.55, 119.97, 112.73, 110.83, 110.49, 108.10, 100.68, 60.67, 56.25, 45.41, 41.06, 27.91, 14.24.

In an embodiment, the method of synthesizing Compound 74 (ethyl 1-(6-(3-fluorophenyl)quinolin-2-yl)piperidine-4-carboxylate) is as follows:

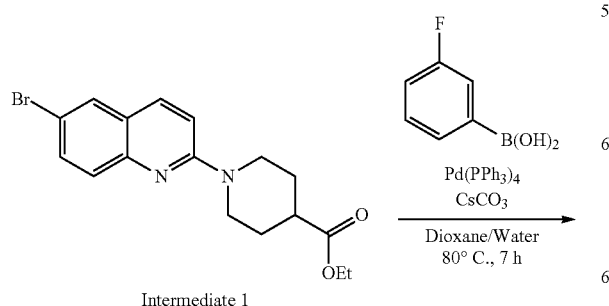

Intermediate 1

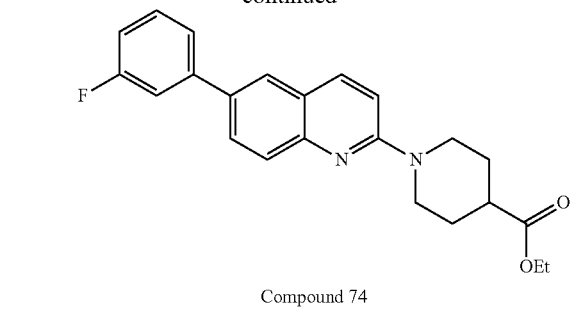

Compound 74

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (43-fluorophenyl)boronic acid (280 mg, 1.99 mmol) and caesium carbonate (3 ml, 3M solution) in a mixture of dioxane (16 ml) and water (2.6 ml). The suspension was allowed to stir at 80° C. for a duration of 7 hours. The solvent was evaporated in high vacuum and the residue was purified by column chromatography (silica gel, Petrol ether/EtOAc 4:1) to obtain Compound 74 as an off-white solid (421 mg, 62%).

HPLC-MS [M+H]$^+$ 379.24; MP: 120-123° C.; $^1$H NMR (400 MHz, CDCl$_3$) δ 7.94 (d, J=9.2 Hz, 1H), 7.91-7.74 (m, 3H), 7.53-7.31 (m, 3H), 7.08-6.98 (m, 2H), 4.49 (dt, J=13.5, 4.0 Hz, 2H), 4.17 (q, J=7.1 Hz, 2H), 3.27-3.11 (m, 2H), 2.61 (tt, J=10.9, 4.0 Hz, 1H), 2.07 (dd, J=13.5, 3.8 Hz, 2H), 1.91-1.76 (m, 2H), 1.27 (t, J=7.1 Hz, 3H); $^{13}$C NMR (126 MHz, CDCl$_3$) δ 174.64, 164.25, 162.30, 157.03, 143.15, 138.01, 133.92, 130.29, 128.89, 125.24, 122.85, 122.60, 122.61, 113.73, 110.34, 60.57, 44.99, 41.38, 27.95, 14.26.

In an embodiment, the method of synthesizing Compound 75 (ethyl 1-(6-(3-chloro-4-fluorophenyl)quinolin-2-yl)piperidine-4-carboxylate) is as follows:

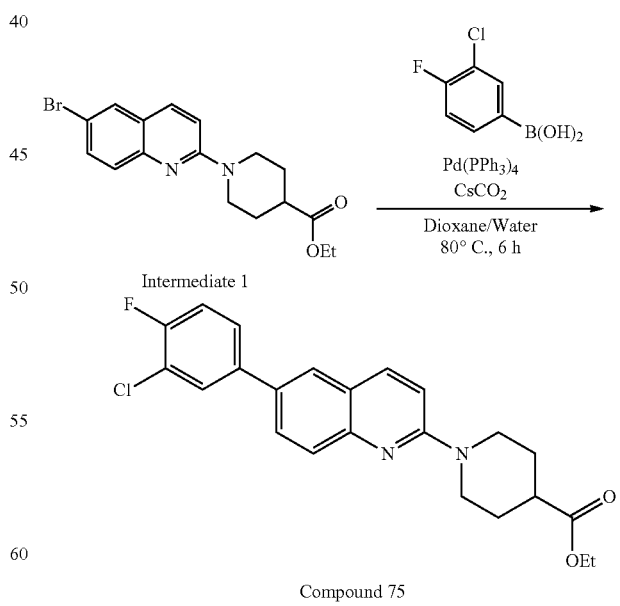

Intermediate 1

Compound 75

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (3-chloro-4-fluorophenyl)boronic acid (345 mg, 1.99 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 4:1) to obtain Compound 75 as a colourless solid (664 mg, 97%).

HPLC-MS [M+H]⁺ 413.16; MP: 143-146° C.; ¹H NMR (400 MHz, CDCl₃) δ 7.93 (d, J=9.2 Hz, 1H), 7.86 (m, 1H), 7.78-7.65 (m, 3H), 7.55-7.44 (m, 1H), 7.26-7.17 (m, 1H), 7.04 (d, J=9.2 Hz, 1H), 4.49 (dt, J=13.5, 3.9 Hz, 2H), 4.16 (q, J=7.1 Hz, 2H), 3.25-3.14 (m, 2H), 2.62 (tt, J=10.8, 4.0 Hz, 1H), 2.07 (dd, J=13.5, 3.8 Hz, 2H), 1.91-1.76 (m, 2H), 1.27 (t, J=7.1 Hz, 3H); ¹³C NMR (101 MHz, CDCl₃) δ 174.55, 158.70, 156.23, 138.07, 129.05, 126.64, 126.57, 125.11, 122.74, 121.37, 117.17, 116.95, 116.74, 110.45, 60.59, 45.09, 41.26, 27.92, 14.23.

In an embodiment, the method of synthesizing Compound 76 (ethyl 1-(6-(2-methoxypyridin-3-yl)quinolin-2-yl)piperidine-4-carboxylate) is as follows:

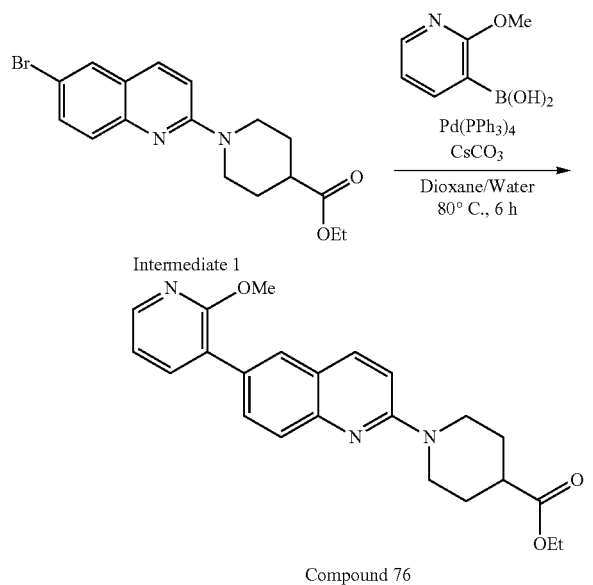

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (2-methoxypyridin-3-yl)boronic acid (305 mg, 1.99 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 76 as an off-white solid (515 mg, 79%).

HPLC-MS [M+H]⁺ 392.26; MP: 105-107° C.; ¹H NMR (400 MHz, CDCl₃) δ 8.22-8.12 (m, 1H), 7.90 (d, J=9.1 Hz, 1H), 7.84-7.61 (m, 4H), 7.05-6.95 (m, 2H), 4.48 (dt, J=13.6, 3.9 Hz, 2H), 4.16 (q, J=7.1 Hz, 2H), 4.00 (s, 3H), 3.13 (ddd, J=13.9, 11.4, 2.8 Hz, 2H), 2.59 (tt, J=11.0, 4.0 Hz, 1H), 2.04 (dd, J=13.4, 3.8 Hz, 2H), 1.89-1.74 (m, 2H), 1.27 (t, J=7.1 Hz, 3H); ¹³C NMR (101 MHz, CDCl₃) δ 174.73, 161.01, 157.46, 147.41, 145.38, 138.51, 137.62, 130.78, 130.58, 127.46, 126.28, 124.54, 122.69, 117.14, 110.00, 60.50, 53.53, 44.89, 41.52, 27.92, 14.24.

In an embodiment, the method of synthesizing Compound 77 (ethyl 1-(6-(5-fluoropyridin-3-yl)quinolin-2-yl)piperidine-4-carboxylate) is as follows:

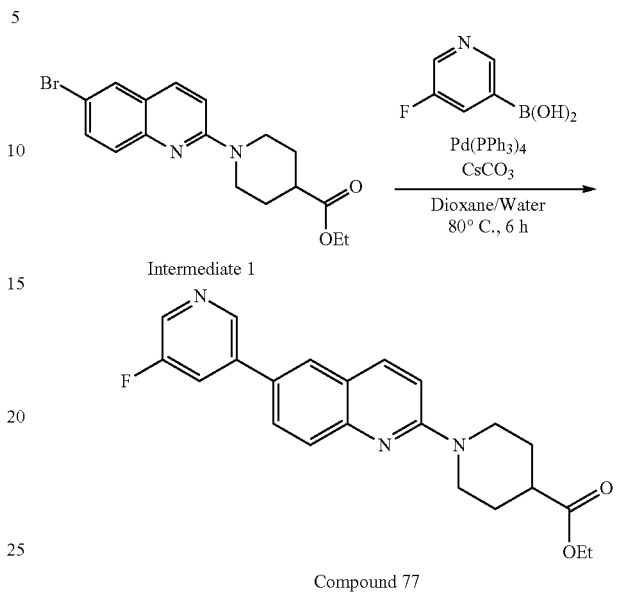

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (5-fluoropyridin-3-yl)boronic acid (280 mg, 1.99 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1) to obtain Compound 77 as an off-white solid (540 mg, 86%).

HPLC-MS [M+H]⁺ 380.21; MP: 113-115° C.; ¹H NMR (400 MHz, CDCl₃) δ 8.77-8.74 (m, 1H), 8.43 (d, J=2.7 Hz, 1H), 7.93 (d, J=9.2 Hz, 1H), 7.86-7.71 (m, 3H), 7.70-7.64 (m, 1H), 7.05 (d, J=9.2 Hz, 1H), 4.50 (dt, J=13.9, 3.9 Hz, 2H), 4.16 (q, J=7.1 Hz, 2H), 3.15 (ddd, J=13.8, 11.4, 2.9 Hz, 2H), 2.61 (tt, J=11.0, 4.0 Hz, 1H), 2.11-2.00 (m, 2H), 1.88-1.77 (m, 2H), 1.27 (t, J=7.1 Hz, 3H); ¹³C NMR (101 MHz, CDCl₃) δ 174.65, 161.07, 158.52, 157.55, 143.94, 138.18, 137.64, 136.20, 129.84, 128.29, 127.52, 125.71, 122.96, 120.87, 110.49, 60.55, 44.72, 41.43, 27.93, 14.23.

In an embodiment, the method of synthesizing Compound 78 (ethyl 1-(6-(3-fluoropyridin-4-yl)quinolin-2-yl)piperidine-4-carboxylate) is as follows:

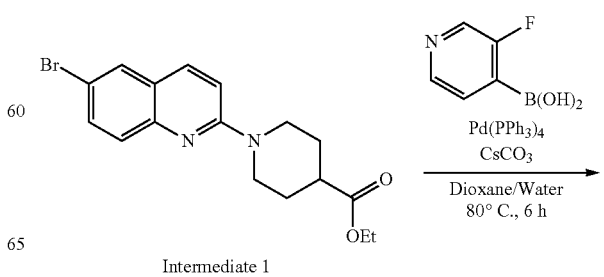

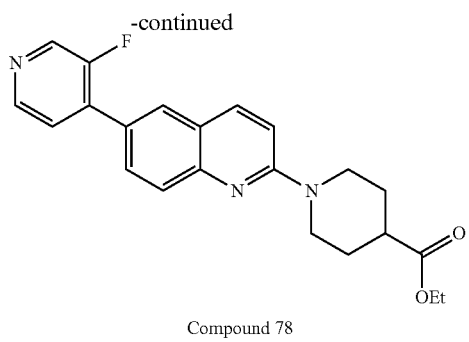

Compound 78

Tetrakis(triphenylphosphine)palladium(0) (96 mg, 0.08 mmol) was added to a stirring suspension of intermediate 1 (ethyl 1-(6-bromoquinolin-2-yl)piperidine-4-carboxylate) (600 mg, 1.66 mmol), (3-fluoropyridin-4-yl)boronic acid (280 mg, 1.99 mmol) and caesium carbonate (3 ml, 3M solution) in a mixture of dioxane (16 ml) and water (2.6 ml). The suspension was allowed to stir at 80° C. for a duration of 6 hours. The solvent was evaporated in high vacuum and the residue was purified by column chromatography (silica gel, Petrol ether/EtOAc 2:1-1:2) to obtain Compound 78 as a yellow solid (100 mg, 16%).

HPLC-MS [M+H]$^+$ 380.16; MP: 97-101° C.; $^1$H NMR (400 MHz, CDCl$_3$) δ 8.63-8.51 (m, 1H), 8.47 (d, J=5.0 Hz, 1H), 8.08-7.85 (m, 3H), 7.83-7.75 (m, 1H), 7.49 (m, 1H), 7.05 (d, J=9.3 Hz, 1H), 4.57-4.47 (m, 2H), 4.16 (q, J=7.1 Hz, 2H), 3.29-3.12 (m, 2H), 2.63 (tt, J=10.8, 4.0 Hz, 1H), 2.07 (dd, J=13.4, 3.9 Hz, 2H), 1.90-1.76 (m, 2H), 1.27 (t, J=7.1 Hz, 3H); $^{13}$C NMR (101 MHz, CDCl$_3$) δ 174.52, 171.94, 165.46, 146.00, 145.95, 139.17, 138.91, 135.76, 132.10, 129.87, 128.02, 126.84, 124.01, 122.50, 110.41, 60.59, 44.95, 41.28, 27.93, 14.23.

In an embodiment, the method of synthesizing compounds of Intermediate 2 (Methyl 1-(6-bromoquinolin-2-yl)piperidine-4-carboxylate) is as follows:

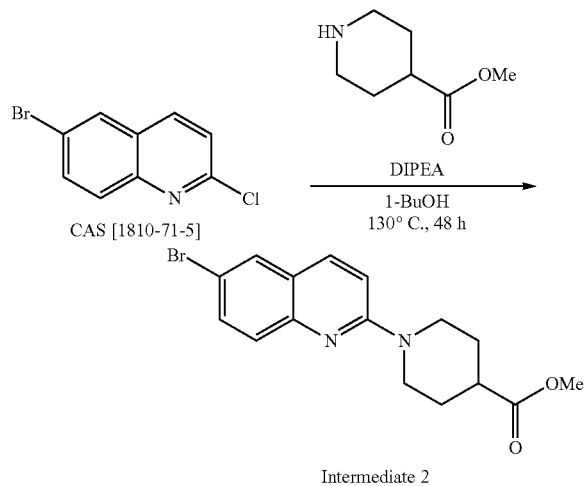

Intermediate 2

DIPEA (5 ml) was added to a suspension of 2-Chloro-6-bromoquinoline (1 g, 4.1 mmol) and methyl isonipecotate (650 mg, 4.5 mmol) in 1-BuOH (20 ml) and the mixture was allowed to stir at 130° C. for a duration of 24 hours. The solvent was evaporated, and the resulting residue was purified by column chromatography (silica gel, Petrol ether/EtOAc 2:1) to obtain Intermediate 2 as an off-white solid (572 mg, 98%).

In an embodiment, the method of synthesizing Compound 79 (methyl 1-(6-(pyridin-4-yl)quinolin-2-yl)piperidine-4-carboxylate) is as follows:

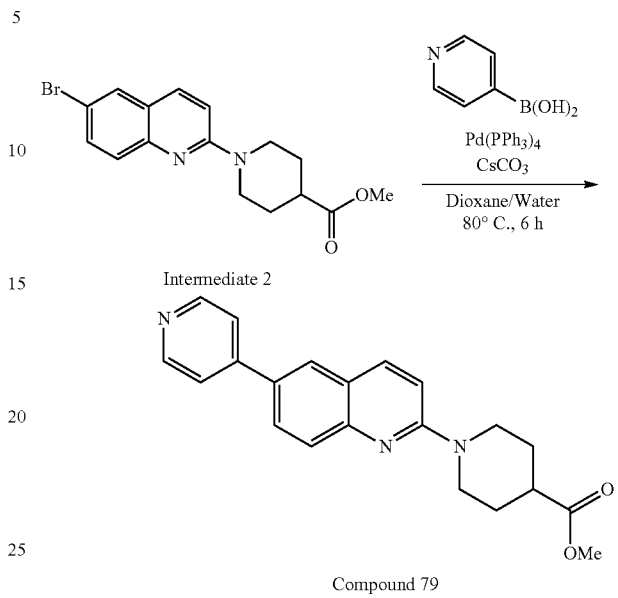

Compound 79

Tetrakis(triphenylphosphine)palladium(0) (80 mg, 0.07 mmol) was added to a stirring suspension of intermediate 2 (methyl 1-(6-bromoquinolin-2-yl)piperidine-4-carboxylate) (480 mg, 1.39 mmol), pyridin-4-ylboronic acid (285 mg, 1.66 mmol) and caesium carbonate (2.4 ml, 3M solution) in a mixture of dioxane (10 ml) and water (2 ml). The suspension was allowed to stir at 80° C. for a duration of 5 hours. The solvent was evaporated in high vacuum and the residue was purified by column chromatography (silica gel, Petrol ether/EtOAc 2:1) Impure product was dissolved in hot isop, was filtered while hot and the filtrate was allowed to cool down at 0° C. Crystals of product were collected by filtration. The product compound 79 was isolated as an off-white solid (204 mg, 42%).

HPLC-MS [M+H]$^+$ 348.13; MP: 153-155° C.; $^1$H NMR (400 MHz, CDCl$_3$) δ 8.70-8.61 (m, 2H), 7.93 (d, J=9.2 Hz, 1H), 7.87 (d, J=2.1 Hz, 1H), 7.85-7.73 (m, 2H), 7.62-7.55 (m, 2H), 7.04 (d, J=9.2 Hz, 1H), 4.50 (dt, J=13.4, 3.9 Hz, 2H), 3.71 (s, 3H), 3.15 (ddd, J=13.9, 11.5, 2.9 Hz, 2H), 2.63 (tt, J=11.0, 4.0 Hz, 1H), 2.05 (dd, J=13.5, 3.8 Hz, 2H), 1.89-1.80 (m, 2H); $^{13}$C NMR (101 MHz, CDCl$_3$) δ 175.05, 157.59, 150.22, 148.44, 148.03, 137.74, 131.49, 128.01, 127.40, 125.62, 122.91, 121.32, 110.36, 51.79, 44.69, 41.32, 27.92.

In an embodiment, the preferred compounds of general formula I are as follows:
1-(6-(4-(trifluoromethoxy)phenyl)quinolin-2-yl)piperidine-4-carboxylic acid;
ethyl 1-(6-(2-methoxypyrimidin-5-yl)quinolin-2-yl)piperidine-4-carboxylate;
ethyl 1-(6-(3-fluorophenyl)quinolin-2-yl)piperidine-4-carboxylate;
1-(6-(3-fluoro-4-isopropoxyphenyl)quinolin-2-yl)piperidine-4-carboxylic acid;
1-(6-(3-fluorophenyl)quinolin-2-yl)piperidine-4-carboxylic acid;
ethyl 1-(6-(6-methoxypyridin-3-yl)quinolin-2-yl)piperidine-4-carboxylate;

ethyl 1-(6-(2-chloro-4-methoxyphenyl)quinolin-2-yl)piperidine-4-carboxylate;
1-(6-(4-methoxyphenyl)quinolin-2-yl)piperidine-4-carboxylic acid;
ethyl 1-(6-(4-methoxy-2-(trifluoromethyl)phenyl)quinolin-2-yl)piperidine-4-carboxylate hydrochloride;
ethyl 1-(6-(3-(trifluoromethoxy)phenyl)quinolin-2-yl)piperidine-4-carboxylate;
ethyl 1-(6-(3-hydroxyphenyl)quinolin-2-yl)piperidine-4-carboxylate;
1-(6-(3-(trifluoromethoxy)phenyl)quinolin-2-yl)piperidine-4-carboxylic acid;
ethyl 1-(6-(6-methylpyridin-3-yl)quinolin-2-yl)piperidine-4-carboxylate;
ethyl 1-(6-(pyridin-2-yl)quinolin-2-yl)piperidine-4-carboxylate;
ethyl 1-(6-(3-fluoro-4-methoxyphenyl)quinolin-2-yl)piperidine-4-carboxylate;
ethyl 1-(6-(4-chloro-3-fluorophenyl)quinolin-2-yl)piperidine-4-carboxylate;
ethyl 1-(6-(2-(trifluoromethyl)phenyl)quinolin-2-yl)piperidine-4-carboxylate;
ethyl 1-(6-(4-fluoro-2-methoxyphenyl)quinolin-2-yl)piperidine-4-carboxylate; or
a pharmaceutically acceptable salt, hydrate, solvate, N-oxide, stereoisomer, stereoisomer, in particular diastereoisomer, enantiomer or atropisomers, or mixtures thereof, polymorph or ester thereof.

Example 2

In an embodiment, the in vitro cytotoxicity assay was carried out as follows. The in vitro cytotoxicity assay was performed in HepG2 cell line using a tetrazolium reduction assay for cell viability evaluation (MTS reduction as described by Cory A. et al (*Cancer Commun.* 1991, 3 (7), 207-212)). The assay was performed in 96 well plates for 48 h at 37° C. and 5% $CO_2$ in incubation medium (low glucose DMEM with Glutamax, 10% FBS, 1% Pen/Strep and DMSO). Cells were exposed to 8 different compound concentrations in successive dilutions (usually, base 2), plus a positive control (a compound in a concentration known to decrease cell viability above 50%) and a negative control (incubation medium). Six replicate wells were assayed for each condition. Compound stock solutions were prepared in DMSO at 20 mM, whenever possible, filter sterilized, aliquoted and stored at −20° C. The maximum compound concentrations tested depend on its solubility in incubation medium, and on the maximum DMSO percentage allowable without loss of cell viability. At the end of the incubation period, tetrazolium reagent was added (CellTiter 96® $AQ_{ueous}$ Solution from Promega); cells were incubated for another 3 hours in order to promote tetrazolium reduction to formazan by viable cells. The amount of soluble formazan produced was evaluated by 490 nm absorbance reading in a spectrophotometer plate reader. The average absorbance from the negative control wells corresponded to 100% cell viability; the absorbance obtained from each test condition were then transformed into a cell viability percentage—these results were plotted against compound concentration and a non-linear regression fit was made. Whenever possible, $IC_{50}$ was calculated as the concentration of compound that reduces cell viability by 50%.

Example 3

In an embodiment, the *Mycobacterium tuberculosis* susceptibility assay REMA was carried out as follows. *M. tuberculosis* susceptibility was accessed by exposing susceptible H37Rv *M. tuberculosis*, in particular *M. tuberculosis* strain ATCC 25618, to the different compounds and evaluating its growth inhibition by REMA (resazurin microtiter assay) method based on Palomino J C et al (*Mycobacterium tuberculosis Antimicrob. Agents Chemother.* 2002, 46, 8, 2720-2722). The assay was performed in 96 well plates for 6 days at 37° C. in Middlebrook 7H9 medium. Cells were exposed to 8 different compound concentrations in two-fold serial dilutions; incubation medium was used as negative control and 2 positive controls were accessed: Rifampicin in a concentration known to inhibit growth and Moxifloxacin in 8 different concentrations, from no growth inhibition to full growth inhibition. Compound stock solutions were prepared in DMSO in a concentration at least 40× higher than the maximum concentration tested. At the end of the incubation period, resazurin was added and cells were incubated for another 2 days in order to promote resazurin colour change from blue to pink every time growth as occurred. Colours were recorded and the lowest concentration in which no colour change was observed (the last blue well) was assumed to be the minimum inhibitory concentration (MIC) for that compound in *M. tuberculosis*.

Example 4

In an embodiment, the metabolic stability assay was carried out as follows. Metabolic stability was assessed by incubating test compounds in 96-well plates in 5 aliquots of 40 μL each (one for each time point) in liver microsomal incubation medium. This medium contained $MgCl_2$ (3.3 mM), NADPH-cofactor system (NADPH (3 mM), glucose-6-phosphate (5.3 mM), glucose-6-phosphate dehydrogenase (0.67 units/ml)) and 0.42 mg of liver microsomal protein per ml in phosphate buffer (100 mM, pH 7.4). Control incubations were performed replacing the NADPH-cofactor system by phosphate buffer. Test compounds (1 μM, final solvent concentration 1.6%) were incubated with microsomes at 37° C. and 100 rpm orbital shaking, Imipramine and Propranolol were incubated in parallel as reference compounds. Each reaction was performed in duplicate. Five time points over 60 minutes were analysed. The reactions were stopped by adding 12 volumes of 90% acetonitrile in water to incubation aliquots, followed by protein sedimentation by centrifugation. Supernatants were analysed using a Shimadzu VP HPLC system with a reverse phase HPLC column, coupled with tandem mass spectrometer API 3000 (PE Sciex). The TurbolonSpray source was used in both positive and negative ion modes. Acquisition and analysis of the data were performed using Analyst 1.5.2 software (PE Sciex). The elimination constant ($k_{el}$), half-life ($t_{1/2}$) and intrinsic clearance ($Cl_{int}$) were determined in plot of ln(AUC) versus time, using linear regression analysis for each test and reference compound.

Example 5

In an embodiment, the distribution coefficient (Log D) determination assay was carried out as follows. Test compounds were incubated in Eppendorf-type polypropylene microtubes in triplicates: a 5 μL aliquot of a 10 mM DMSO stock of each test compound were added into the previously mutually saturated mixture containing 500 μL of phosphate buffer saline (pH 7.4) and 500 μL of octanol. The solution was allowed to mix in a rotator for 1 hour at 30 rpm. Phase separation was assured by centrifugation. The octanol phase was diluted 100-fold with 40% acetonitrile in water for analysis, and aqueous phase was analysed without dilution. Mebendazole was used as a reference compound. All samples (both phases) were analysed in a Shimadzu VP HPLC system with a reverse phase column, coupled with tandem mass spectrometer API 3000 (PE Sciex). The TurbolonSpray ion source was used in positive ion mode. Acquisition and analysis of the data were performed using Analyst 1.5.2 software. Distribution coefficients of the tested compounds were calculated as the logarithm of the partition ratios (D) in both solvents, according to the equation below.

$$D = \frac{100 \cdot S_O}{S_P}$$

where:
$S_O$—peak area of the compound in octanol phase
$S_P$—peak area of the compound in phosphate buffer saline phase Example 6

In an embodiment, the pKa determination assay was carried out as follows. The tendency of a compound to donate a proton is measured as its acid ionization constant (dissociation constant), or Ka. A more practical scale of representing acidity is pKa which is the negative logarithm of the Ka (pKa=−log Ka). The pKa determinations of the test compounds and 3 reference compounds were assessed by potentiometric titration, in accordance with the technical protocols for pKa measurement provided by Pion Inc. and Sirius Analytical Inc. Briefly, compounds pKa were determined by pH-metric method based on potentiometric acid-base titration at 25° C. The test and reference compounds were dissolved in acidified MeOH-water (1:4) solution of NaCl (150 mM, pH 2) and slowly titrated with 10 mM NaOH MeOH-water (1:4) solution. The recorded pH of the solution as a function of NaOH volume used during the titration were used to construct the titration curve. Titration of acidified NaCl solution in absence of any compound was used for blank plotting. Buffering capacity was calculated in each point of titration curve as the ratio of the NaOH flow (constant) to the pH rise velocity. The pKa value is determined from resulting plot of buffering capacity versus pH as the maximum of buffering capacity. pH-Metric method allows to measure pKa's in range between 2 and 12. Acquisition and analysis of the data were performed using SmartLogger∥1.0.14 software (Beckman Coulter). Data analysis was done using GraphPad Prism 5.01 and Excel 2010 software.

Example 7

In an embodiment, stability in human plasma (PS) assay was carried out as follows. Test compounds (1 µM, final DMSO concentration 1%) were incubated in 5 aliquots of 70 µL each (one for each time point), in duplicates, at 37° C. with 100 rpm orbital shaking. Five time points over 120 minutes have been analysed. Two reference compounds were analysed in parallel. The reactions were stopped by the addition of 420 µL of acetonitrile-water mixture (90:10) and subsequent plasma proteins sedimentation were achieved by centrifugation. Supernatants were analysed in a Shimadzu VP HPLC system with a reverse phase column, coupled with a tandem mass spectrometer API 3000 (PE Sciex). Both the positive and negative ion modes of the TurbolonSpray ion source were used. Acquisition and analysis of the data were performed using Analyst 1.5.2 software (PE Sciex). The percentage of the test compounds remaining after incubation in plasma and their half-lives ($T_{1/2}$) were calculated.

Example 8 in an embodiment, the human plasma protein binding (PPB) assay was carried out as follows. The assay was performed in a multiple-use 96-well dialysis unit (HTD96b dialyzer). Each individual well unit consisted of 2 chambers separated by a vertically aligned dialysis membrane of predetermined pore size (MWCO 12-14 kDa). 120 µl of non-diluted plasma spiked with the compound (1 µM, 1% final DMSO concentration) was added to one chamber and the same volume of phosphate buffer saline pH 7.4 to the other chamber. HTD96b dialyzer was covered with adhesive sealing film and incubated at 37° C. and 100 rpm orbital shaking for 5 hours. Verapamil was also evaluated in parallel as reference compound. For sample preparation, an aliquot of the content of each chamber was mixed with the same volume of the blank opposite matrix. In order to define non-specific loss of the compound during this assay, standard solution was created by mixing an aliquot of spiked plasma with blank buffer without dialysis. Samples were diluted 10-fold with 100% acetonitrile with subsequent plasma proteins sedimentation by centrifugation. Supernatants were analysed using a Shimadzu VP HPLC system with a reverse phase column, coupled with a tandem mass spectrometer API 3000 (PE Sciex). The both positive and negative ion modes of the TurbolonSpray ion source were used. Acquisition and analysis of the data were performed using Analyst 1.5.2 software (PE Sciex).

The percentage of plasma protein bounded compound and its recovery were calculated using the equations below:

$$\text{Protein binding} = \left(1 - \frac{\text{Peak area in buffer}}{\text{Peak area in plasma}}\right) \cdot 100\%$$

$$\text{Recovery} = \left(\frac{\text{Peak area in buffer} + \text{Peak area in plasma}}{\text{Peak area in standard solution}}\right) \cdot 100\%$$

The percentage of plasma protein bounded compound and its recovery were calculated using the values obtained for each compound in the quantification of the 3 samples (in buffer, plasma and standard solution).

Example 9

In an embodiment, PAMPA assay was carried. All steps of PAMPA assay were carried out according to pION Inc. PAMPA Explorer™ Manual. The main principle of the assay is the compound incubation in the donor chamber with aqueous buffer, which is separated from the acceptor chamber, with another buffer, by a phospholipid or hydrocarbon membrane fixed on a filter support. After the test, concentrations in the corresponding donor and acceptor chambers are measured and permeability is calculated. GIT model was simulated using GIT-0 phospholipid mix. Verapamil and quinidine (high permeability) and ranitidine (low permeability) were used as reference compounds. All compounds were tested in quadruplicates. Prisma HT buffer (pH 7.4) containing 50 µM test compound (final 0.5% DMSO concentration was added into the donor chamber. Acceptor Sink Buffer was added into each acceptor chamber. Incubation was done at room temperature for 4 hours without stirring.

After incubation, aliquots from both chambers were transferred to optic UV-Vis plates and absorbance was recorded in the range of 202-500 nm in 4 nm steps. Compounds with low UV-Vis signal were evaluated by LC-MS/MS (using a Shimadzu VP HPLC system with a reverse phase HPLC column, coupled with tandem mass spectrometer API 3000 (PE Sciex) and TurbolonSpray ion source used in positive ion mode; acquisition and analysis of the data were performed using Analyst 1.5.2 software (PE Sciex)).

Then the apparent permeability coefficient was calculated, using the formula below.

$$\log P_{app} = \log_{10}\left(-\frac{2.303 \times V_D}{2 \times \text{Area} \times \text{Time}}\right) \times \log_{10}\left(1 - 2 \times \frac{[\text{drug}]_{acc}}{[\text{drug}]_d}\right)$$

$V_D$—volume of transport buffer in donor well (0.3 ml):
Area—surface area of the lipids in the insert (effective growth area of the insert—0.3 sq.cm):
Time—time of the assay, seconds:
$[\text{drug}]_{acc}$—final OD of test compound in acceptor well:
$[\text{drug}]_d$—starting OD of test compound in a donor well The apparent permeability coefficient was calculated for each compound ($\log P_{app}$).

In an embodiment, compounds of the disclosure for example when tested in cytotoxicity assay described in example 2 typically have $IC_{50}$ value not less than 50 µM.

In an embodiment, compounds of the disclosure, when tested in susceptibility assay described in example 3 may typically have MIC lower than 15.6 µM. Compounds of the disclosure when tested in assay described in example 3 may have MIC between 3.91 µM and 15.6 µM.

In an embodiment, compounds of the disclosure were tested in assays outlined in examples 2 and 3 as described above and the following results were obtained:

TABLE 1

REMA and $IC_{50}$ results for selected compounds

| Compound Number | Name | REMA MIC | $IC_{50}$ |
|---|---|---|---|
| 2 | 1-(6-(4-(Trifluoromethoxy)phenyl)quinolin-2-yl)piperidine-4-carboxylic acid | ++++ | ++++ |
| 3 | Ethyl 1-(6-(4-hydroxyphenyl)quinolin-2-yl)piperidine-4-carboxylate | +++ | ++++ |
| 4 | Ethyl 1-(6-(2-methoxypyrimidin-5-yl)quinolin-2-yl)piperidine-4-carboxylate | ++++ | ++++ |
| 8 | Ethyl 1-(6-(3-fluorophenyl)quinolin-2-yl)piperidine-4-carboxylate | ++++ | ++++ |
| 10 | 1-(6-(3-Fluoro-4-isopropoxyphenyl)quinolin-2-yl)piperidine-4-carboxylic acid | ++++ | ++++ |
| 11 | 1-(6-(3-Fluorophenyl)quinolin-2-yl)piperidine-4-carboxylic acid | ++++ | ++++ |
| 14 | Ethyl 1-(6-(6-methoxypyridin-3-yl)quinolin-2-yl)piperidine-4-carboxylate | ++++ | ++++ |
| 15 | Ethyl 1-(6-(pyridin-4-yl)quinolin-2-yl)piperidine-4-carboxylate hydrochloride | +++ | ++++ |
| 16 | Ethyl 1-(6-(furan-2-yl)quinolin-2-yl)piperidine-4-carboxylate | +++ | ++++ |
| 18 | 1-(6-(Pyridin-4-yl)quinolin-2-yl)piperidine-4-carboxylic acid hydrochloride | +++ | ++++ |
| 19 | Ethyl 1-(6-(2-chloro-4-methoxyphenyl)quinolin-2-yl)piperidine-4-carboxylate | ++++ | +++ |
| 20 | Ethyl 1-(6-(4-methoxyphenyl)quinolin-2-yl)piperidine 4-carboxylate | +++ | ++++ |
| 21 | 1-(6-(4-Methoxyphenyl)quinolin-2-yl)piperidine-4-carboxylic acid | ++++ | ++++ |
| 22 | 1-(6-(3-Methoxyphenyl)quinolin-2-yl)piperidine-4-carboxylic acid | +++ | ++++ |
| 23 | 1-(6-(2-Chloro-4-methoxyphenyl)quinolin-2-yl)piperidine-4-carboxylic acid | +++ | ++++ |
| 24 | Ethyl 1-(6-(4-methoxy-2-(trifluoromethyl)phenyl)quinolin-2-yl)piperidine-4-carboxylate hydrochlorice | ++++ | +++ |
| 25 | Ethyl 1-(6-(3-(trifluoromethoxy)phenyl)quinolin-2-yl)piperidine-4-carboxylate | ++++ | ++++ |
| 26 | Ethyl 1-(6-(3-hydroxyphenyl)quinolin-2-yl)piperidine-4-carboxylate | ++++ | ++++ |
| 29 | 1-(6-(3-(Trifluoromethoxy)phenyl)quinolin-2-yl)piperidine-4-carboxylic acid | ++++ | ++++ |
| 30 | Ethyl 1-(6-(3-methoxyphenyl)quinolin-2-yl)piperidine-4-carboxylate | +++ | ++++ |
| 32 | Ethyl 1-(6-(3-nitrophenyl)quinolin-2-yl)piperidine-4-carboxylate | +++ | ++++ |
| 35 | Ethyl 1-(6-(6-fluoropyridin-3-yl)quinolin-2-yl)piperidine-4-carboxylate | +++ | ++++ |
| 37 | Ethyl 1-(6-(2-fluoropyridin-4-yl)quinolin-2-yl)piperidine-4-carboxylate | +++ | +++ |
| 40 | Ethyl 1-(6-(2-methylpyridin-4-yl)quinolin-2-yl)piperidine-4-carboxylate | +++ | ++ |

TABLE 1-continued

REMA and IC$_{50}$ results for selected compounds

| Compound Number | Name | REMA MIC | IC$_{50}$ |
|---|---|---|---|
| 41 | Ethyl 1-(6-(3,5-dimethoxyphenyl)quinolin-2-yl)piperidine-4-carboxylate | +++ | +++ |
| 42 | Ethyl 1-(6-(1H-indol-5-yl)quinolin-2-yl)piperidine-4-carboxylate | +++ | ++ |
| 50 | Ethyl 1-(6-(6-methylpyridin-3-yl)quinolin-2-yl)piperidine-4-carboxylate | ++++ | ++++ |
| 54 | Ethyl 1-(6-(pyridin-4-yl)quinolin-2-yl)piperidine-3-carboxylate | +++ | ++++ |
| 55 | Ethyl 1-(6-(pyridin-2-yl)quinolin-2-yl)piperidine-4-carboxylate | ++++ | +++ |
| 58 | Ethyl 1-(6-(3-fluoro-4-methoxyphenyl)quinolin-2-yl)piperidine-4-carboxylate | ++++ | ++++ |
| 63 | Ethyl 1-(6-(4-chloro-3-fluorophenyl)quinolin-2-yl)piperidine-4-carboxylate | ++++ | ++++ |
| 64 | Ethyl 1-(6-(3-chlorophenyl)quinolin-2-yl)piperidine-4-carboxylate | +++ | ++++ |
| 67 | Ethyl 1-(6-(pyridin-4-yl)quinolin-2-yl)pyrrolidine-3-carboxylate | +++ | ++++ |
| 68 | Ethyl 1-(6-(benzo[b]thiophen-2-yl)quinolin-2-yl)piperidine-4-carboxylate | +++ | ++++ |
| 69 | Ethyl 1-(6-(2-(trifluoromethyl)phenyl)quinolin-2-yl)piperidine-4-carboxylate | ++++ | +++ |
| 70 | Ethyl 1-(6-(2-(trifluoromethoxy)phenyl)quinolin-2-yl)piperidine-4-carboxylate | ++++ | + |
| 70 | Ethyl 1-(6-(4-fluoro-2-methoxyphenyl)quinolin-2-yl)piperidine-4-carboxylate | ++++ | ++++ |
| 72 | Ethyl 1-(6-(4-methoxy-3-(trifluoromethyl)phenyl)quinolin-2-yl)piperidine-4-carboxylate | +++ | ++++ |
| 74 | Ethyl 1-(6-(3-fluorophenyl)quinolin-2-yl)piperidine-4-carboxylate | +++ | ++++ |
| 75 | Ethyl 1-(6-(3-chloro-4-fluorophenyl)quinolin-2-yl)piperidine-4-carboxylate | +++ | ++++ |

In Table 1, the results of REMA and cytotoxicity are set out as follows:

| | ++++ | +++ | ++ | + |
|---|---|---|---|---|
| MTB growth REMA (μM) | <7.8 | 7.8-15.6 | 15.6-31.5 | 31.5-62.5 |
| IC$_{50}$ (μM) | >100 | 50-100 | 20-50 | <20 |

TABLE 2

REMA and IC$_{50}$ results for selected the compounds

| Compound Number | Name | REMA MIC | IC$_{50}$ |
|---|---|---|---|
| 2 | 1-(6-(4-(Trifluoromethoxy)phenyl)quinolin-2-yl)piperidine-4-carboxylic acid | ++++ | ++++ |
| 4 | Ethyl 1-(6-(2-methoxypyrimidin-5-yl)quinolin-2-yl)piperidine-4-carboxylate | ++++ | ++++ |
| 8 | Ethyl 1-(6-(3-fluorophenyl)quinolin-2-yl)piperidine-4-carboxylate | ++++ | ++++ |
| 10 | 1-(6-(3-Fluoro-4-isopropoxyphenyl)quinolin-2-yl)piperidine-4-carboxylic acid | ++++ | ++++ |
| 11 | 1-(6-(3-Fluorophenyl)quinolin-2-yl)piperidine-4-carboxylic acid | ++++ | ++++ |
| 14 | Ethyl 1-(6-(6-methoxypyridin-3-yl)quinolin-2-yl)piperidine-4-carboxylate | ++++ | ++++ |
| 19 | Ethyl 1-(6-(2-chloro-4-methoxyphenyl)quinolin-2-yl)piperidine-4-carboxylate | ++++ | +++ |
| 21 | 1-(6-(4-Methoxyphenyl)quinolin-2-yl)piperidine-4-carboxylic acid | ++++ | ++++ |

TABLE 2-continued

REMA and IC$_{50}$ results for selected the compounds

| Compound Number | Name | REMA MIC | IC$_{50}$ |
|---|---|---|---|
| 24 | Ethyl 1-(6-(4-methoxy-2-(trifluoromethyl)phenyl)quinolin-2-yl)piperidine-4-carboxylate hydrochloride | ++++ | +++ |
| 25 | Ethyl 1-(6-(3-(trifluoromethoxy)phenyl)quinolin-2-yl)piperidine-4-carboxylate | ++++ | ++++ |
| 26 | Ethyl 1-(6-(3-hydroxyphenyl)quinolin-2-yl)piperidine-4-carboxylate | ++++ | ++++ |
| 29 | 1-(6-(3-(Trifluoromethoxy)phenyl)quinolin-2-yl)piperidine-4-carboxylic acid | ++++ | ++++ |
| 50 | Ethyl 1-(6-(6-methylpyridin-3-yl)quinolin-2-yl)piperidine-4-carboxylate | ++++ | ++++ |
| 55 | Ethyl 1-(6-(pyridin-2-yl)quinolin-2-yl)piperidine-4-carboxylate | ++++ | +++ |
| 58 | Ethyl 1-(6-(3-fluoro-4-methoxyphenyl)quinolin-2-yl)piperidine-4-carboxylate | ++++ | ++++ |
| 63 | Ethyl 1-(6-(4-chloro-3-fluorophenyl)quinolin-2-yl)piperidine-4-carboxylate | ++++ | ++++ |
| 69 | Ethyl 1-(6-(2-(trifluoromethyl)phenyl)quinolin-2-yl)piperidine-4-carboxylate | ++++ | +++ |
| 71 | Ethyl 1-(6-(4-fluoro-2-methoxyphenyl)quinolin-2-yl)piperidine-4-carboxylate | ++++ | ++++ |

In the table 2, the results of REMA and cytotoxicity are set out as follows:

| | ++++ | +++ | ++ | + |
|---|---|---|---|---|
| MTB growth REMA (μM) | <7.8 | 7.8-15.6 | 15.6-31.5 | 31.5-62.5 |
| IC$_{50}$ (μM) | >100 | 50-100 | 20-50 | <20 |

In an embodiment, the compounds of the present disclosure have been shown to inhibit the growth of *Mycobacterium tuberculosis* in a standard REMA assay (Palomino J C et al, *Mycobacterium tuberculosis Antimicrob. Agents Chemother.* 2002, 46, 8, 2720-2722) with minimum inhibitory concentration (MIC) of not more than 15.6 IM. Surprisingly, the compounds of the present disclosure presented MIC not more than 15.6 μM. Even more surprising, the embodiments for better results of the present disclosure have MIC of not more than 7.8 μM. The compounds of the disclosure have also been found to be non-cytotoxic for HepG2 cell line, metabolically stable in human microsomes, stable in plasma and relatively permeable under gastrointestinal tract parallel artificial membrane. Log D and pKa, have been described. The compounds disclosed are promising antimycobacterial agents.

In an embodiment, the compounds of the disclosure were tested in assay outlined in example 4 as described above and the following results were obtained.

TABLE 3

CI$_{int}$ and t$_{1/2}$ results for selected compounds

| Compound Number | Name | CI$_{int}$ (μl/min/mg) | t$_{1/2}$ (min) |
|---|---|---|---|
| 18 | 1-(6-(Pyridin-4-yl)quinolin-2-yl)piperidine-4-carboxylic acid hydrochloride | ≤1 | n.d. |
| 21 | 1-(6-(4-Methoxyphenyl)quinolin-2-yl)piperidine-4-carboxylic acid | 19 | 87.4 |
| 23 | 1-(6-(2-Chloro-4-methoxyphenyl)quinolin-2-yl)piperidine-4-carboxylic acid | 26 | 64.1 |
| 27 | 1-(6-(3-Hydroxyphenyl)quinolin-2-yl)piperidine-4-carboxylic acid | ≤1 | n.d. |
| 29 | 1-(6-(3-(Trifluoromethoxy)phenyl)quinolin-2-yl)piperidine-4-carboxylic acid | 9 | 186.4 |
| 36 | 1-(6-(4-(Trifluoromethyl)phenyl)quinolin-2-yl)piperidine-4-carboxylic acid | 4 | 456.5 |
| 47 | 1-(6-(4-Fluorophenyl)quinolin-2-yl)piperidine-4-carboxylic acid | ≤1 | n.d. |
| 52 | 1-(6-(6-(Trifluoromethyl)pyridin-3-yl)quinolin-2-yl)piperidine-4-carboxylic acid hydrochloride | 3 | 558.8 | n.d. = not determined

In an embodiment, the compounds of the disclosure were tested in assay outlined in example 5, 6, 7, 8 and 9 as described above and the following results were obtained:

TABLE 4

Further biological data for selected compounds

| Compound Number | Name | $t_{1/2}$ (min) hPS | hPPB | GIT PAMPA $\log[10^{-6}$ cm/s] | LogD | pKa |
|---|---|---|---|---|---|---|
| 2 | 1-(6-(4-(Trifluoromethoxy)phenyl)quinolin-2-yl)piperidine-4-carboxylic acid | >120 | ≥99 | −4.6 | 2.88 | n.d. |
| 10 | 1-(6-(3-Fluoro-4-isopropoxyphenyl)quinolin-2-yl)piperidine-4-carboxylic acid | >120 | 99 | −4.6 | 2.75 | n.d. |
| 11 | 1-(6-(3-Fluorophenyl)quinolin-2-yl)piperidine-4-carboxylic acid | >120 | 99 | −4.0 | 2.12 | n.d. |
| 14 | Ethyl 1-(6-(6-methoxypyridin-3-yl)quinolin-2-yl)piperidine-4-carboxylate | >120 | ≥99 | −4.9 | 4.28 | n.d. |
| 18 | 1-(6-(Pyridin-4-yl)quinolin-2-yl)piperidine-4-carboxylic acid hydrochloride | >120 | 95 | ≤−7 | 0.81 | 4.4, 9.6 |
| 19 | Ethyl 1-(6-(2-chloro-4-methoxyphenyl)quinolin-2-yl)piperidine-4-carboxylate | >120 | ≥99 | −5.6 | 3.99 | n.d. |
| 21 | 1-(6-(4-Methoxyphenyl)quinolin-2-yl)piperidine-4-carboxylic acid | >120 | 99 | ≤−7 | 1.83 | 2.8, 9.8 |
| 23 | 1-(6-(2-Chloro-4-methoxyphenyl)quinolin-2-yl)piperidine-4-carboxylic acid | >120 | ≥99 | −4.2 | 2.46 | 4.1, 6.9 |
| 24 | Ethyl 1-(6-(4-methoxy-2-(trifluoromethyl)phenyl)quinolin-2-yl)piperidine-4-carboxylate hydrochloride | >120 | ≥99 | −5.3 | 3.18 | n.d. |
| 25 | Ethyl 1-(6-(3-(trifluoromethoxy)phenyl)quinolin-2-yl)piperidine-4-carboxylate | >120 | ≥99 | −5.8 | 2.49 | n.d. |
| 26 | Ethyl 1-(6-(3-hydroxyphenyl)quinolin-2-yl)piperidine-4-carboxylate | >120 | ≥99 | −5.3 | >4.5 | n.d. |
| 27 | 1-(6-(3-Hydroxyphenyl)quinolin-2-yl)piperidine-4-carboxylic acid | >120 | 99 | −5.1 | 1.34 | 7.0, 10.8 |
| 29 | 1-(6-(3-(Trifluoromethoxy)phenyl)quinolin-2-yl)piperidine-4-carboxylic acid | >120 | ≥99 | −4.4 | 3.11 | <2, 10.0 |
| 36 | 1-(6-(4-(Trifluoromethyl)phenyl)quinolin-2-yl)piperidine-4-carboxylic acid | >120 | ≥99 | −4.4 | 2.93 | <2, 10.0 |
| 47 | 1-(6-(4-fluorophenyl)quinolin-2-yl)piperidine 4 carboxylic acid | >120 | 99 | −4.3 | 2.02 | 2.3, 9.0 |
| 50 | Ethyl 1-(6-(6-methylpyridin-3-yl)quinolin-2-yl)piperidine-4-carboxylate | >120 | ≥99 | −4.5 | 2.21 | n.d. |
| 52 | 1-(6-(6-(Trifluoromethyl)pyridin-3-yl)quinolin-2-yl)piperidine-4-carboxylic acid hydrochloride | >120 | 99 | −4.8 | 1.61 | 3.8, 10.0 |
| 55 | Ethyl 1-(6-(pyridin-2-yl)quinolin-2-yl)piperidine-4-carboxylate | >120 | ≥99 | −4.6 | 3.51 | n.d. |
| 58 | Ethyl 1-(6-(3-fluoro-4-methoxyphenyl)quinolin-2-yl)piperidine-4-carboxylate | >120 | ≥99 | −5.0 | 2.26 | n.d. |
| 63 | Ethyl 1-(6-(4-chloro-3-fluorophenyl)quinolin-2-yl)piperidine-4-carboxylate | >120 | ≥99 | −5.1 | 4.02 | n.d. |
| 64 | Ethyl 1-(6-(3-chlorophenyl)quinolin-2-yl)piperidine-4-carboxylate | >120 | ≥99 | −6.1 | 4.32 | n.d. |
| 66 | Ethyl 1-(6-(3-(trifluoromethyl)phenyl)quinolin-2-yl)piperidine-4-carboxylate | >120 | ≥99 | −6.4 | 4.29 | n.d. |
| 67 | Ethyl 1-(6-(pyridin-4-yl)quinolin-2-yl)pyrrolidine-3-carboxylate | 78 | 98 | −4.0 | 3.73 | n.d. |
| 68 | Ethyl 1-(6-(benzo[b]thiophen-2-yl)quinolin-2-yl)piperidine-4-carboxylate | >120 | ≥99 | −5.5 | 2.65 | n.d. |

TABLE 4-continued

Further biological data for selected compounds

| Compound Number | Name | $t_{1/2}$ (min) hPS | hPPB | GIT PAMPA log[$10^{-6}$ cm/s] | LogD | pKa |
|---|---|---|---|---|---|---|
| 69 | Ethyl 1-(6-(2-(trifluoromethyl)phenyl)quinolin-2-yl)piperidine-4-carboxylate | >120 | ≥99 | −5.4 | 3.38 | n.d. |
| 71 | Ethyl 1-(6-(4-fluoro-2-methoxyphenyl)quinolin-2-yl)piperidine 4 carboxylate | >120 | ≥99 | −5.0 | 3.49 | n.d. |
| 72 | Ethyl 1-(6-(4-methoxy-3-(trifluoromethyl)phenyl)quinolin-2-yl)piperidine-4-carboxylate | >120 | ≥99 | −5.7 | 2.83 | n.d. |
| 74 | Ethyl 1-(6-(3-fluorophenyl)quinolin-2-yl)piperidine-4-carboxylate | >120 | ≥99 | −5.7 | 4.00 | n.d. |
| 75 | Ethyl 1-(6-(3-chloro-4-fluorophenyl)quinolin-2-yl)piperidine-4-carboxylate | >120 | ≥99 | −6.3 | 4.00 | n.d. | n.d.—Not determined.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof. The above described embodiments are combinable.

The following claims further set out particular embodiments of the disclosure.

The invention claimed is:

1. A compound of general formula I or a pharmaceutically acceptable salt, hydrate, solvate, N-oxide, stereoisomer, diastereoisomer, enantiomer or atropisomer, polymorph or ester thereof:

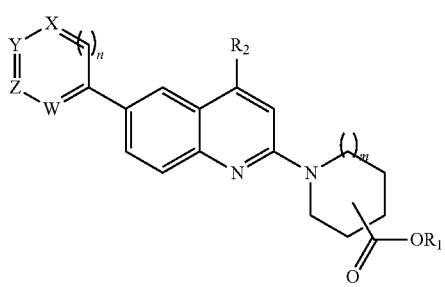

Formula I wherein
$R_1$, $R_2$, X, Y, Z, W, are independently selected from each other;
$R_1$ is selected from H or $C_1$-$C_6$ alkyl;
$R_2$ is selected from H or $C_1$-$C_6$ alkyl;
X is selected from N, O, S or $CR_3$, and $R_3$ is selected from H, halogen, $C_1$-$C_6$ alkoxy or $C_1$-$C_6$ haloalkyl;
Y is selected from N or $CR_4$, and $R_4$ is selected from H, $C_1$-$C_6$ haloalkoxy, OH, $C_1$-$C_6$ alkoxy, $C_1$-$C_6$ haloalkyl, halogen or $C_1$-$C_6$ alkyl;
Z is selected from N or $CR_5$, and $R_5$ is selected from H, halogen, $C_1$-$C_6$ alkoxy, $C_1$-$C_6$ haloalkyl, $C_1$-$C_6$ haloalkoxy, OH, $NO_2$ or $C_1$-$C_6$ alkyl;
W is selected from N, or $CR_6$, and $R_6$ is selected from H, $C_1$-$C_6$ alkoxy, $C_1$-$C_6$ haloalkyl, halogen, or $C_1$-$C_6$ haloalkoxy;
m and n are independently selected from 0 or 1;
further wherein halogen is F or Cl;
and wherein the group connected to the quinoline moiety on $C_6$ is a substituted aryl, a substituted or unsubstituted heteroaryl or fused heteroaroaryl ring selected from pyridin-2-yl, pyridin-3-yl, pyridin-4-yl, pyrimidin-5-yl, furan-2-yl, benzothiophenyl, indolyl or phenyl,
and the piperidine ring that is connected to the quinoline moiety on $C_2$, has its $C_3$ or $C_4$ substituted with carboxylate group.

2. The compound of claim 1, wherein
R1 is selected from H, $CH_2CH_3$ or $CH_3$;
R2 is selected from H or $CH_3$;
X is selected from N, O, S or $CR_3$, and $R_3$ is selected from H, Cl, F, $CF_3$ or $OCH_3$;
Y is selected from N or $CR_4$, and $R_4$ is selected from H, F, Cl, $CH_3$, OH, $CF_3$, $OCF_3$, $OCH(CH_3)_2$ or $OCH_3$;
Z is selected from N or $CR_5$, and $R_5$ is H, OH, F, $OCF_3$, $OCH_3$, $NO_2$, $CF_3$ or $CH_3$;
W is selected from N or $CR_6$ and $R_6$ is H, F, Cl, $CF_3$, $OCH_3$ or $OCF_3$;
m and n are independently selected from 0 or 1;
and wherein the group connected to the quinoline moiety on $C_6$ is a substituted aryl, a substituted or unsubstituted heteroaryl or fused heteroaroaryl ring selected from pyridin-2-yl, pyridin-3-yl, pyridin-4-yl, pyrimidin-5-yl, furan-2-yl, benzothiophenyl, indolyl or phenyl.

3. The compound of claim 1, of Formula II wherein

Formula II $R_1$ is selected from H or $CH_2CH_3$;

$R_3$ is selected from H, Cl, F, $CF_3$ or $OCH_3$;

$R_4$ is selected from H, OH, Cl, F, $OCF_3$, $CH_3$, $CF_3$, $OCH(CH_3)_2$ or $OCH_3$;

$R_5$ is selected from H, OH, F, $OCF_3$, $CF_3$, $CH_3$, $OCH_3$ or $NO_2$;

$R_6$ is selected from H, Cl, F, $CF_3$, $OCF_3$ or $OCH_3$;

further wherein that the group connected to the quinoline moiety on $C_6$ is a substituted aryl, substituted or unsubstituted heteroaryl or fused heteroaroaryl ring selected from indolyl or phenyl.

4. The compound of claim 1, of Formula III, wherein

Formula III

R1 is selected from H, $CH_2CH_3$ or $CH_3$;

R2 is selected from H and $CH_3$;

X is selected from N, or $CR_3$, and $R_3$ is H;

Y is selected from N or $CR_4$, and $R_4$ is selected from H, $CH_3$, F, $CF_3$ or $OCH_3$;

Z is selected from N or $CR_5$, and $R_5$ is selected from H or $CH_3$;

W is selected from N or $CR_6$, and $R_6$ is selected from H or F;

m is selected from 0 or 1;

further wherein the group connected to the quinoline moiety on $C_6$ is a substituted aryl, substituted or unsubstituted heteroaryl or fused heteroaroaryl ring selected from pyridin-2-yl, pyridin-3-yl, pyridin-4-yl or pyrimidin-5-yl.

5. The compound of claim 1, of Formula IV, wherein

Formula IV

X is O or S;

R1 is selected from H or $CH_2CH_3$;

further wherein the group connected to the quinoline moiety on $C_6$ is a substituted or unsubstituted heteroaryl or fused heteroaroaryl ring selected from furan-2-yl or benzothiophenyl.

6. The compound according to claim 3, wherein $R_3$ is H, Cl, F or $CF_3$.

7. The compound according to claim 3, wherein $R_4$ is H, Cl, F, $OCF_3$, $OCH(CH_3)_2$ or $OCH_3$, $R_5$ is H, Cl, F, OH, $OCF_3$ or $CF_3$, and $R_6$ is H, Cl, $CF_3$ or $OCH_3$.

8. The compound according to claim 4, wherein one or more of Y, Z or W is N.

9. The compound according to claim 8, wherein $R_4$ is $OCH_3$ or $CH_3$ and Z is N.

10. The compound according to claim 8, wherein W is N.

11. The compound of claim 1, wherein the salt is a hydrochloride.

12. The compound of claim 1, wherein the compound is:

Ethyl 1-(6-(4-(trifluoromethoxy)phenyl)quinolin-2-yl)piperidine-4-carboxylate;

1-(6-(4-(Trifluoromethoxy)phenyl)quinolin-2-yl)piperidine-4-carboxylic acid;

Ethyl 1-(6-(4-hydroxyphenyl)quinolin-2-yl)piperidine-4-carboxylate;

Ethyl 1-(6-(2-methoxypyrimidin-5-yl)quinolin-2-yl)piperidine-4-carboxylate;

Ethyl 1-(6-(4-isopropoxyphenyl)quinolin-2-yl)piperidine-4-carboxylate;

1-(6-(2-Methoxypyrimidin-5-yl)quinolin-2-yl)piperidine-4-carboxylic acid;

1-(6-(4-Isopropoxyphenyl)quinolin-2-yl)piperidine-4-carboxylic acid;

Ethyl 1-(6-(3-fluorophenyl)quinolin-2-yl)piperidine-4-carboxylate;

1-(6-(4-Hydroxyphenyl)quinolin-2-yl)piperidine-4-carboxylic acid;

1-(6-(3-Fluoro-4-isopropoxyphenyl)quinolin-2-yl)piperidine-4-carboxylic acid;

1-(6-(3-Fluorophenyl)quinolin-2-yl)piperidine-4-carboxylic acid;

Ethyl 1-(6-(3-fluoro-4-isopropoxyphenyl)quinolin-2-yl)piperidine-4-carboxylate;

1-(6-(6-Methoxypyridin-3-yl)quinolin-2-yl)piperidine-4-carboxylic acid;

Ethyl 1-(6-(6-methoxypyridin-3-yl)quinolin-2-yl)piperidine-4-carboxylate;

Ethyl 1-(6-(pyridin-4-yl)quinolin-2-yl)piperidine-4-carboxylate hydrochloride;

Ethyl 1-(6-(furan-2-yl)quinolin-2-yl)piperidine-4-carboxylate;

1-(6-(Furan-2-yl)quinolin-2-yl)piperidine-4-carboxylic acid;
1-(6-(Pyridin-4-yl)quinolin-2-yl)piperidine-4-carboxylic acid hydrochloride;
Ethyl 1-(6-(2-chloro-4-methoxyphenyl)quinolin-2-yl)piperidine-4-carboxylate;
Ethyl 1-(6-(4-methoxyphenyl)quinolin-2-yl)piperidine-4-carboxylate;
1-(6-(4-Methoxyphenyl)quinolin-2-yl)piperidine-4-carboxylic acid;
1-(6-(3-Methoxyphenyl)quinolin-2-yl)piperidine-4-carboxylic acid;
1-(6-(2-Chloro-4-methoxyphenyl)quinolin-2-yl)piperidine-4-carboxylic acid;
Ethyl 1-(6-(4-methoxy-2-(trifluoromethyl)phenyl)quinolin-2-yl)piperidine-4-carboxylate hydrochloride;
Ethyl 1-(6-(3-(trifluoromethoxy)phenyl)quinolin-2-yl)piperidine-4-carboxylate;
Ethyl 1-(6-(3-hydroxyphenyl)quinolin-2-yl)piperidine-4-carboxylate;
1-(6-(3-Hydroxyphenyl)quinolin-2-yl)piperidine-4-carboxylic acid;
1-(6-(4-Methoxy-2-(trifluoromethyl)phenyl)quinolin-2-yl)piperidine-4-carboxylic acid;
1-(6-(3-(Trifluoromethoxy)phenyl)quinolin-2-yl)piperidine-4-carboxylic acid;
Ethyl 1-(6-(3-methoxyphenyl)quinolin-2-yl)piperidine-4-carboxylate;
Ethyl 1-(6-(4-(trifluoromethyl)phenyl)quinolin-2-yl)piperidine-4-carboxylate;
Ethyl 1-(6-(3-nitrophenyl)quinolin-2-yl)piperidine-4-carboxylate;
Ethyl 1-(6-(4-fluorophenyl)quinolin-2-yl)piperidine-4-carboxylate;
Ethyl 1-(6-(pyridin-3-yl)quinolin-2-yl)piperidine-4-carboxylate;
Ethyl 1-(6-(6-fluoropyridin-3-yl)quinolin-2-yl)piperidine-4-carboxylate;
1-(6-(4-(Trifluoromethyl)phenyl)quinolin-2-yl)piperidine-4-carboxylic acid;
Ethyl 1-(6-(2-fluoropyridin-4-yl)quinolin-2-yl)piperidine-4-carboxylate;
1-(6-(6-Fluoropyridin-3-yl)quinolin-2-yl)piperidine-4-carboxylic acid hydrochloride;
1-(6-(3-Nitrophenyl)quinolin-2-yl)piperidine-4-carboxylic acid;
Ethyl 1-(6-(2-methylpyridin-4-yl)quinolin-2-yl)piperidine-4-carboxylate;
Ethyl 1-(6-(3,5-dimethoxyphenyl)quinolin-2-yl)piperidine-4-carboxylate;
Ethyl 1-(6-(1H-indol-5-yl)quinolin-2-yl)piperidine-4-carboxylate;
Ethyl 1-(6-(6-(trifluoromethyl)pyridin-3-yl)quinolin-2-yl)piperidine-4-carboxylate;
Ethyl 1-(6-(pyrimidin-5-yl)quinolin-2-yl)piperidine-4-carboxylate;
1-(6-(1H-Indol-5-yl)quinolin-2-yl)piperidine-4-carboxylic acid hydrochloride;
1-(6-(3,5-Dimethoxyphenyl)quinolin-2-yl)piperidine-4-carboxylic acid;
1-(6-(4-Fluorophenyl)quinolin-2-yl)piperidine-4-carboxylic acid;
1-(6-(Pyrimidin-5-yl)quinolin-2-yl)piperidine-4-carboxylic acid;
1-(6-(Pyridin-3-yl)quinolin-2-yl)piperidine-4-carboxylic acid;
Ethyl 1-(6-(6-methylpyridin-3-yl)quinolin-2-yl)piperidine-4-carboxylate;
1-(6-(2-Fluoropyridin-4-yl)quinolin-2-yl)piperidine-4-carboxylic acid hydrochloride;
1-(6-(6-(Trifluoromethyl)pyridin-3-yl)quinolin-2-yl)piperidine-4-carboxylic acid hydrochloride;
1-(6-(2-Methylpyridin-4-yl)quinolin-2-yl)piperidine-4-carboxylic acid;
Ethyl 1-(6-(pyridin-4-yl)quinolin-2-yl)piperidine-3-carboxylate;
Ethyl 1-(6-(pyridin-2-yl)quinolin-2-yl)piperidine-4-carboxylate;
1-(4-Methyl-6-(pyridin-4-yl)quinolin-2-yl)piperidine-4-carboxylic acid;
Ethyl 1-(4-methyl-6-(pyridin-4-yl)quinolin-2-yl)piperidine-4-carboxylate;
Ethyl 1-(6-(3-fluoro-4-methoxyphenyl)quinolin-2-yl)piperidine-4-carboxylate;
Ethyl 1-(6-(3-chloro-4-methoxyphenyl)quinolin-2-yl)piperidine-4-carboxylate;
ethyl 1-(6-(3,4-dimethoxyphenyl)quinolin-2-yl)piperidine-4-carboxylate;
1-(6-(Pyridin-2-yl)quinolin-2-yl)piperidine-4-carboxylic acid;
1-(6-(Pyridin-4-yl)quinolin-2-yl)piperidine-3-carboxylic acid hydrochloride;
Ethyl 1-(6-(4-chloro-3-fluorophenyl)quinolin-2-yl)piperidine-4-carboxylate;
Ethyl 1-(6-(3-chlorophenyl)quinolin-2-yl)piperidine-4-carboxylate;
Ethyl 1-(6-(4-chlorophenyl)quinolin-2-yl)piperidine-4-carboxylate;
Ethyl 1-(6-(3-(trifluoromethyl)phenyl)quinolin-2-yl)piperidine-4-carboxylate;
Ethyl 1-(6-(pyridin-4-yl)quinolin-2-yl)pyrrolidine-3-carboxylate;
Ethyl 1-(6-(benzo[b]thiophen-2-yl)quinolin-2-yl)piperidine-4-carboxylate;
Ethyl 1-(6-(2-(trifluoromethyl)phenyl)quinolin-2-yl)piperidine-4-carboxylate;
Ethyl 1-(6-(2-(trifluoromethoxy)phenyl)quinolin-2-yl)piperidine-4-carboxylate;
Ethyl 1-(6-(4-fluoro-2-methoxyphenyl)quinolin-2-yl)piperidine-4-carboxylate;
Ethyl 1-(6-(4-methoxy-3-(trifluoromethyl)phenyl)quinolin-2-yl)piperidine-4-carboxylate;
Ethyl 1-(6-(4-chloro-3-methoxyphenyl)quinolin-2-yl)piperidine-4-carboxylate;
Ethyl 1-(6-(3-chloro-4-fluorophenyl)quinolin-2-yl)piperidine-4-carboxylate;
Ethyl 1-(6-(2-methoxypyridin-3-yl)quinolin-2-yl)piperidine-4-carboxylate;
Ethyl 1-(6-(5-fluoropyridin-3-yl)quinolin-2-yl)piperidine-4-carboxylate;
Ethyl 1-(6-(3-fluoropyridin-4-yl)quinolin-2-yl)piperidine-4-carboxylate;
Methyl 1-(6-(pyridin-4-yl)quinolin-2-yl)piperidine-4-carboxylate; or
1-(6-(6-methylpyridin-3-yl)quinolin-2-yl)piperidine-4-carboxylic acid hydrochloride.

13. The compound of claim 1, wherein the compound is selected from:
1-(6-(4-(trifluoromethoxy)phenyl)quinolin-2-yl)piperidine-4-carboxylic acid;
ethyl 1-(6-(2-methoxypyrimidin-5-yl)quinolin-2-yl)piperidine-4-carboxylate;

ethyl 1-(6-(3-fluorophenyl)quinolin-2-yl)piperidine-4-carboxylate;
1-(6-(3-fluoro-4-isopropoxyphenyl)quinolin-2-yl)piperidine-4-carboxylic acid;
1-(6-(3-fluorophenyl)quinolin-2-yl)piperidine-4-carboxylic acid;
ethyl 1-(6-(6-methoxypyridin-3-yl)quinolin-2-yl)piperidine-4-carboxylate;
ethyl 1-(6-(2-chloro-4-methoxyphenyl)quinolin-2-yl)piperidine-4-carboxylate;
1-(6-(4-methoxyphenyl)quinolin-2-yl)piperidine-4-carboxylic acid;
ethyl 1-(6-(4-methoxy-2-(trifluoromethyl)phenyl)quinolin-2-yl)piperidine-4-carboxylate hydrochloride;
ethyl 1-(6-(3-(trifluoromethoxy)phenyl)quinolin-2-yl)piperidine-4-carboxylate;
ethyl 1-(6-(3-hydroxyphenyl)quinolin-2-yl)piperidine-4-carboxylate;
1-(6-(3-(trifluoromethoxy)phenyl)quinolin-2-yl)piperidine-4-carboxylic acid;
ethyl 1-(6-(6-methylpyridin-3-yl)quinolin-2-yl)piperidine-4-carboxylate;
ethyl 1-(6-(pyridin-2-yl)quinolin-2-yl)piperidine-4-carboxylate;
ethyl 1-(6-(3-fluoro-4-methoxyphenyl)quinolin-2-yl)piperidine-4-carboxylate;
ethyl 1-(6-(4-chloro-3-fluorophenyl)quinolin-2-yl)piperidine-4-carboxylate;
ethyl 1-(6-(2-(trifluoromethyl)phenyl)quinolin-2-yl)piperidine-4-carboxylate; or
ethyl 1-(6-(4-fluoro-2-methoxyphenyl)quinolin-2-yl)piperidine-4-carboxylate.

14. A method for treating tuberculosis in a subject, the method comprising administering the compound of claim 1 to the subject.

15. The method of claim 14, further comprising administering at least one anti-HIV agent to the subject.

16. The method of claim 15, wherein the anti-HIV agent is selected from an HIV protease inhibitor, an HIV nucleoside reverse transcriptase inhibitor, an HIV non-nucleoside reverse transcriptase inhibitor, and an HIV integrase inhibitor.

17. The method of claim 14, further comprising administering a further tuberculosis drug.

18. The method of claim 17, wherein the further tuberculosis drug is selected from the group of isoniazid, rifamycin and derivatives, pyrazinamide, ethambutol, cycloserine, ethionamide, streptomycin, amikacin, kanamycin, rifampin (rifampicin), aminoglycosides, capreomycin, p-aminosalicyclic acid, levofloxacin, moxafloxacin or gatifloxacin, or mixtures thereof.

19. The method of claim 15, wherein the anti-HIV is administered simultaneously, separately or sequentially.

20. A pharmaceutical composition comprising (i) a therapeutically effective amount of the compound of claim 1 or a pharmaceutically acceptable salt or solvate thereof; and (ii) a pharmaceutically acceptable excipient.

* * * * *